(12) United States Patent
Staats

(10) Patent No.: US 6,864,480 B2
(45) Date of Patent: Mar. 8, 2005

(54) INTERFACE MEMBERS AND HOLDERS FOR MICROFLUIDIC ARRAY DEVICES

(76) Inventor: Sau Lan Tang Staats, 609 Ramsey Rd., Hockessin, DE (US) 19707

( * ) Notice: Subject to any disclaimer, the term of this patent is extended or adjusted under 35 U.S.C. 154(b) by 128 days.

(21) Appl. No.: 10/305,045

(22) Filed: Nov. 26, 2002

(65) Prior Publication Data

US 2004/0021068 A1 Feb. 5, 2004

Related U.S. Application Data

(63) Continuation-in-part of application No. 10/174,343, filed on Jun. 17, 2002, now Pat. No. 6,800,849.
(60) Provisional application No. 60/341,069, filed on Dec. 19, 2001.

(51) Int. Cl.[7] ............................................. H01J 49/00
(52) U.S. Cl. ..................... 250/288; 250/424; 250/425; 250/435
(58) Field of Search ................................. 250/288, 424, 250/435, 428

(56) References Cited

U.S. PATENT DOCUMENTS

| | | |
|---|---|---|
| 4,756,884 A | 7/1988 | Hillman et al. |
| 5,486,335 A | 1/1996 | Wilding et al. |
| 5,900,130 A | 5/1999 | Benvegnu et al. |
| 5,992,820 A | 11/1999 | Fare et al. |
| 6,042,709 A | 3/2000 | Parce et al. |
| 6,068,751 A | 5/2000 | Neukermans |
| 6,136,212 A | 10/2000 | Mastrangelo et al. |
| 6,137,501 A | 10/2000 | Wen et al. |
| 6,627,882 B2 * | 9/2003 | Schultz et al. ............... 250/288 |
| 6,800,849 B2 * | 10/2004 | Staats ......................... 250/288 |
| 2004/0134933 A1 * | 7/2004 | Mutz et al. .................. 222/190 |

OTHER PUBLICATIONS

International Search Report.

* cited by examiner

Primary Examiner—John R. Lee
Assistant Examiner—James J. Leybourne
(74) Attorney, Agent, or Firm—Darby & Darby

(57) ABSTRACT

A member for holding at least one microfluidic device and providing an interface between the at least one microfluidic device and a second device is provided. The at least one microfluidic device has a plurality of reservoirs formed therein and the member includes a body having an upper face and a lower face and a plurality of open well members formed therein. Each well member is defined by a well wall and includes a first end and an opposing second end, wherein the second end is configured and dimensioned for frictionally engaging the at least one microfluidic device such that at least some of the open well members and the reservoirs of the microfluidic device align with one another. An apparatus for interfacing with a mass spectrometer to perform a nanospray application is also provided.

59 Claims, 26 Drawing Sheets

INTERFACE MEMBERS AND HOLDERS FOR MICROFLUIDIC ARRAY DEVICES

CROSS-REFERENCE TO RELATED APPLICATION

This application is a continuation-in-part of U.S. patent application Ser. No. 10/174,343, filed Jun. 17, 2002, now U.S. Pat. No. 6,800,849 which claims the benefit of U.S. patent application Ser. No. 60/341,069, filed Dec. 19, 2001, both of which are hereby incorporated by reference in their entirety

TECHNICAL FIELD

The present invention relates to microfluidic devices, and more particularly, to microfluidic array devices that can be used to deliver one or more samples through one or more nozzles that are formed as part of the microfluidic array device. Exemplary interface members and holders for holding the microfluidic device as the microfluidic device is used in a given application are also disclosed as well as exemplary uses for the microfluidic array devices. For example, the microfluidic array device is suitable for operations designed for lab-on-a-chip functions including analysis of components in the sample fluid by means of optical spectrometry, mass spectrometry, etc.

BACKGROUND

There has been a growing interest in the development and manufacturing of microscale fluid systems for the acquisition of chemical and biochemical information and as a result of this effort, microfluidics is considered an enabling technology for providing low cost, high versatility devices to operations, such as combinatorial chemistry for drug lead discovery and large-scale protein profiling to name a few. Generally, a microfluidic device (which is also often referred to as a lab-on-a-chip device) is a planar device having one or more micron sized channels formed therein and can also include reservoirs, valves, flow switches, etc. The microfluidic features are designed to carry out complex laboratory functions, such as DNA sequencing.

In the absence of using microfluidic devices, the above processes and others are carried out in a manner that is very time intensive and thus, costly. For example, large-scale protein profiling is commonly carried out laboriously but pervasively in the biotechnological and pharmaceutical industries. One particular application of microfluidic devices is to provide microfluidic channels that represent the means to separate analytes in a mixture using techniques, such as capillary electrophoresis and liquid chromatography.

Microfluidic devices have traditionally been fabricated from substantially planar substrates with microfabrication techniques that have been borrowed from the electronics industry, such as photolithography, chemical etching, and laser ablation techniques. When constructing the microfluidic devices in this manner, the microfluidic channels that are formed lie parallel to the surface of one planar surface of the substrate, and the channel is sealed by bonding a second planar substrate to the planar substrate containing the channel. The techniques for detecting materials, such as analytes, that are disposed in the microfluidic channels have for the most part been mainly optical techniques. Fluid transport in the microfluidic devices traditionally entails using electroosmotic, electrokinetic and/or pressure-driven motions of liquid and particles as the means for fluidly transporting such materials.

While the stacking of multiple layers of planar substrates to form a microfluidic structure having layered microfluidic channels is possible in terms of its fabrication, the prevailing detection technology (optically based detection technology) limits the practicality of fabricating such a structure since parallel operation of multiple layers of the planar substrates containing multiple microfluidic separation channels is not practical due to each microfluidic separation channel requiring its own light source and detector.

One detection technology that is fast becoming the detection technique of choice in the biotechnology and pharmaceutical industries is mass spectrometry (MS). Mass spectrometry provides more chemical information about the material being tested (e.g., analytes) than other single detection techniques. For example, molecular weight and even chemical composition of the analytes from small drug candidate molecules to large protein molecules can be successfully analyzed by mass spectrometry (MS) and its related technique that is referred to as MS-MS. In MS-MS, a molecule is ionized and analyzed for molecular weight in the first stage of the mass spectrometer, and then the same molecular ion, called the "parent", is fragmented inside the mass spectrometer to produce "daughter" ions that are further analyzed to give the chemical composition of the parent molecule.

While some progress has been made to interface microfluidic devices with a mass spectrometer, there are still several shortcomings that must be overcome in order to make this interfacing process more practical. For example, one technique that has been discussed involves drilling a small hole, large enough to accommodate a glass or quartz capillary, into the end of the microfluidic channel that is formed by glass substrates and a glass or quartz capillary is then inserted into the drilled hole to act as a nozzle for electrospray ionization. This approach is laborious and is impractical for high throughput operations where many such holes have to be drilled sequentially into the substrates.

In another technique that has been disclosed, a protrusion termed "electropipette" extends from the edge of the substantially planar substrate. The microfluidic channel in this extended region is formed by two planar substrates as in the microfluidic channels that are formed in the rest of the microfluidic device. The outside dimensions of the tip structure include a thickness that is equal to the thickness of the two planar substrates. It has also been disclosed to fabricate an array of nozzles using microfabrication techniques, such as deep ion reactive etching on a silicon wafer. However, the use of silicon wafers as the substrates greatly limits the ability to individually activate each nozzle because of the potential of dielectric breakdown caused by the high voltage applied to the nozzle to create the electrospray conditions, and the volume behind the nozzle made by deep ion reactive etching is extremely difficult to be accessed by conventional means of liquid handling equipment. Integrating this silicon-based nozzle array to microfluidic devices, which are typically made of glass or polymers, is also extremely difficult. The cost of fabricating the nozzles on silicon is also very high.

While injection molding has been discussed as a process for forming microfluidic devices, there are a number of limitations that have equally been associated with such discussion of injection moldable microfluidic devices. For example, it has heretofore been discussed that there are limitations on what size dimensions can be formed when an injection molding process is used to form the microfluidic features. Prior to the present applicant, there was a lack of appreciation and understanding that an injection molding process can be used to form a microfluidic device having microfluidic features with dimensions less than 100 µm. As a result, the use of injection molding as a fabrication process was limited since many microfluidic applications require the microfluidic device to have microfluidic features (e.g., channels) that have dimensions less than 100 µm and more particularly, less than 50 µm.

It would therefore be desirable to provide microfluidic devices, especially microfluidic array devices incorporating nozzles, that overcome the deficiencies of the traditional microfluidic devices and more particularly, the deficiencies that are related to the techniques for fabricating these devices and also to the use of such devices.

SUMMARY

The present application generally relates to microfluidic devices. According to one aspect, a microfluidic device is provided and includes a body having a first surface and an opposing second surface. At least one channel is formed through the body such that the channel extends from the first surface to the opposing second surface with the channel having an open reservoir section formed at the first surface. The microfluidic device further includes at least one nozzle that is disposed along the second surface. The nozzle is in fluid communication with one channel such that each channel terminates in a nozzle opening that is formed as part of the nozzle tip. Unlike traditional microfluidic devices, the exemplary microfluidic device has one or more channels that are open at each end and are formed substantially perpendicular to both the first surface and the second surface where the nozzle is formed.

According to another aspect, the nozzle is conically shaped with the channel extending therethrough and terminating at the nozzle opening. In one exemplary embodiment, the nozzle opening has a diameter equal to or less than 100 µm, preferably equal to or less than 50 µm and more preferably, equal to or less than 20 µm; and an outside diameter of the nozzle, as measured at a tip portion thereof, is less than about 150 µm and preferably is equal to or less than about 100 µm, and more preferably equal to or less than 50 µm. In another aspect of the present application, the microfluidic nozzle array device is formed by an injection molding process that permits the microfluidic nozzle array device to have the above dimensions.

In yet another embodiment, a member for holding at least one microfluidic device and providing an interface between the at least one microfluidic device and a second device is provided. The at least one microfluidic device has a plurality of reservoirs formed therein and the member includes a body having an upper face and a lower face and a plurality of open well members formed therein. Each well member is defined by a well wall and includes a first end and an opposing second end, wherein the second end is configured and dimensioned for frictionally engaging the at least one microfluidic device such that at least some of the open well members and the reservoirs of the microfluidic device align with one another. The member thus not only represents means for retainingly holding the at least one microfluidic device but it also represents means for increasing an effective volume of the reservoir of the microfluidic device since the open well members that align with the reservoirs receive sample that flows into the reservoirs and ultimately, the nozzles.

Moreover and according to another exemplary embodiment of the present application, an apparatus for interfacing with a mass spectrometer to perform a nanospray application is provided. The apparatus includes a microfluidic device having a body including a first surface and an opposing second surface. The body has at least one channel formed therein and extending through the body from the first surface to the second surface, wherein the channel has a reservoir section that is open at the first surface and at least one nozzle disposed along the second surface. The nozzle is in fluid communication with the channel such that one end of the channel terminates in a nozzle opening that is formed as part of a tip of the nozzle. The apparatus also includes a frame disposed around a periphery of the microfluidic device such that the microfluidic device is securely held therein and a holder having first and second retaining members spaced apart a sufficient distance for the frame to be disposed between and held in place by the first and second retaining members, wherein in a retained position, the at least one nozzle is positioned for spraying a sample into an inlet of the mass spectrometer.

In another embodiment, a shield is coupled to at least one of the frame and the holder so that one face of the shield faces the second surface of the microfluidic device. The shield has at least one aperture formed therein which is in axially alignment with the tip of the at least one nozzle. The shield is utilized as a means for preventing or controlling the build-up of the electric field on the polymeric nozzle array device. If the static electric fields are not drained away from the insulating polymer surface during the spray, the stray fields that accumulate on the insulating surface will prevent the ions in the spray from passing into an inlet of an analyzer or the like. The above shield overcomes this situation.

These and other features and advantages of the exemplary embodiments disclosed herein will be readily apparent from the following detailed description taken in conjunction with the accompanying drawings, wherein like reference characters represent like elements.

BRIEF DESCRIPTION OF THE DRAWING FIGURES

The foregoing and other features of the exemplary embodiments will be more readily apparent from the following detailed description and drawings of illustrative embodiments that are not necessarily drawn to show exact likeness or necessarily to scale in which.

DETAILED DESCRIPTION OF PREFERRED EMBODIMENTS

Figure 1:
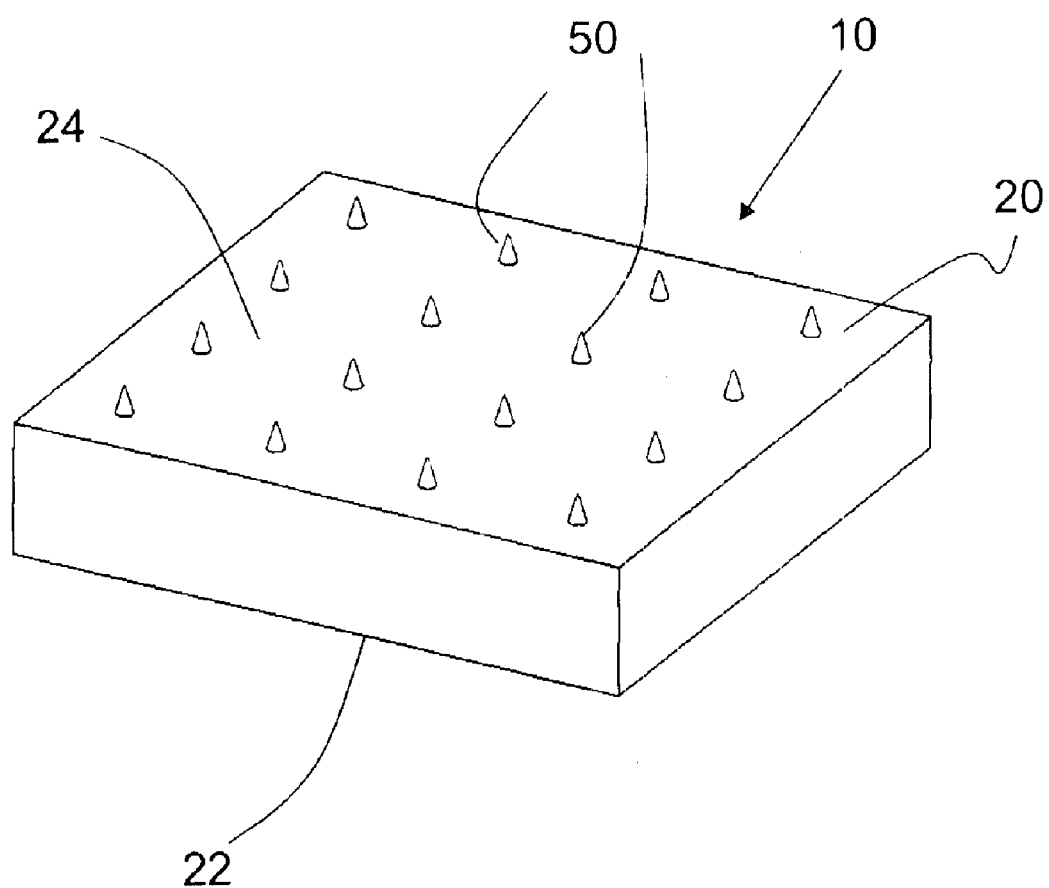
FIG. 1 is a top perspective view of a microfluidic device having an array of nozzles incorporated therein according to a first exemplary embodiment.
Figure 2:
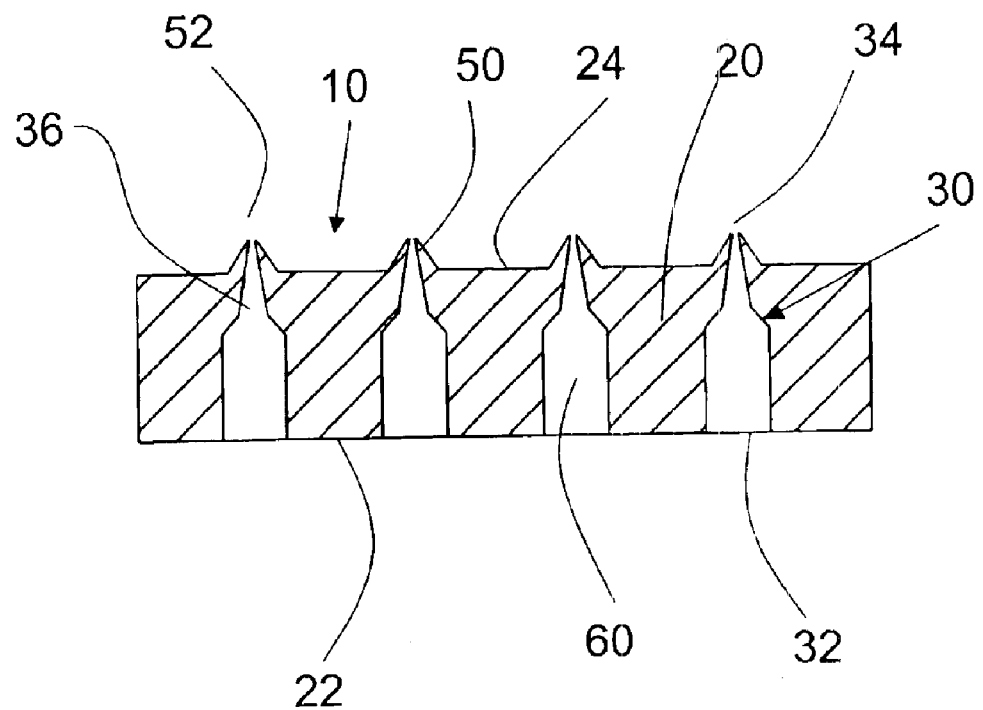
FIG. 2 is a cross-sectional view taken along the line 2—2 of FIG. 1.

Referring first to FIGS. 1–2 in which an exemplary microfluidic device 10 according to one embodiment is illustrated. The microfluidic device 10 has a substrate body 20 that is formed of a polymeric material, as will be described in greater detail hereinafter, and has at least one microfluidic channel 30 that is formed in the substrate body 20. More specifically, the substrate body 20 has a first surface 22 and an opposing second surface 24 with the microfluidic channel 30 being formed between the first and second surfaces 22, 24 such that the microfluidic channel 30 extends the complete thickness of the substrate body 20. The microfluidic channel 30 is thus open at both a first end 32 at the first surface 22 and a second end 34 at the second surface 24. The second end 34 of the microfluidic channel 30 is formed in a protrusion 50 that is formed on the second surface 24 of the substrate body 20. According to one exemplary embodiment, the protrusion 50 has a tapered shape (inward taper) such that it forms a generally conical structure with the open second end 34 preferably being formed at an apex of the conical structure. The tapered protrusion 50 serves as a nozzle that delivers a sample (i.e., a liquid) that is loaded into the microfluidic device 10.

It will be appreciated that in contrast to traditional microfluidic devices, the microfluidic channel 30 is formed in a perpendicular manner in the substrate body 20 in that the microfluidic channel 30 is preferably formed so that it is substantially perpendicular to the first and second surfaces 22, 24 of the substrate body 20. As illustrated, a predetermined number of microfluidic channels 30 and nozzles 50 can be formed in one substrate body 20. The microfluidic channels 30 can be arranged according to any number of different patterns. For example and as illustrated in the exemplary embodiment of FIGS. 1 and 2, which illustrate a preferred arrangement, a plurality of microfluidic channels/nozzles are arranged in regular arrays having spacing that is identical to or similar to spacing of microtiter plates. For example, if 96 microfluidic channels/nozzles are desired, then the 96 microfluidic channels/nozzles are arranged in an 8×12 grid with spacing of about 9 mm between each microfluidic channel/nozzle structure. For a 384 microtiter array, the microfluidic channels/nozzles are placed in a 16×24 grid with spacing of about 4.5 mm. While not entirely to scale, FIG. 2 generally illustrates a section of a microfluidic channel/nozzle array having spacing of about 4.5 mm.

According to the present exemplary embodiments, each nozzle 50 is constructed so that its dimensions are measured in microns. The specific configurations of the nozzle 50 and the microfluidic channel 30 are best shown in FIG. 2. As illustrated, the first end 32 of the microfluidic channel 30 is in the form of a reservoir 60 (i.e., an annular cavity) that tapers inwardly to an intermediate channel section 36. The intermediate channel section 36 also has a tapered construction in that it tapers inwardly toward the second end 34 and the nozzle 50 formed at the second surface 24 of the substrate body 20. Thus, the dimensions of the microfluidic channel 30 are greatest at the first end 32, where the reservoir is formed, and are at a minimum at the second end 34 at a tip portion 52 of the nozzle 50. According to one exemplary embodiment, the open second end 34 of the microfluidic channel 30 formed in nozzle 50 has an inside diameter of about 100 $\mu$m or less, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m. The inside diameter of the microfluidic channel 30 opens gradually in a direction away from the nozzle 50 to about several hundred $\mu$m as the microfluidic channel 30 traverses through the thickness of the substrate body 20 and eventually the microfluidic channel 30 is formed to a diameter of about 1 mm to define the reservoir at the first end 32. The length of the microfluidic channel 30 can be tailored to a given application depending upon a number of factors, such as the desired volume of the reservoir defined at first end 32 and also the thickness of the substrate body 20. According to one exemplary embodiment, the microfluidic channel 30 has a length of about 3 mm or greater. However, the aforementioned dimensions are merely recited to illustrate one exemplary embodiment and it will be understood that the microfluidic device 10 can be fabricated to have other dimensions.

The volume of the reservoir 60 should be such that it can hold an amount of sample material that is typically used in the applications that the microfluidic devices are designed for. For example, the sample volume that is used is from sub-microliter up to 10 microliters for mass spectrometer analysis using electrospray. As will be described in greater detail hereinafter, the sample material is held in the reservoir 60 and is then transported within the microfluidic channel 30 to the nozzle 50 where the sample materials are finally discharged through the open second end 34. The outside diameter of the protruding nozzle 50 also accordingly increases in a direction away from the tip portion 52 thereof. By forming the reservoir 60 or input port at the first surface 22 opposite to the second surface 24, where the nozzle 50 is formed, a sample can easily be fed into the microfluidic channel 30 by injecting or otherwise disposing the sample into one or more reservoirs 50 and then transporting the sample through the associated microfluidic channel 30 using techniques described in greater detail hereinafter.

Figure 3:
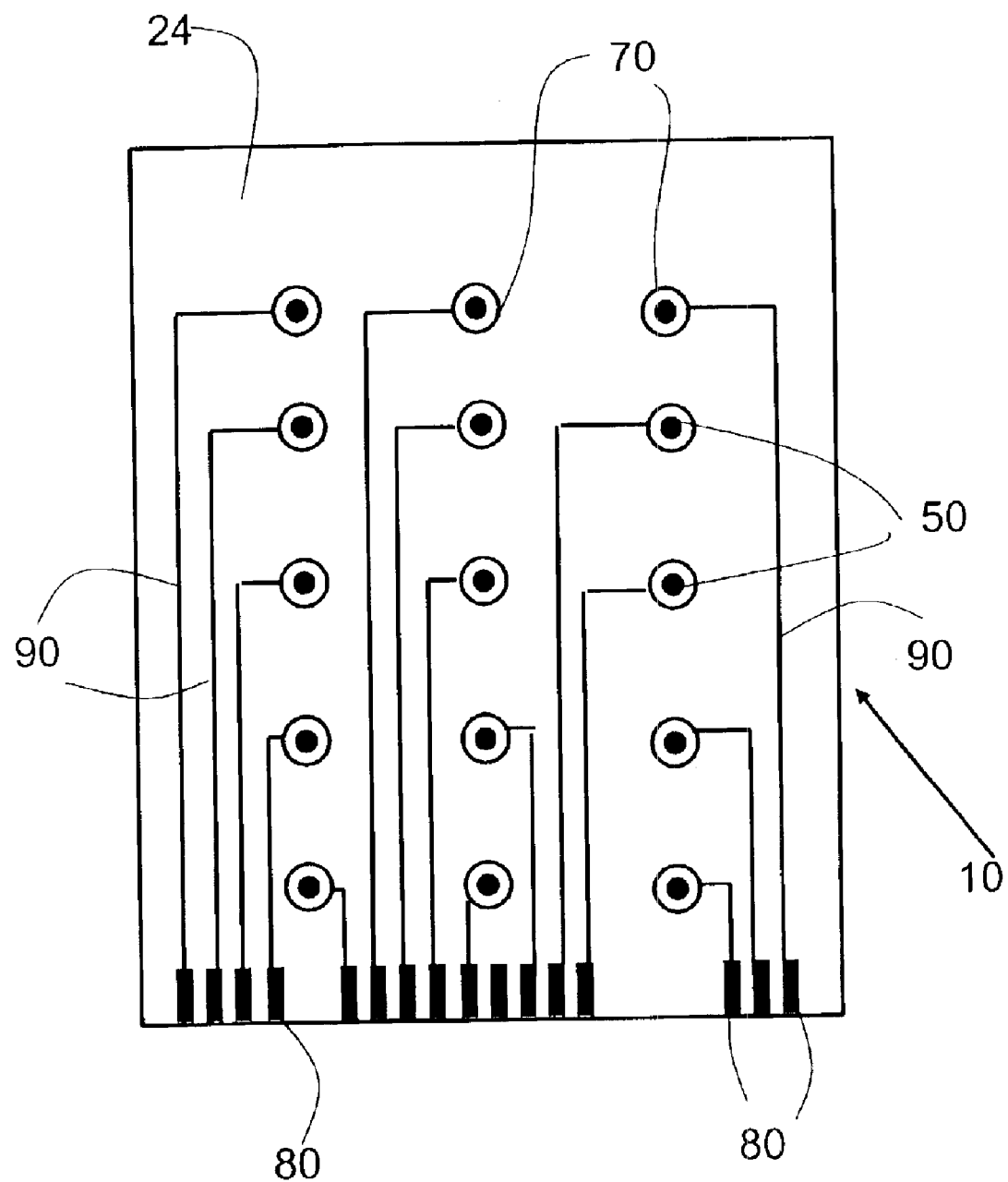
FIG. 3 is a top plan view of the microfluidic device according to FIG. 1 illustrating placement of electrodes around the nozzles and the connections between the electrodes and electrical contacts formed at one edge of the microfluidic device.

Turning now to FIG. 3, the microfluidic device 10 can be fabricated so that it finds particular utility as a means for electrospray ionization of analytes for mass spectrometer analysis. Electrospray is achieved by subjecting the nozzle 50 to a voltage so that liquid and analytes (the "sample") emerge to a high electric field. For this particular application, the microfluidic device 10 includes a conductive region 70 formed on at least a portion of the nozzle 50 and optionally, the conductive region can extend onto the second surface 24. For example, the area around each nozzle 50 up to the extreme end of the nozzle 50 is metallized by evaporation techniques, printing techniques, or other suitable techniques known in the art to form the conductive region 70. Because the nozzle 50 in the illustrated embodiment has a conical shape, the conductive region 70 takes the form of a ring-shaped metal layer with the nozzle 50 being in the center thereof. The thickness of the conductive region 70 can vary depending upon the precise application; however, the conductive region 70 should have a sufficient thickness so that when an electric voltage is applied to the conductive region 70, the sample material (i.e., a liquid) within the microfluidic channel vaporizes and therefore can be used in electrospray or nanospray applications, such as electrospray ionization of analytes for a mass spectrometer. The microfluidic device 10, in this example, provides a low cost, disposable electrospray interface capable of nanospray. This device can be fabricated to accommodate more than one sample input in order to multiplex several separation instruments to a single mass spectrometer.

Each of the conductive regions 70 formed around the nozzles 50 is connected to one or more electrical contacts 80 formed at one edge of the substrate body 20. More specifically, the electrical contacts 80 are preferably in the form of conductive pads (i.e., metallized tabs) that are formed on the second surface 24 of the substrate body 20. FIG. 3 shows one exemplary method of electrically connecting the conductive regions 70 with the electrical contacts 80. In this exemplary arrangement, one conductive region 70 is electrically connected via an electrical pathway 90 to one electrical contact 80. The electrical pathway 90 simply provides an electrical pathway between the conductive region 70 and the electrical contact 80 and is therefore formed of a conductive material (e.g., a metal). For example, the electrical pathway 90 can be in the form of a thin conductive film. By reducing the outside diameter of the tip portion 52 of the nozzle 50 (e.g., to about 50 $\mu$m to 80 $\mu$m), the voltage required to generate the spray is lowered. According to one exemplary embodiment, the voltage used to form the spray is about 5–6 KV for a tip portion 52 having an outside diameter from about 50 $\mu$m to 80 $\mu$m. It will be appreciated that larger sized outside diameters can be used; however, this will require a greater voltage to be applied to the nozzle 50 in order to form a spray.

It will be appreciated that more than one conductive region 70 can be electrically attached to one electrical contact 80 using separate electrical pathways 90 or using a network of electrical pathways or a complete metal film. However, in this embodiment, when an electric voltage is applied to the one electrical contact 80, the electric voltage is applied to each of the conductive regions 70 that is electrically connected to the one electrical contact 80. Thus, the electric voltage can not be selectively delivered to individual nozzles 50 in this particular embodiment.

Figure 4:
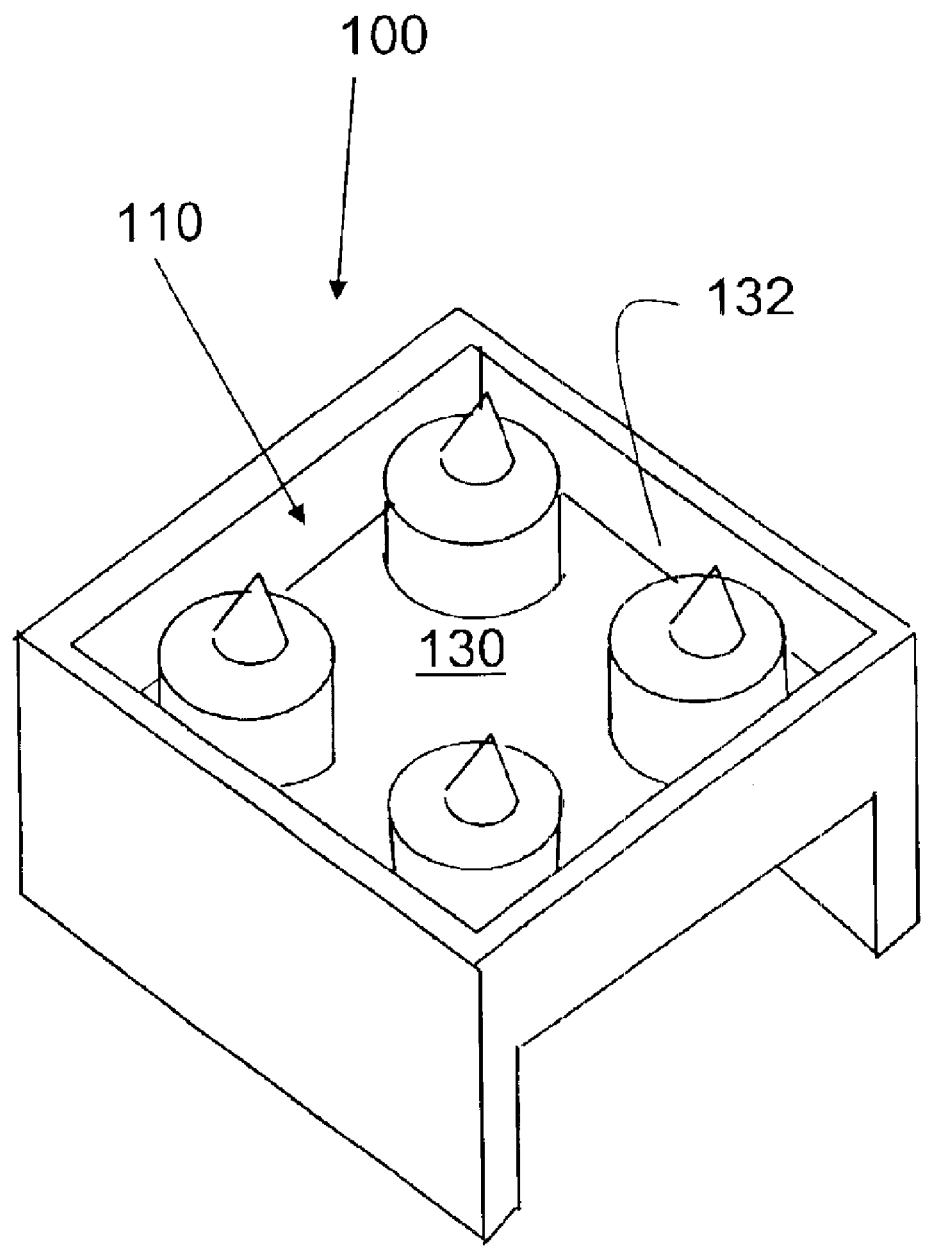
FIG. 4 is a top perspective view of a microfluidic device having an array of nozzles incorporated therein according to a second exemplary embodiment.
Figure 5:
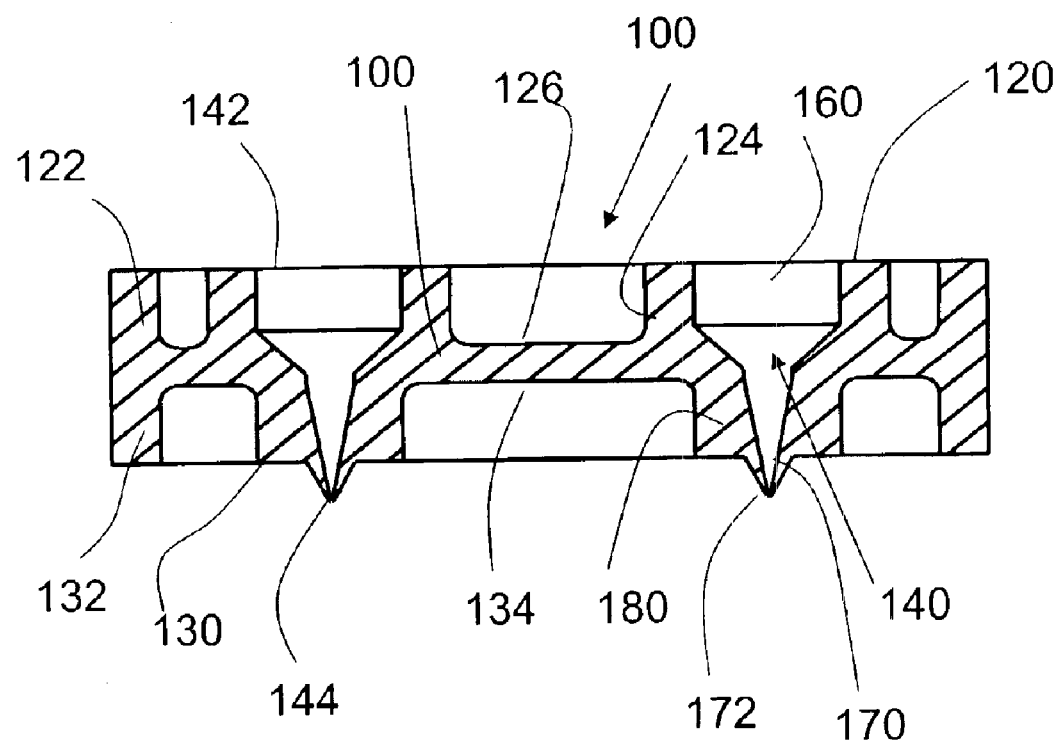
FIG. 5 is a cross-sectional view of the microfluidic device according to FIG. 4.

Now referring to FIGS. 4–5, an exemplary microfluidic device 100 according to a second embodiment is illustrated. The microfluidic device 100 is similar in some respects to the microfluidic device 10 of FIGS. 1–3. The microfluidic device 100 includes a substrate body 110 that is formed of a polymeric material and includes a first face 120 and a second opposing face 130. Unlike the embodiment illustrated in FIGS. 1–3, the first and second faces 120, 130 are not substantially planar surfaces but rather are non-planar in nature due to each of the faces 120, 130 having a number of recesses and protrusions formed therein.

The microfluidic device 100 has at least one microfluidic channel 140 formed therein between the first face 120 and the second face 130 such that the microfluidic channel 140 extends completely through a thickness of the substrate body 110 from the first face 120 to the second face 130. The microfluidic channel 140 is thus open at both a first end 142 at the first face 120 and at a second end 144 at the second face 130. The first face 120 includes a first perimeter wall 122 that extends around a perimeter of the microfluidic device 100 at the first face 120 thereof. In the exemplary embodiment, the microfluidic device 100 is generally square shaped; however, this is merely one exemplary shape for the microfluidic device 100 as the microfluidic device 100 can assume any number of different shapes. Within the boundary of the first perimeter wall 122, one or more reservoir walls 124 are formed with the number of reservoir walls 124 equal to the number of microfluidic channels 140 formed in the substrate body 110. Each reservoir wall 124 partially defines a reservoir 160 that is designed to hold a sample material and the reservoir wall 124 therefore also defines the first end 142 of the microfluidic channel 140. Both the first perimeter wall 122 and the one or more reservoir walls 124 extend above a generally planar surface 126 (i.e., a floor) of the first face 120 in this embodiment. A substantial portion of reservoir 160, which is defined at the first end 142 of the microfluidic device 140, is therefore formed above the planar surface 126.

The second end 144 of the microfluidic channel 140 is formed in a protrusion 170 that extends outwardly from the second face 130. As with the prior embodiment, the protrusion 170 preferably has a tapered shape (inward taper) such that it forms a generally conical structure with the open second end 144 being formed at an apex of the conical structure. The tapered protrusion 170 therefore acts as a nozzle that can discharge a sample that is loaded into the microfluidic channel 140 (e.g., in the reservoir 160). The nozzle 170 is therefore part of the microfluidic channel structure since the microfluidic channel 140 is formed therethrough and terminates at the nozzle opening.

The second face 130 is also not substantially planar but rather includes a second perimeter wall 132 that extends at least partially around a perimeter of the second face 130. The second face 130 does contain a floor 134 that is substantially planar. Between the second perimeter wall 132, one or more nozzle base sections 180 are formed with the number of nozzle base sections 180 being equal to the number of microfluidic channels 140. The nozzle base sections 180 are integrally formed with and extend outwardly from the floor 134 and in the illustrated embodiment, each nozzle base section 180 has a generally annular shape. However, the shape of the nozzle base section 180 is not limited to an annular shape and instead can have any number of shapes, including a conical shape or a tapered shape or any other regular or irregular shape. According to one embodiment, a plane that contains the upper edge of the second perimeter wall 132 generally cuts through the interface between the nozzle base section 180 and the nozzle 170. The nozzle 170 therefore extends beyond the upper edge of the second perimeter wall 132. According to one embodiment, the diameter of the reservoir 160 is about equal to the outside diameter of the nozzle base section 180; and therefore, an outside diameter of the reservoir wall 124 is greater than the outside diameter of the nozzle base section 180.

The specific configurations of the nozzle 170 and the microfluidic channel 140 are best shown in FIG. 5. As illustrated, the first end 142 of the microfluidic channel 140 is in the form of the reservoir 160. A distal end of the reservoir 160 has an inwardly tapered construction that leads to an intermediate channel section 146. A substantial length of the intermediate channel section 146 is formed in the nozzle base section 180. The intermediate channel section 146 also has a tapered construction in that it tapers inwardly toward the nozzle 170 defined at the second end 144 of the microfluidic channel 140. Thus, the dimensions of the microfluidic channel 140 are greatest at the first end 142 and are at a minimum at a tip portion 172 of the nozzle 170. In one embodiment, the microfluidic feature formed in the device 100 beginning with the reservoir 160 and terminating with the nozzle 170 is generally cylindrical in shape along its length. According to one exemplary embodiment, the open second end 144 of the microfluidic channel 140 formed at the tip portion 172 has an inside diameter equal to or less than 100 $\mu$m, preferably equal to or less than 50 $\mu$m and more preferably, equal to or less than 20 $\mu$m; and an outside diameter of the nozzle, as measured at a tip portion thereof, is less than about 150 $\mu$m and preferably is equal to or less than about 100 $\mu$m, and more preferably equal to or less than 50 $\mu$m. The inside diameter of the microfluidic channel 140 varies along its length due to its tapered construction. For example, the inside diameter of the microfluidic channel 140 opens gradually in a direction away from the nozzle 170 to about several hundred $\mu$m as the microfluidic channel 140 traverses through the thickness of the substrate body 110 and eventually, the microfluidic channel 140 is formed to a diameter of about 1.5 mm to define the reservoir 160. The length of the microfluidic channel 140 can be tailored in view of the construction details of the microfluidic device 100 and the potential applications of the device 100. In one example, the length of the microfluidic channel 140 is about 3 mm; however, this will vary depending upon the thickness of the device 100, the amount of sample that is to be loaded into the device, etc.

As with the first embodiment, the microfluidic channel 140 is formed in a substantially perpendicular manner in the substrate body 110 since the microfluidic channel 140 is formed substantially perpendicular to both the first and second faces 120, 130. While, the nozzle 170 extends beyond a plane containing the distal edge of the second perimeter wall 132, the distal end of the reservoir wall 124 preferably lies within the same plane that contains the distal edge of the first perimeter wall 122. This orientation permits a cover (e.g., thin polymeric cover sheet) or seal member to be disposed across the distal edge of the first perimeter wall 122 and the distal ends of the reservoir wall 124 to effectively seal the sample material within the reservoir 160, as will be described hereinafter.

One will appreciate that one of the advantages of the device 100 is that it is formed as a one piece construction in contrast to conventional devices which have multiple layers bonded together. In these conventional devices, the microfluidic channel is closed by the bonding of one layer over another layer. In other words, two separate layers are needed to define the complete channel. Because the present device 100 is injection-molded, separate bonded layers are not required.

It will be understood that the present configurations that are illustrated herein with reference to FIGS. 1–5 are merely exemplary in nature and are intended to merely convey exemplary embodiments. Various modifications can be performed to the microfluidic devices depending upon a number of different considerations, including manufacturing considerations. For example, the nozzle structures do not necessarily have to have conical shapes; however, for ease of manufacturing, a conical shape or the like is generally preferred.

According to another aspect of the present application, various manufacturing methods are disclosed herein for manufacturing the microfluidic array devices illustrated in FIGS. 1–5. In general terms, exemplary manufacturing processes disclosed herein permit microfluidic nozzle array devices to be manufactured having microscale nozzle dimensions (e.g., a nozzle tip opening having a diameter equal to or less than 100 μm, preferably equal to or less than 50 μm and more preferably, equal to or less than 20 μm; and an outside diameter of the nozzle, as measured at a tip portion thereof, is less than about 150 μm and preferably is equal to or less than about 100 μm, and more preferably equal to or less than 50 μm) and also the present microfluidic array devices are particularly suited to inexpensive fabrication methods. More specifically, the microfluidic array devices of the present application can be manufactured by injection molding a suitable thermoplastic using conventional injection molding techniques. Suitable thermoplastics include polycyclic olefin polyethylene copolymers, poly methyl methacrylate (PMMA), polycarbonate, polyalkanes, polyacrylate polybutanol co-polymers, polystyrenes, and polyionomers, such as Surlyn® and Bynel®. Polycyclic olefin polyethylene co-polymers are particularly suitable for use in an injection molding process. Various grades of such polymers are commercially available from Ticona under the trade name Topas® (which is a polyethylene-polycyclic olefin co-polymer). Furthermore, polybutyl terephthalate (PBT) can be used, as well as polyamides, such as nylons of different grades (nylon 6-6, nylon, 6 nylon 6-12, etc.); polyoxymethylene (POM) and other acetyl resins; and other resins with melt viscosity comparable to PBT and other properties similar to the other suitable polymers disclosed herein. Generally, polymers that are suitable for use in the present injection molding process include those thermoplastic polymers with a relatively low melt viscosity and these polymers preferably also have a high chemical purity (preferably the polymers are without more than a few percent of particulate additives and are chemically inert). Other suitable polymers include thermoplastics blended with a lubricant (e.g., liquid crystalline polymers) added to help the flow and therefore this additive acts as a processing aid and other liquid crystalline polymers containing polymers such as Zenite® (DuPont Company) and the like can be used and polymers (both commercially available and non-commercially available) that have high chemical purity, high chemical resistivity and thermal stability are also suitable. In some applications, injection-moldable elastomers may also be suitable.

In order to manufacture the present microfluidic array devices using injection molding techniques, a mold or mold insert must first be fabricated. The following description of the mold is merely exemplary for one type of mold construction which is oversimplified in terms of its construction in order to illustrate certain details of overall molding process. However, one of skill in the art will appreciate that the mold structure is readily changeable and is dictated by the desired construction of the microfluidic device and more particularly, the desired construction of the microfluidic channels based on the shape, dimensions and other properties thereof.

The mold typically is formed of several parts that mate with one another to form an assembled mold. The mold or mold insert is typically formed as a negative impression of whatever channel architecture or device features are desired in the microfluidic array device. A polymeric material is injected into the mold and then the polymeric material is cured to form the microfluidic array device which is then removed from the mold. Typically, the mold is formed of two mold dies that mate together in a sealed manner and therefore after the microfluidic device has been formed and is sufficiently cooled, the two mold dies are separated to permit access and removal of the microfluidic array device.

The mold (i.e., mold dies) or mold insert can be prepared from any number of materials that are suitable for such use, such as metal, silicon, quartz, sapphire and suitable polymeric materials; and forming the negative impression of the channel architecture can be achieved by techniques, such as photolithographic etching, stereolithographic etching, chemical etching, reactive ion etching, laser machining, rapid prototyping, ink-jet printing and electroformation. With electroformation, the mold or mold insert is formed as a negative impression of the channel architecture by electroforming metal and the metal mold is polished (preferably to a mirror finish).

For non-metallic molds for injection molding, the mold can be made of a flat, hard material such as Si wafers, glass wafers, quartz or sapphire. The microfluidic design features can be formed in the mold through photolithography, chemical etching, reactive ion etching or laser machining (which is commonly used in microfabrication facilities). In addition, some ceramics can be used to fabricate the mold or mold insert.

Molds can also be fabricated from a "rapid prototyping" technique involving conventional inkjet printing of the design or direct lithography of resists, such as Su-8 or direct fabrication of the mold with photopolymers using stereolithography, direct 3-dimensional fabrication using polymers, and other similar or related techniques that use a variety of materials with polymers. A resulting polymer-based mold can be electroformed to obtain a metallic negative replica of the polymer-based mold. Metallic molds are particularly appropriate for injection molding of polymers that require the mold itself to be heated. One commonly used metal for electroforming is nickel, although other metals can also be used. The metallic electroformed mold is preferably polished to a high degree of finish or "mirror" finish before use as the mold for injection mold. This finish is comparable to the finish obtained with mechanical polishing of submicron to micron size abrasives (e.g., diamond particles). Electropolishing and other forms of polishing can also be used to obtain the same degree of finish. Additionally, the metallic mold surface should preferably be as planar and as parallel as the Si, glass, quartz, or sapphire wafers. In one exemplary embodiment, the metallic mold is polished to a highly polished finish by using 1 micron diamond particles to provide a finish that is close to a mirror-like finish.

Figure 6:
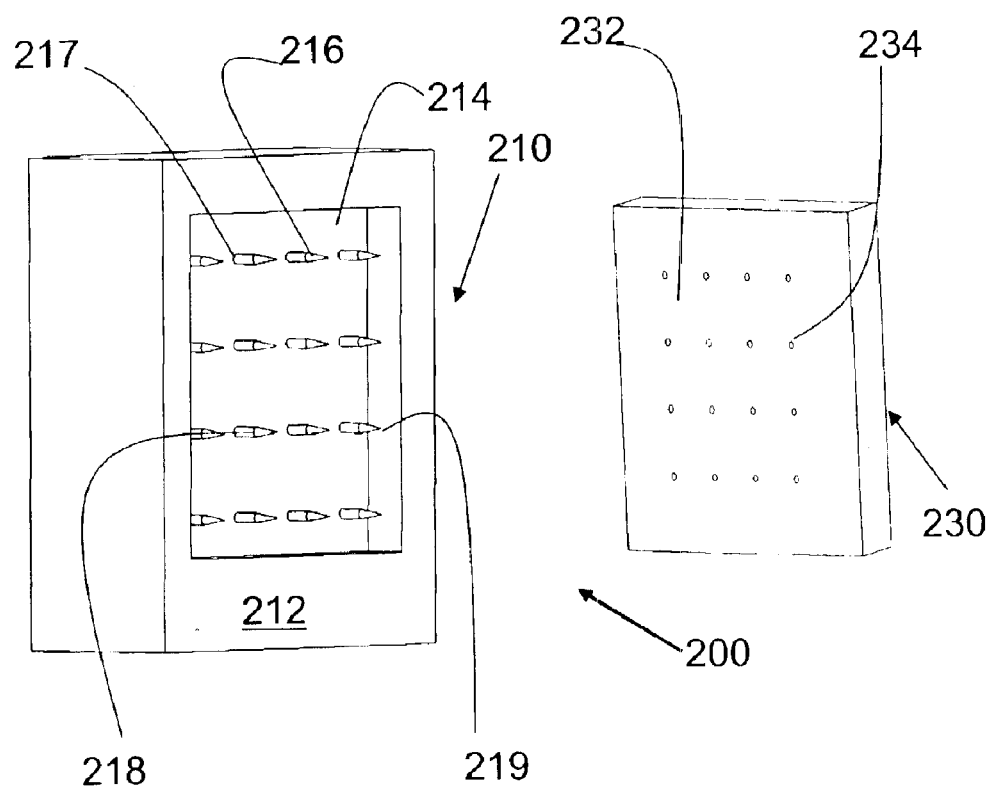
FIG. 6 is a perspective view of an exemplary mold used to manufacture the microfluidic device of FIG. 1.

The present applicant has discovered that injection molding techniques using a mold fabricated of hardened steel or other metals can be used to manufacture polymeric microfluidic devices having an array of micron sized nozzle structures with a nozzle opening having a diameter equal to or less than 100 μm, preferably equal to or less than 50 μm and more preferably, equal to or less than 20 μm; and an outside diameter of the nozzle, as measured at a tip portion thereof, is less than about 150 μm and preferably is equal to or less than about 100 μm, and more preferably equal to or less than 50 μm. FIG. 6 is a perspective view of a mold construction 200 that is constructed to injection mold a microfluidic nozzle array device, as shown in FIG. 1, having the aforementioned dimensions and properties. Once again, the mold 200 is formed as a negative impression of the microfluidic device that is to be formed. The mold 200 includes a first mold die or part 210 and a second mold die or part 230 that are constructed so that they are complementary to one another and mate with one another to form an injection mold assembly that is used to form a microfluidic nozzle array device, similar to device 10 illustrated in FIG. 1. The mold 200 is preferably formed by electric discharge machining (EDM).

The first mold die 210 has a first face 212 that includes a substantially planar surface. The first face 212 has a recessed section 214 formed therein. The recessed section 214 generally defines the outer peripheral shape of the microfluidic device and also the depth of the recessed section 214 defines the thickness of the microfluidic device (except in areas where the nozzles are formed). Because the microfluidic device typically has a square or rectangular shape, the shape of the recessed section 214 will be the same or similar. For example, the illustrated recessed section 214 is generally square shaped. The first mold die 210 also includes a plurality of upstanding contoured pins 216 that are spaced across a floor of the recessed section 214. The shape of each pin 216 directly corresponds to the shape of the microfluidic channel that will be formed when the mold 200 is closed and the polymeric material is injected. More specifically, a base section 217 of the pin 216 corresponds to the reservoir of the microfluidic channel; an intermediate section 218 corresponds to the intermediate section of the microfluidic channel and a conical tip section 219 of the pin 216 corresponds to the second end of the microfluidic channel that is formed in the tip portion of the nozzle. As a result, the dimensions of the pin 216 are greatest at the base section 217 and the pin 216 tapers inwardly to the conical tip section 219 thereof. The spacing of the pins 216 directly correlates to the spacing of the microfluidic channel/nozzle structure and therefore, the pins 216 are preferably spaced in arrays.

Figure 7:
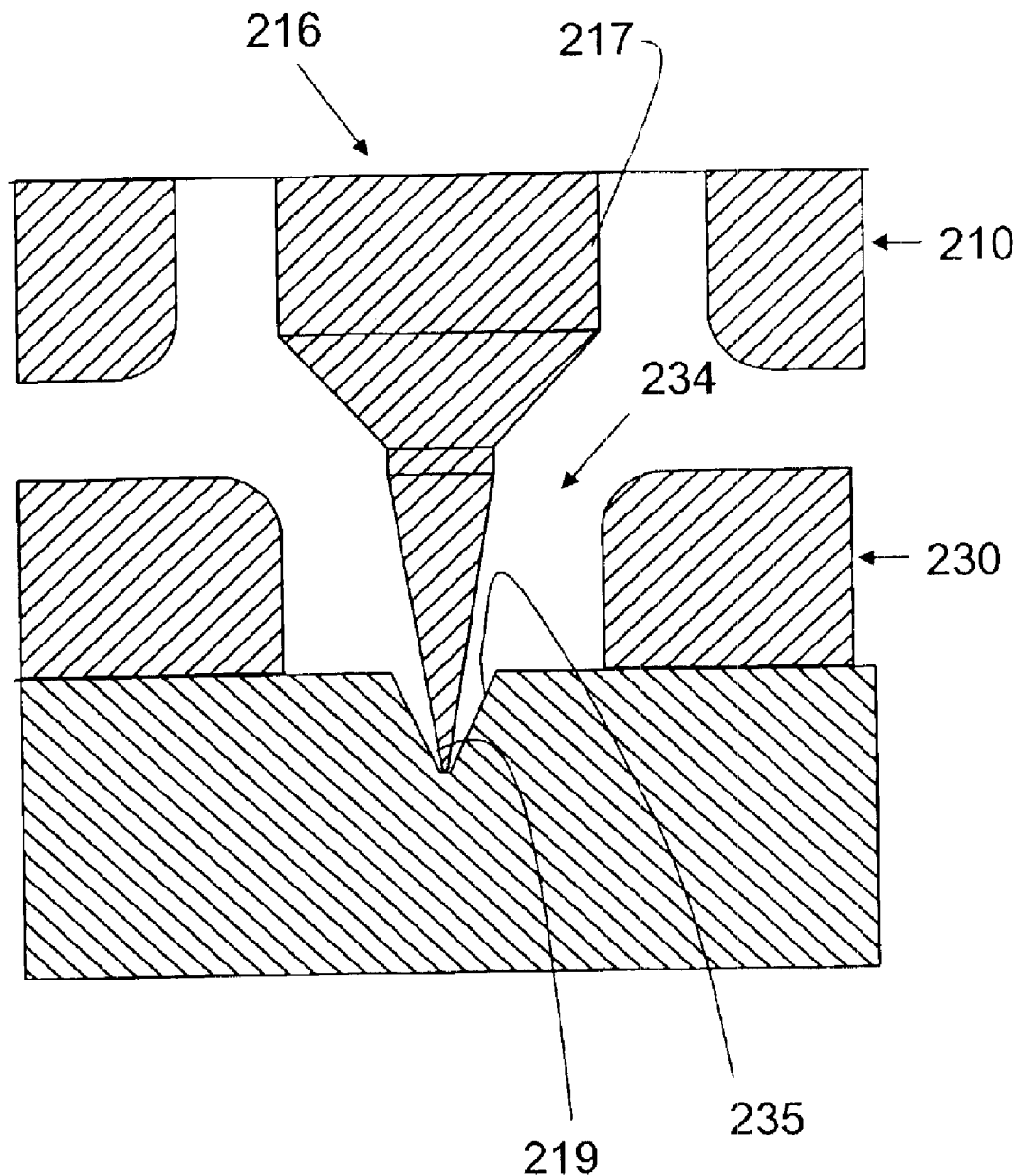
FIG. 7 is a cross-sectional view of first and second dies in a closed position that is used to manufacture the microfluidic device of FIG. 4.

Now referring to FIGS. 6–7, the second mold die 230 has a first face 232 that mates with the first face 212 of the first mold die 210. The first face 232 is substantially planar with the exception that a plurality of apertures 234 are formed in the second mold die 230. The apertures 234 are arranged according to a predetermined pattern that corresponds to the arrangement of the pins 216. The apertures 234 are sized so that they receive at least a portion of the conical tip sections 219 (about 500 $\mu$m in length in one embodiment) of the pins 216 when the first and second mold dies 210, 230 mate with one another. The apertures 234 are themselves contoured so that the apertures 234 taper inwardly with a lower portion 235 of each aperture 234 having a conical shape so as to form the conical nozzle of the microfluidic device. When the first and second molds 210, 230 mate together and the pins 216 are received in the apertures 234 according to one embodiment, the tip sections 219 of the pins 216 extend completely to the bottom of the apertures 234 and contact the body of the second die mold 210 that defines the closed ends of the apertures 234. The mold 200 of FIG. 6 is constructed to generally produce the microfluidic device 10 of FIG. 1.

FIG. 7 shows a cross-sectional view of a mold that is constructed to produce the microfluidic device 100 of FIG. 4. For purposes of ease of illustration and simplification, the reference numbers of FIG. 6 will be carried over to the description of FIGS. 7–9 since each of these illustrated molds includes first and second mold dies. It will be understood that the features that are formed as part of the first and second mold dies 210, 230 dictate the dimensions and shape of the features of the resulting microfluidic device.

It will therefore be appreciated that after the first and second mold dies 210, 230 are closed and any preparation steps that are necessary for the injection molding process are taken, the first faces of the first mold die 210 and the second mold die 220 seat against one another to effectively seal the recessed section 214 and the polymeric material (typically a resin) is then injected into the closed space that is defined in part by the recessed section 234. FIG. 7 shows a cross-sectional view of the first and second mold dies 210, 230 in a closed position with the tip section 219 of one pin 216 received within the aperture 234 and more specifically into the conically shaped lower portion 235 of the aperture 234. Because the first and second mold dies 210, 230 are negative impressions of the resultant microfluidic device, the microfluidic channel will take the form of the pin 216 and the nozzle of the microfluidic device is formed by the conically shaped lower portion 235. More precisely, the nozzle is formed by resin filling completely the space between the tip section 219 of pin 216 and the tip section of the conically shaped lower portion 235. As previously mentioned, in this embodiment, the tip section 219 of the pin 216 and the tip of the second mold die 230 that is formed in the conically lower shaped portion 235 are in contact with one another.

Mold 200 is intended to be used a number of times over a period of time to produce a great number of microfluidic devices and therefore the material that is selected for the fabrication of the mold 200 should be done so accordingly. In other words, a material should be selected that permits microscale features to be formed in the microfluidic device and also permits a great number of microfluidic devices to be formed using the mold 200. One material that is suitable for use in fabricating the mold 200 is hardened steel. With conventional machining technologies, such as metal turning and electric discharge machining (EDM), the dimensions of the tip section 219 of the pin 216, which forms the nozzle opening, can be limited. For example, the dimensions (i.e., the diameter and length) of the tip section 219 can be limited due to manufacturing considerations. The available manufacturing techniques permit the outside diameter of the nozzle to be formed to about 50 $\mu$m since it is possible to inject mold a resin into the space between the tip section 219 and the conically lower shaped portion 235. In some areas, this space is only on the order of about 15 $\mu$m due to the desired dimensions of the nozzle and the microfluidic channel.

While, the first mold die 210 is illustrated as having a square shape, it will be appreciated that the first mold die 210 can be formed to have any number of different shapes so long as the shapes of the first mold die 210 and the second mold die 230 permit these two components to mate with one another.

Figure 8:
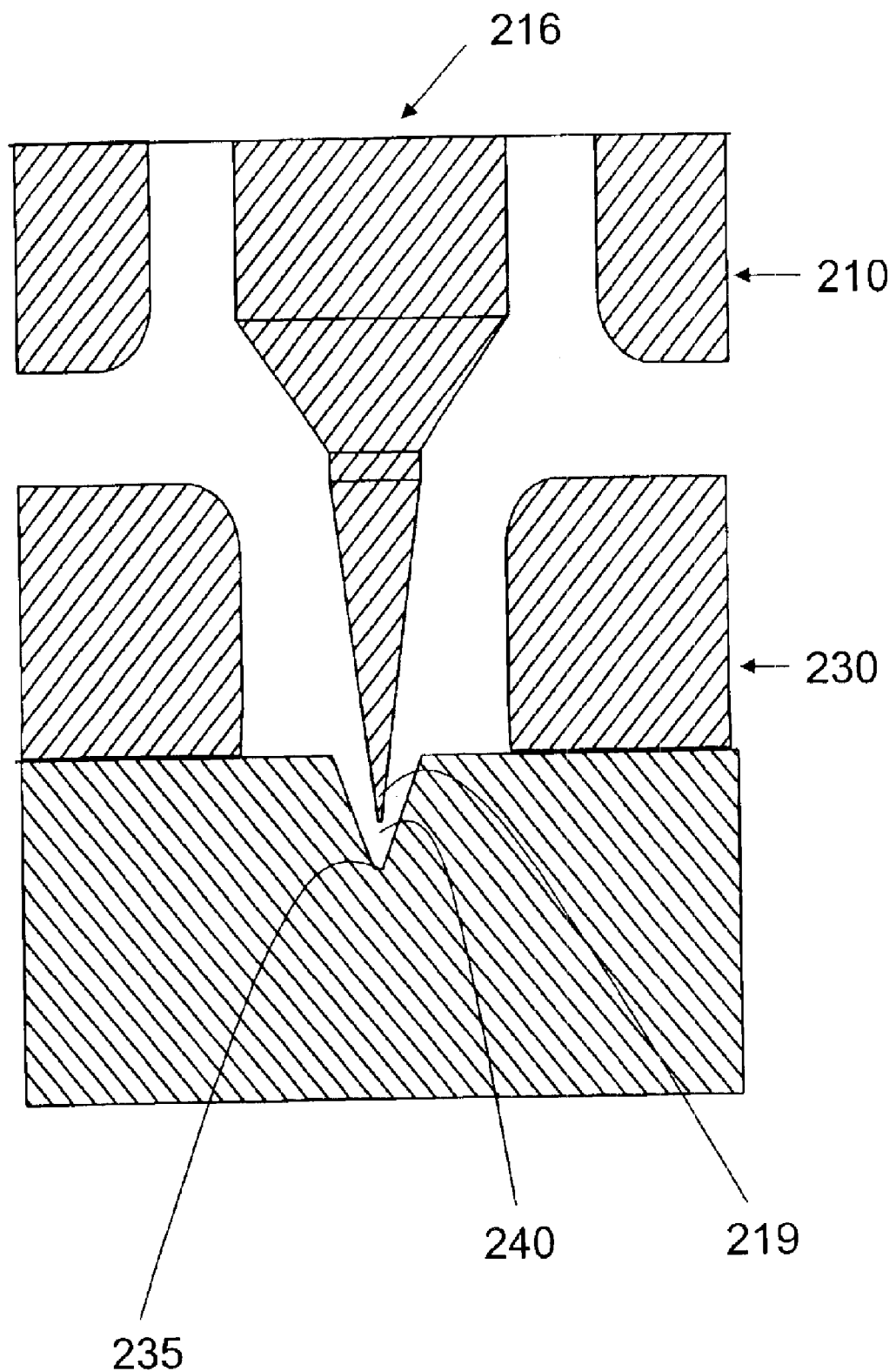
FIG. 8 is a cross-sectional view of first and second dies of the mold illustrating another embodiment where a gap is formed between a pin of the first mold and a nozzle forming feature of the second mold.

However, there are techniques available to injection mold a nozzle opening having smaller dimensions than the aforementioned dimensions. FIG. 8 illustrates one possible injection molding arrangement to accomplish this task and produce nozzles having nozzle openings that are even smaller than the tip section 219 of the pin 216. In FIG. 8, there is a gap 240 between the tip section 219 and the conically shaped lower portion 235 after the first and second mold dies 210, 230 have been assembled. When the polymeric material (e.g., a resin) is injected (in a molten state) into the conically shaped lower portion 235, the pressure of the injected resin is adjusted such that the resin does not fill the entire space in the gap 240 and an opening (space) remains at the tip of the resulting molded nozzle since sufficient pressure is not present to displace the resin to the lowermost section of portion 235. Using this technique, the diameter of the tip section 219 of the pin 216 can be greater than 20 $\mu$m since the opening of the nozzle and the outside diameter of the nozzle are no longer defined by the dimensions of the corresponding parts of mold but rather are defined by a combination of mold dimensions, gap dimension and injection pressure. In this manner, the pins 216 do not have to be manufactured to have a tip section 219 on the order of 20 μm in order to form a nozzle opening of the same dimension. Instead, the tip section 219 can have a diameter greater than the diameter of the nozzle opening that is ultimately formed in the nozzle as a result of the injection molding process.

Figure 9:
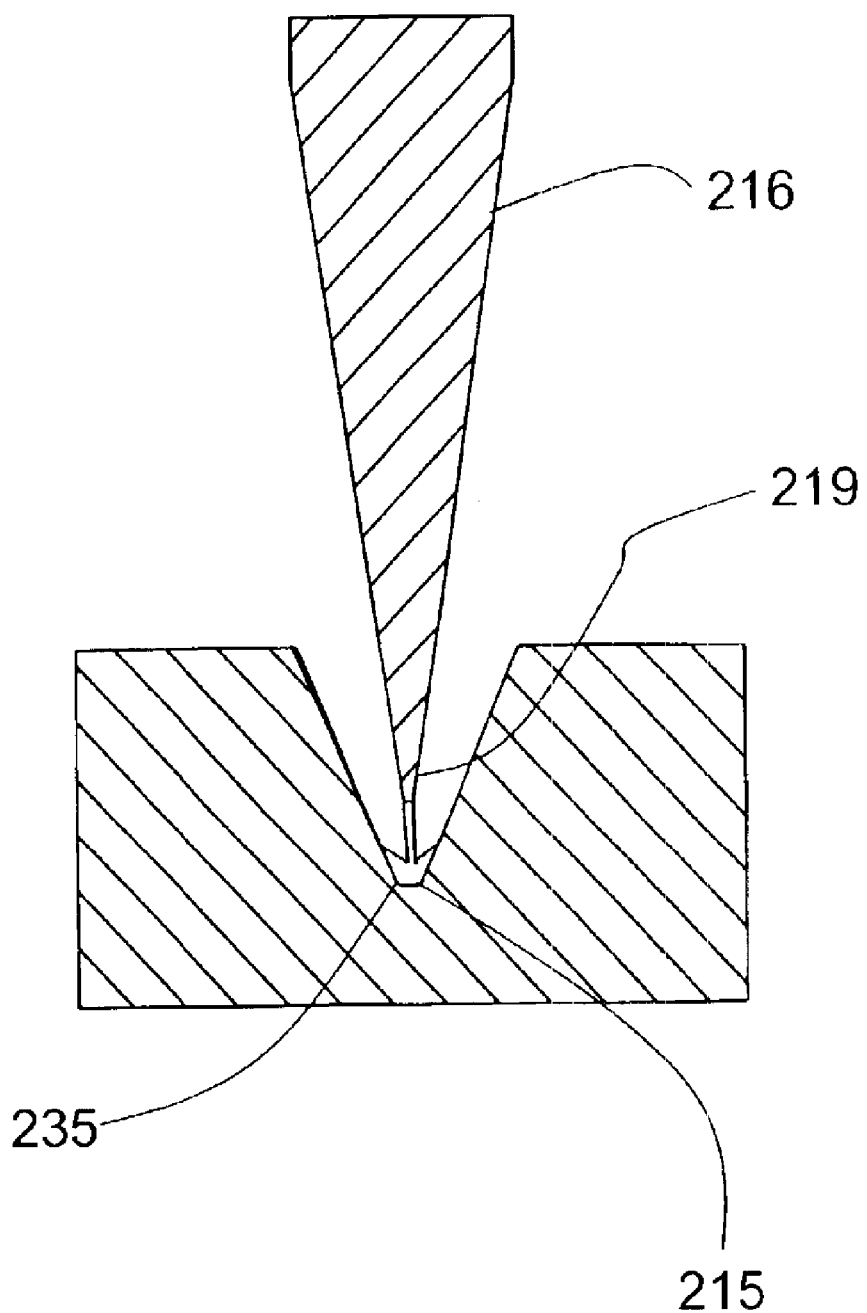
FIG. 9 is a cross-sectional view illustrating a mold arrangement for fabricating a micron sized nozzle opening.

FIG. 9 illustrates one exemplary method of overshooting the injected resin into the gap 240 formed between the tip section 219 and the tip of the conically shaped lower portion 235. The nozzle opening 215 is defined by pressure used to inject the molten resin and the dimensions of the gap 240. By controlling these parameters, the dimensions of the nozzle opening can be controlled.

Injection molding as a manufacturing technology for polymer parts is low-cost at high-volume production. However, there is considerable cost involved in the production of the mold itself, especially for a microfluidic nozzle design which has micron sized features and therefore is a demanding design in terms of producing a mold. If the microfluidic nozzle array device is arranged to have the same pattern as the microtiter plate so that commercial robotic liquid dispensing equipment can be used to fill the reservoirs of the microfluidic channels with samples, then tiling or combining a number of smaller microfluidic nozzle array devices (i.e., subunits) to form a larger structure can be used since the microtiter plates consist of regularly spaced sample input points in a grid pattern. For example, the microfluidic nozzle array devices can be formed and then combined with one another to produce a structure that has the desired number of sample reservoirs (also referred to as sample wells or sample inputs) to receive a desired number of samples. For example, some common microfluidic devices contain 96 sample reservoirs (8×12 grid); 384 sample reservoirs (16×24 grid); and 1536 sample reservoirs (32×48 grid). The tiling can be done by number of known conventional means, including by permanently bonding adjacent tiles together by melt bonding, welding, gluing, etc. In other words, any suitable method or technique for joining polymer structures together can be used. The subunit structures can be formed as individual subunit tiles (see FIGS. 17–18) or the subunit structure can be in the form of an elongated strip that includes a number of rows of nozzles. For example, the strip can be formed to include 2 rows of spaced apart nozzles.

Figure 17:
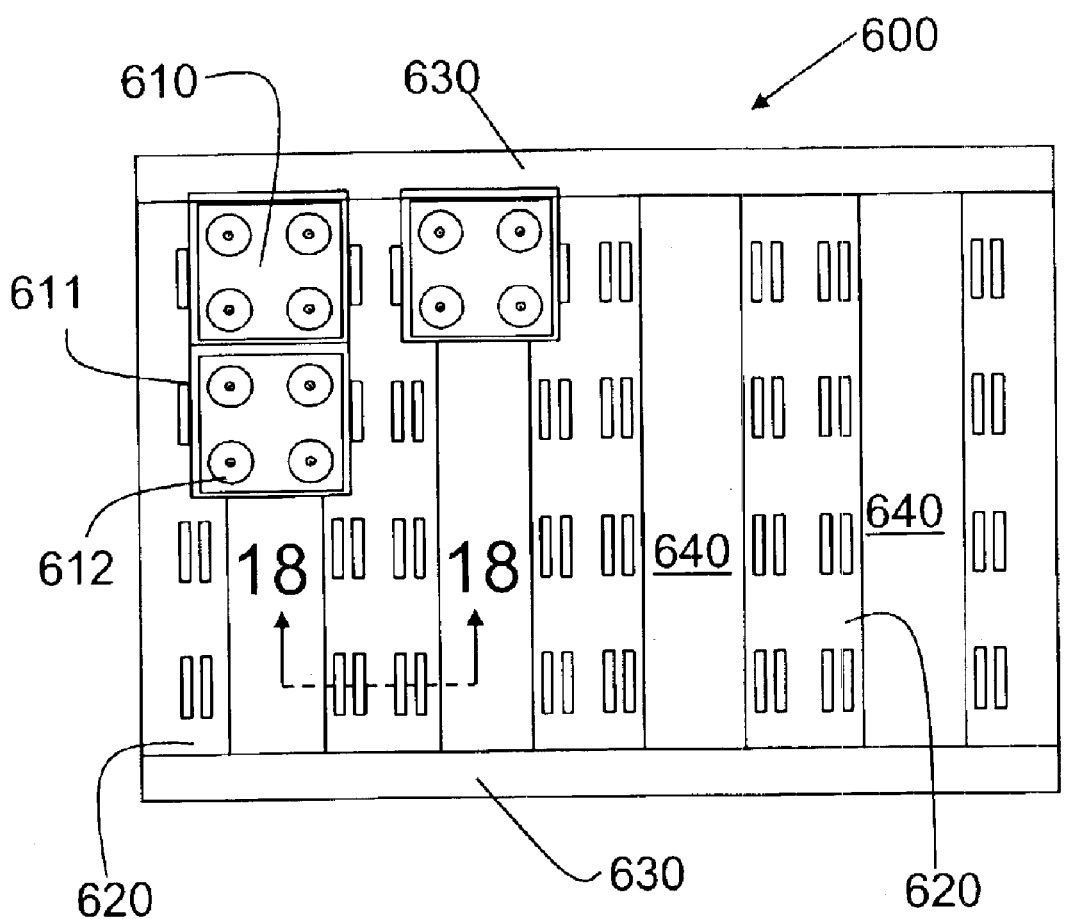
FIG. 17 is a top plan view of a retaining base for releasably holding a number of microfluidic nozzle subunit structures.

Alternatively, the user can be supplied with a base plate that has a number of features formed therein to permit nozzle subunit structures to be inserted into and retained by the base plate. For example, the base plate can contain pre-defined receptacles that receive the nozzle subunit structures in such a way that the nozzle subunit structures are securely held within the base plate and are arranged according to a desired pattern. One or both of the base plate and the nozzle subunit structures can contain interlocking features to provide an interlocking connection between the base plate and the nozzle subunit structures. In this embodiment, the base plate functions as a base on which the final microfluidic nozzle array device can be constructed by arranging a number of nozzle subunit structures together and then securely holding these subunit structures within the base plate. One exemplary structure for releasably holding the nozzle subunits in an interlocked manner is illustrated in FIG. 17 and is discussed in greater detail hereinafter in the discussion of Example 3.

There are a number of advantages that are obtained by tiling or otherwise combining a number of nozzle subunit structures into a microfluidic nozzle array device of greater dimension. First, the cost of manufacturing the mold for the smaller nozzle subunit structure is substantially less than the cost of manufacturing a mold for the entire grid of the microfluidic nozzle. Also, the cost of mold replacement is also substantially reduced in the case that only one pin in the mold is damaged. Second, the utility of the nozzle array is made more flexible. If an experiment does not require all of the reservoirs (e.g., 96) of the microfluidic device to be filled, only the needed number of nozzles or a number close thereto can be inserted into the base plate. At the same time, this construction still permits robotic dispensing of samples. For example and according to one exemplary embodiment, one nozzle subunit structure contains 4 reservoirs and therefore, if the experiment only requires 60 reservoirs, then only 15 nozzle subunit structures are inserted into the base plate. In this manner, the potential waste or inefficiency related to each microfluidic device is eliminated or greatly reduced because the number of unused reservoirs is greatly reduced or entirely eliminated.

Figure 10:
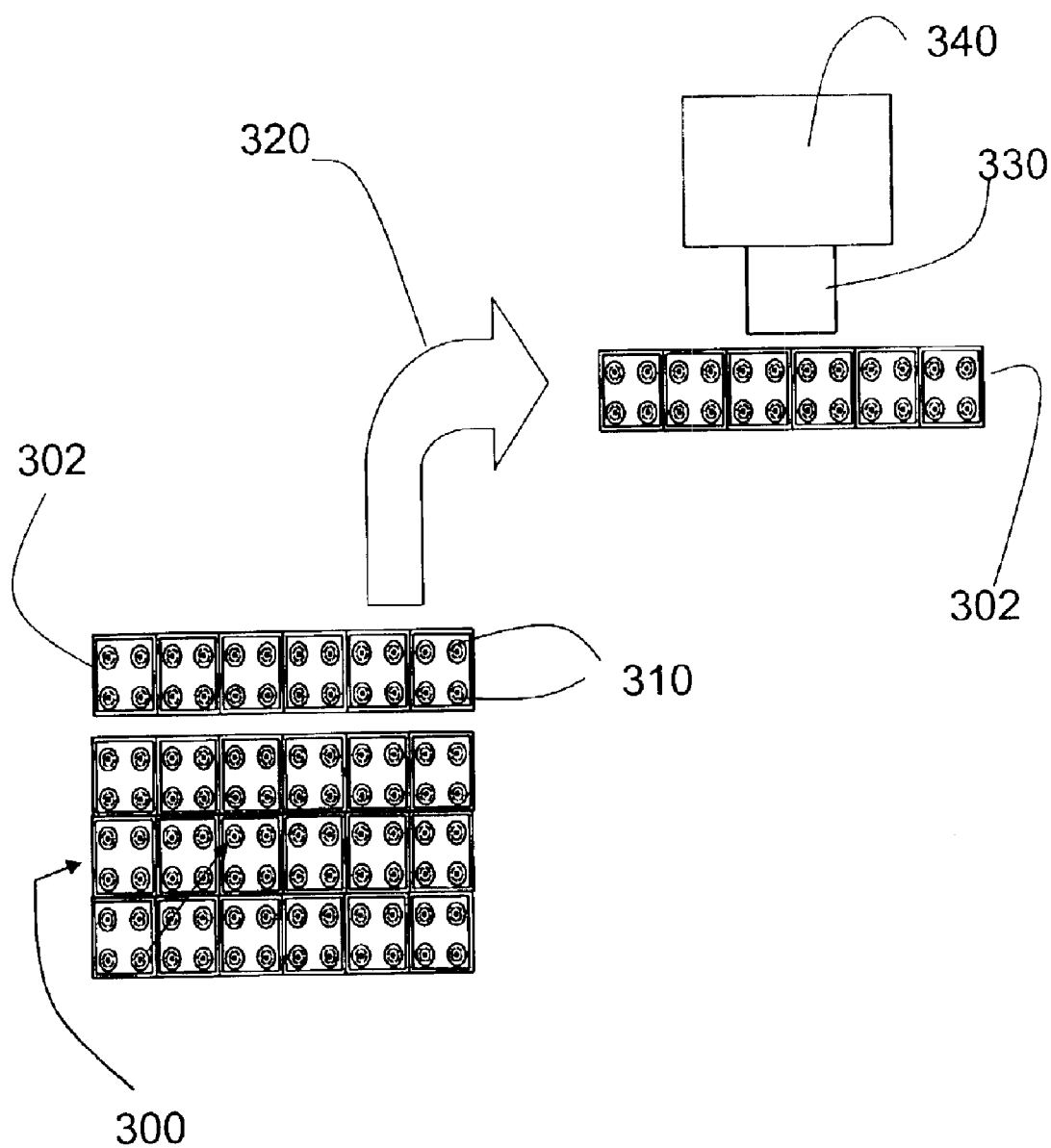
FIG. 10 is a top plan view of a tile arrangement formed of a number of strips connected to one another with each strip including a nozzle array, wherein one of the strips is removed and placed in close proximity to a mass spectrometer.

Third, when the microfluidic nozzle array device is used for electrospray or nanospray in front of a mass spectrometer inlet, a common configuration is to have the nozzle spray "off-axis", i.e., the nozzle sprays in a direction perpendicular to the inlet. Since the nozzle has to be placed in close proximity to the inlet (e.g., typically within an inch), there is often times not enough room in front of the inlet to accommodate the entire microtiter plate. FIG. 10 illustrates how a tiled microfluidic nozzle array microtiter plate can be used for electrospray in the off-axis configuration. A tiled microfluidic nozzle array 300 arranged in a 96 well microtiter plate format is broken up into strips 302 with two rows of 12 nozzles 310 each. One of the strips 302 is broken away or is otherwise removed from the others and is transferred (as indicated by arrow 320) to a nozzle mount (not shown) in front of a mass spectrometer inlet 330 of a mass spectrometer 340. The nozzle mount holds the strip 302 and has at least an x-y translation stage such that each of the nozzles can be placed in an optimal position with respect to the mass spectrometer inlet 330 for spraying of the sample material that is contained within the microfluidic channel associated with the selected nozzle. The direction of the spray is perpendicular to the mass spectrometer inlet 330. In schematic drawing of FIG. 10, the nozzles 310 are positioned below the centerline of the mass spectrometer inlet 330 and the spray is in the direction out of the surface of the drawing figure. It will be appreciated that the strips 302 that are still in tact can be used in future applications either by using the entire structure of joined strips 302 or by detaching one or more strips 302 for use in a given application depending upon the precise application and what the requirements for the application are in terms of the number of nozzles 310 that is needed.

The microfluidic nozzle array devices disclosed herein are suitable for use in a number of different types of applications.

For purposes of illustration only, some of the exemplary applications will be disclosed with reference to the microfluidic nozzle array device 100 illustrated in FIGS. 4–5; however, it will be understood that any of the devices disclosed herein can be used in place of device 100.

The microfluidic nozzle array device 100 is particularly suited for use in nanospray/electrospray applications. Electrospray is the technique that enables a liquid sample to be vaporized and ionized for mass spectrometry analysis. The electrospray process takes place in ambient pressure. Conventional electrospray utilizes a capillary with a relatively large inside diameter (i.e., about 50 μm) to deliver the liquid sample to the entrance of the mass spectrometer. The liquid that is flowing out of the capillary is vaporized under the influence of an electric field generated by placing a high voltage (e.g., 4–5 KV) on a metallic conductor close to the capillary opening and a ground plane opposite the capillary opening, or vice versa. Dry nitrogen flows through concentric tubing to the capillary to help nebulize the liquid flowing out of the capillary. The flow of the liquid inside the capillary is driven generally by a pump, such as a syringe pump.

Figure 11:
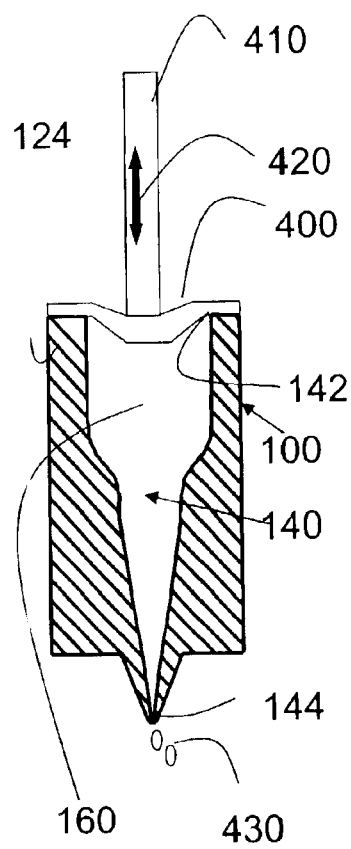
FIG. 11 is a cross-sectional view of one microfluidic channel/nozzle arrangement wherein a sample reservoir is sealed by a member having a polymeric cover sheet which is insertable and movable within the reservoir for discharging the sample through a nozzle opening.
Figure 12:
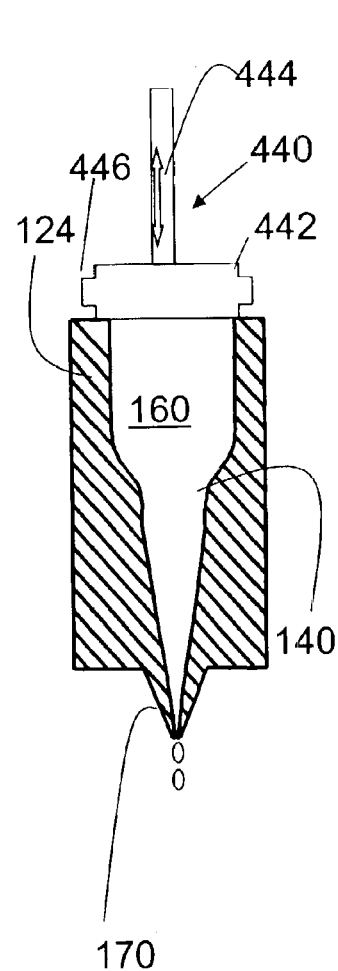
FIG. 12 is a cross-sectional view of one microfluidic channel/nozzle arrangement wherein a sample reservoir is sealed by a member having an elastic sealing base which is insertable and movable within the reservoir for discharging the sample through a nozzle opening.
Figure 13:
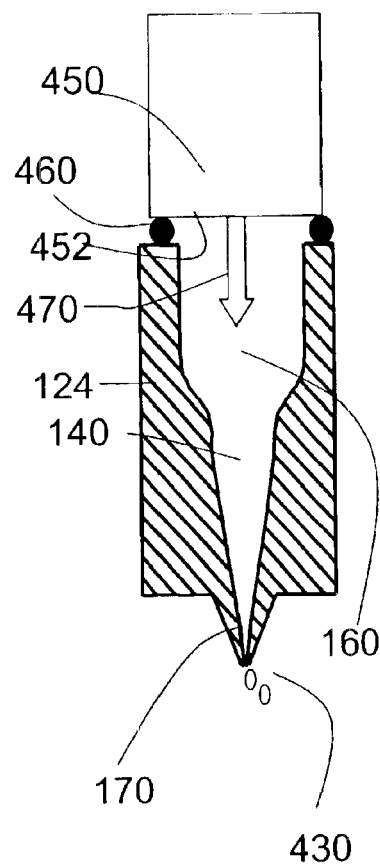
FIG. 13 is a cross-sectional view of one microfluidic channel/nozzle arrangement where a sample reservoir is sealed by a piston device having a bore extending therethrough for injecting a fluid into the sample reservoir to cause the sample to be discharged through a nozzle opening.

For the nozzle array of the present microfluidic device 100 to be used as individual nanospray sources, the reservoir 160 on the opposite side of the nozzle opening is filled with a sample to be sprayed. Before the spray, the reservoir has to be sealed so that the reservoir is liquid tight. In other words, the open end of reservoir 160 (i.e., the open first end 142 of the microfluidic channel 140) must be sealed. The sealing of the open end of the reservoir 160 can be accomplished in a number of different ways that each provides a satisfactory liquid tight seal of the reservoir and permits the sample to be transported within the channel 140. FIGS. 11–13, illustrate a number of exemplary ways to provide the desired liquid tight seal of the reservoir.

For example, FIG. 11 illustrates a first sealing technique in which the opening of the reservoir 160 (i.e., the first end 142 of the microfluidic channel 140) is sealed with an elastic cover sheet 400. The elastic cover sheet 400 is preferably in the form of an elastic polymeric cover sheet. In the microfluidic nozzle array device 100, the polymeric cover sheet 400 is coupled to the reservoir wall 124 so that the polymeric cover sheet 400 extends completely across the open end of the reservoir 160. A mechanical plunger 410 or the like can be used to apply a force to the polymeric cover sheet 400 to force the sample along the length of the microfluidic channel 140 and ultimately out of the nozzle opening (second end 144 of the microfluidic channel 140) in a continuous stream, generally indicated at 430. The discharged continuous liquid stream of the sample is then vaporized under the influence of an electric field. The general direction of movement of the polymeric cover sheet 400 and the plunger 410 is illustrate by arrow 420.

Another sealing technique is illustrated in FIG. 12. According to this technique, a movable sealing member 400 is provided and is formed of a sealing base 422 for sealing the opening of the reservoir and a rod or plunger 444 that is attached to the sealing base 442. The dimensions of the sealing base 442 are greater than the dimensions of the open end of the reservoir 160 and therefore, the sealing base 442 seats against the reservoir wall 124 and completely extends across the open end of the reservoir 160. The sealing base 442 is formed of a suitable elastic material to permit the sealing base to locally deform when a force is applied thereto. This elasticity permits the sealing base 442 to act as a temporary diaphragm that seals the reservoir as the sealing base 442 is directed into the reservoir 160 itself.

When the sealing base 442 is pushed downward in the direction toward the nozzle 170, the sealing base 442 deforms as it is forced into the first end of the microfluidic channel 140 (which is also the entrance to the reservoir 160). In the illustrated embodiment, the sealing base 442 includes a flange 446 that has a greater diameter than the diameter of the other portions of the sealing base and therefore, when the sealing base is inserted into the reservoir, the flange 446 intimately contacts the inner surface of the reservoir wall 124 and forms the liquid tight seal between the sealing base and the reservoir. As the sealing base 442 is inserted into the reservoir 160 and travels therein toward the nozzle, the sealing base 442 effectively forces the sample toward the second end 144 of the microfluidic channel 140, causing the sample to be discharged through the nozzle opening defined thereat. There may be an air gap between the sample (e.g., a liquid) in the reservoir 160 and the sealing base 442 or a vent (not shown) can be incorporated into the sealing base 442 for air to be pushed out of the reservoir 160 when the sample is forced through the microfluidic device by the sealing base 442. The vent can be fabricated using conventional vent technology in that the vent should permit air passage, while being impermeable to the flow of liquid so that the sample is prevented from flowing through the vent and out of the reservoir 160.

It will be appreciated that the plunger 444 can either be manually operated or it can be part of an automated system including an actuator or the like which controls the movement of the plunger 444. All of the plungers 444 can be linked to a common actuator or the link so that upon activation, the plungers 444 are all driven at the same time, resulting in the samples being concurrently transported through respective channels to respective nozzles.

Yet another sealing technique is illustrated with reference to FIG. 13 in which a fluid carrying member 450 is provided. The member 450 has a hollow portion and is generally shaped to be complementary to the shape of the reservoir 160 to permit the member 450 to seat against the upper edge of the reservoir wall 124. The member 450 includes a distal end 452 which initially is positioned proximate to the open end of the reservoir 160. At the distal end 452, a gasket 460 is provided and in the illustrated embodiment, the gasket 460 is in the form of a sealing O-ring or the like. The gasket 460 serves to provide a seal between the distal end 452 and the reservoir wall 124 to prevent from escaping between this interface when the sample is transported in the following manner. Because the member 450 is at least partially hollow, the gasket 460 is disposed around the bore that extends through the member 450.

In this embodiment, the sample is moved within the microfluidic channel 140 by conducting a fluid through the member 450 (more specifically, the bore thereof) to effectively force the sample through the microfluidic channel 140 to the nozzle 170 where the sample is discharged in continuous stream 430. The fluid is preferably a high-pressure gas, such as air or dry nitrogen gas that is delivered from a source that is in fluid communication with the piston bore. The flow direction of the fluid is generally indicated at 470. In another embodiment, the fluid can be the liquid sample fed into the microfluidic channel 140 to continuously push liquid out through the nozzle.

It will be appreciated that a protective cover (not shown) can be placed at the distal end 452 of the fluid carrying member 450 to prevent sample from contacting the inner surfaces of the piston bore. The protective cover must be permeable to the fluid that flows through the bore and into the reservoir 160 to transport the sample along the microfluidic channel 140. For example, the protective cover can be in the formed of a thin polymeric film that is gas permeable, while at the same time being impermeable to liquid flow. In this manner, the sample can not contact the bore itself. The use of such a protective cover is not required since the injected fluid that flows through the member 450 can push the liquid sample out by applying a force to the air gap between the sample and the surrounding structure.

A more conventional fluid delivery mechanism can be used with the device 100. In this embodiment, a stopper is inserted into the reservoir 160, with the stopper having a bore formed therethrough which is in communication with the reservoir 160. A capillary is inserted through the bore and the liquid sample is injected into the reservoir through the capillary from a source external to the capillary. In this embodiment, the sample is not stored in the reservoir 160 but rather is delivered to the channel 140 by being injected into the reservoir 160 through the capillary.

As previously mentioned, the front face of the nozzle array is made electrically conducting by a thin film of metal or conducting polymer. When an electric field of appropriate strength is applied to the nozzle (e.g., as by the arrangement illustrated in FIG. 3), the liquid and the analytes it carries (i.e., the sample) are vaporized as they are discharged through the nozzle opening. Liquids that are suitable for use in electrospray mass spectrometry analysis include but are not limited to acetonitrile, methanol, ammonium acetate, and other volatile liquids. Since the inside diameter of the nozzle is less than about 20 μm, the amount of material flowing out of the nozzle to be vaporized is less than the amount that is typically used in a conventional electrospray operation. Also, the outside of 50 μm creates a strong enough electric field for vaporization with applied voltage below about 6 KV.

Figure 14:
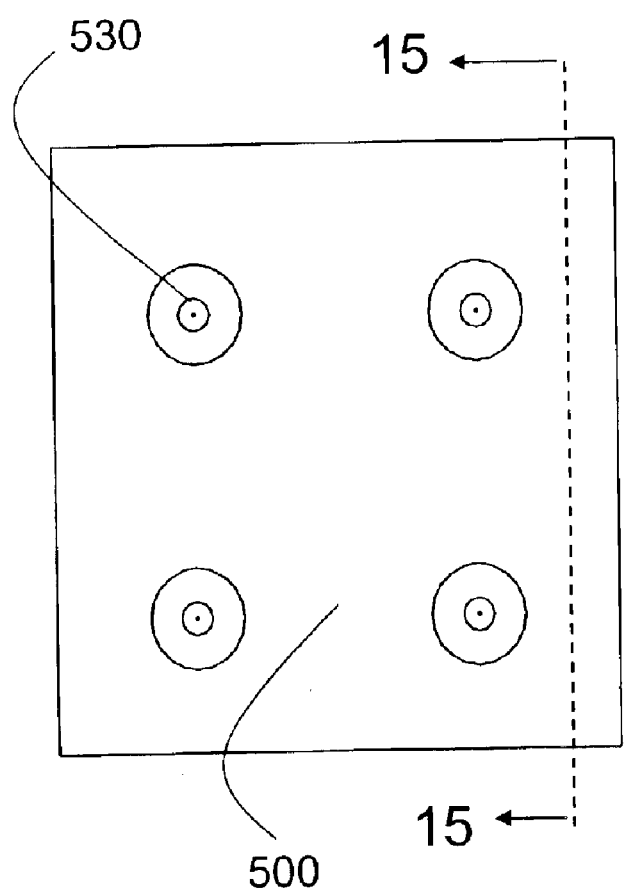
FIG. 14 is a top plan view of an exemplary microfluidic nozzle array device.
Figure 15:
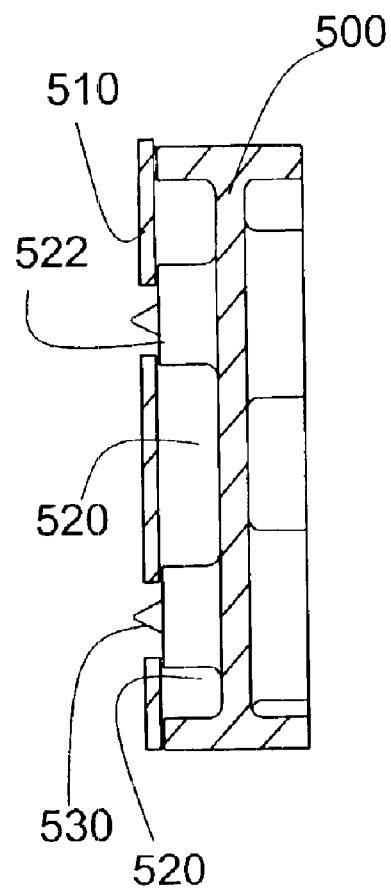
FIG. 15 is a cross-sectional view taken along the line 14—14.

The use of a nebulizing gas to assist in the vaporization process is therefore not needed; however, if nebulizing gas is needed, channels conducting dry nitrogen gas to the nozzle opening may be easily added in a polymer substrate attached to the front of the nozzle array. FIGS. 14–15 are a top plan view and a cross-sectional view, respectively, of a microfluidic nozzle array device 500 in combination with a substrate 510 having gas conduits 520 formed therein for nebulization. The microfluidic nozzle array device 500 can be similar to or identical to any of the exemplary microfluidic array devices disclosed hereinbefore. A gas outlet 522 is formed such that it is concentric with one nozzle 530. The substrate 510 with the nebulizing gas channels can be fabricated by an injection molding process during the injection molding process that is used to the nozzle array device 500 itself or it can be fabricated first and then later attached to (e.g., bonded) the nozzle array device 500 as a separate component. The substrate 510 can be attached in any number of different ways including but not limited to using an adhesive or meltingly bonding the two members along a boundary zone.

In some instances, it may not be necessary to have the nozzle array conform to the microtiter plate sample well format. For example, the sample can be fed to the nozzle by the elutant of a high performance liquid phase gas chromatography (HPLC) column. Since the reservoir size in the nozzle array can be formed to arbitrary sizes, it can be formed so that the open end of the reservoir can receive one end of the HPLC column or any plumbing for splitting the HPLC elutant for mass spectrometry analysis. The reservoir side of the nozzle array can also consist of injection molded features for splitting elutant for mass spectrometry analysis. The driving force for the liquid sample analytes to flow through the nozzle opening in this case is the pressure-driven liquid flow of the HPLC. Neither a pressure diaphragm nor an external pressure-inducing mechanism is needed.

The microfluidic nozzle array devices disclosed herein are also particularly adapted to be used as a nozzle array for optical spectrometry. Since each microfluidic channel in the nozzle array device terminates with a nozzle opening having an inside diameter of 20 μm or less and the substrate of the nozzle array device is formed of a polymeric material which is generally hydrophobic, liquid inside the microfluidic channel does not drip or be discharged out of the nozzle without external force being applied thereto. When light, either ultraviolet or visible, is incident on the reservoir side of the array, the light will come out of the nozzle opening carrying the optical spectroscopic information of the analytes contained within the liquid in the microfluidic channel. The microfluidic channel and the nozzle opening thus provide an optical detection system without the use of optical windows. This is a significant advantage since the microfluidic nozzle array device does not have to be fabricated to incorporate optical windows made of an optical material in its design. This results in reduced structural complexity for the microfluidic nozzle array device and also a reduction in both cost and complexity relative to the fabrication of the microfluidic nozzle array device.

A 96 microtiter nozzle plate filled with samples can be placed in an ultraviolet reader for a 96 microtiter plate and spectrophotometric information for each sample can be obtained with the reader. A conventional microtiter plate used for UV spectrophotometry must have a sample well bottom made of a special UV transparent material in order to hold the sample inside the well and transmit UV light at the same time or a microtiter plate made of quartz must be used. The use of a microtiter nozzle plate array plate according to one exemplary embodiment thus allows two detection techniques for the samples in the plate without having to transfer the samples to other additional plates.

Figure 16:
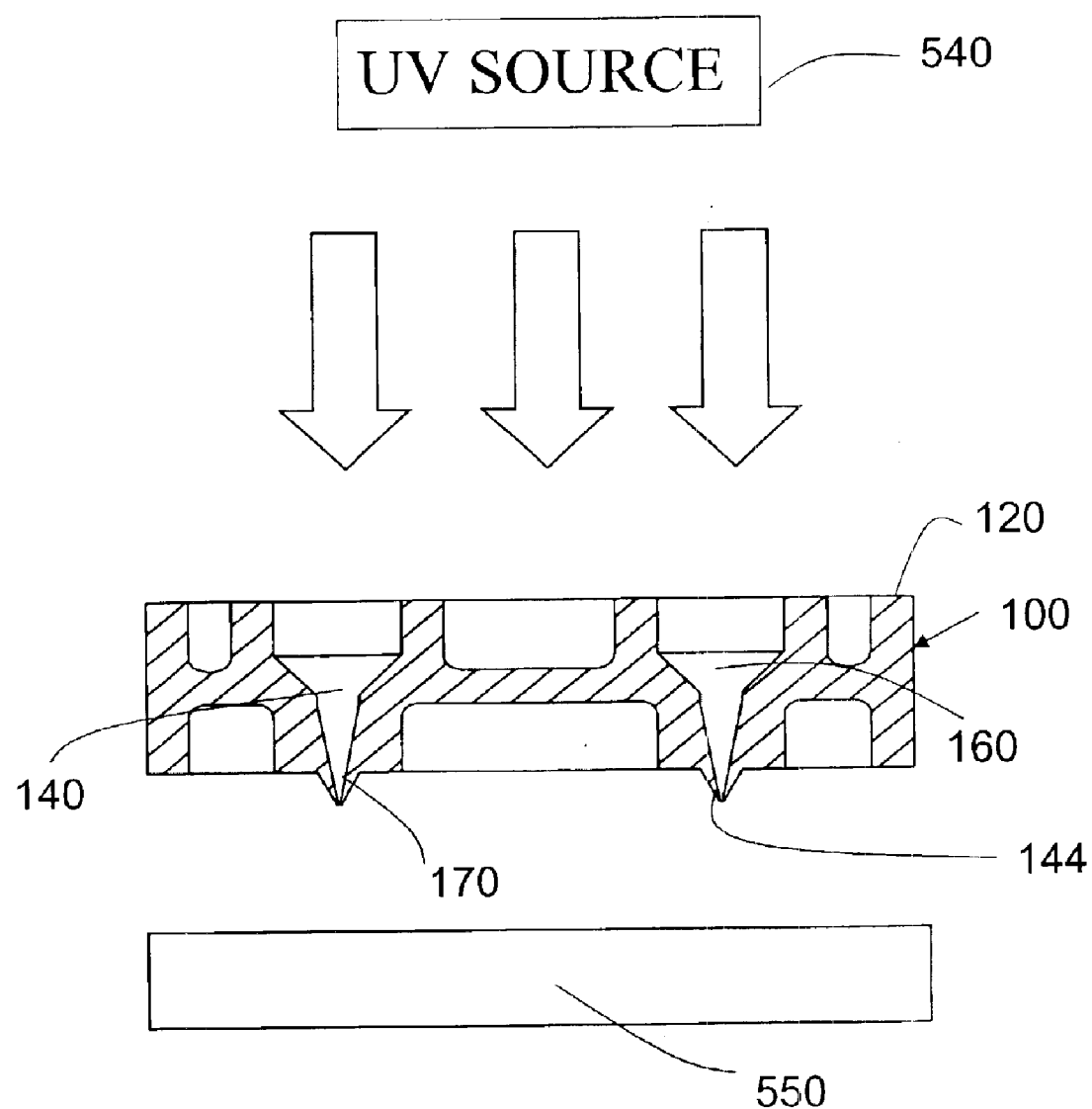
FIG. 16 is a cross-sectional side elevational view illustrating the microfluidic device of FIG. 5 being used in UV spectrophotometry.

FIG. 16 is a cross-sectional view illustrating how the microfluidic nozzle array device 100 can be used for UV spectrophotometry. FIG. 16 illustrates the microfluidic nozzle array device 100 in partial section showing two nozzle structures for purposes of illustrating the use of the microfluidic nozzle array device 100 in UV spectrophotometry. In this exemplary arrangement, UV light is emitted from a source 540 and travels toward the microfluidic nozzle array device 100 and is incident on the reservoir side 120. The UV light travels through the reservoir 160 and continues to travel along the length of the microfluidic channel 140, both of which hold the sample (e.g., liquid and analytes). The UV light travels through the nozzle opening 144 to a detector 550 that is disposed such that it faces the side of the microfluidic nozzle array device that contains the nozzles 170. The UV light carries the spectrophotometric information of the analyte is detected by the detector 550 of the UV reader. In this manner, the formation of perpendicular orientated microfluidic channels provides advantageously permits UV spectrophotometry to be carried out in an easy and convenient manner since the microfluidic nozzle array device 100 can easily be disposed between a UV light source and the detector 550 of the UV reader. Likewise, transmission fluorescence spectroscopy can be carried out using the microfluidic nozzle array device 100.

Unlike conventional microfluidic devices where optical windows formed of an optical material were fabricated in the devices, the substrate body of the present microfluidic nozzle array device does not have to be formed of an optically transparent material. This reduces the complexity of the fabrication process since this requirement is not present in the microfluidic nozzle array device.

The present microfluidic nozzle array devices disclosed herein also can be used in a wide range of other applications in which similar conventional devices have typically been used. For example, the microfluidic nozzle array device can be used for spotting DNA or protein array on a substrate instead of using the conventional capillary wicking methods that are now used with metallic capillaries. Presently, the DNA array spotting is primarily carried out by "wicking" DNA fragments into an open split end of a metallic capillary.

To spot in an array format on a glass slide, the split end of the capillary is pressed slightly onto the glass slide by a robotic arm or the like to facilitate the deposition of the DNA fragments. On being lifted from the glass slide, the metallic capillary has a tendency to "spring" off the glass slide. As a result of this phenomena and other factors, it is common that about 20% of spots in the array are deficient in some way, e.g., either the spot is bare or an inadequate amount of material has been deposited. Spotting is typically carried out with a row of eight to twelve capillaries using an expensive machine and the capillaries are rinsed and reused for different DNA samples.

The present microfluidic nozzle array devices disclosed herein have smaller nozzles openings (e.g., 20 $\mu$m or less) than conventional nozzle constructions and a number of advantages can be realized using the present microfluidic nozzle array devices in comparison to the conventional metal capillaries. First, the injection-molded microfluidic nozzle array devices can be disposed of after each deposition. Thus, the time consuming rinsing process is eliminated and there is no risk of cross-contamination since the devices are not reused. Second, DNA or protein molecules are not adsorbed on the walls of the polymeric nozzle as they are adsorbed on metallic surfaces. The spotting is therefore more complete when the molecules leave the polymeric nozzle to be deposited on the glass slide. Third, a two dimensional nozzle spotter can be manufactured inexpensively thereby greatly increasing the speed of the spotting operation. Fourth, the deposition of the DNA or protein molecules from the polymeric nozzle can be assisted by pumping the molecules out of the nozzle with high pressure air using one of the aforementioned devices and/or with an electric field for electrospray.

The microfluidic nozzle array device can also be used for spotting the plate for matrix-assisted laser desorption ionization (MALDI), replacing the pipette and capillary spotting methods. For matrix-assisted laser desorption and ionization mass spectrometry, a dominant analytical technique for protein molecules and fragments of high molecular weight, the molecules to be analyzed are deposited on a layer of matrix material, usually UV-absorbant molecules that can be vaporized by a UV laser. The molecules of interest are thus carried into the gas phase and are ionized alongside the matrix molecules. Traditionally, the metallic (usually aluminum) MALDI plate is spotted manually with the use of micropipettes and more recently with capillaries. The efficiency of the ionization process will be enhanced if the metallized polymeric nozzles are used for spotting. The matrix material is first electrosprayed onto the aluminum MALDI plate which is held at ground potential, whereas the metal coated nozzle is held at high voltage or vice versa. The molecules of interest are then electrosprayed in a new nozzle onto the matrix material. The spraying allows the matrix molecules and the molecules of interest to be more evenly intermingled with one another, thus enhancing the efficiency of laser assisted desorption and ionization. The spotting of the MALDI plate may also be carried out with a two-dimensional array of nozzles for high throughput. Thus, the density of the nozzle array can be greatly increased and this permits the density of the spotting array to be increased. Accordingly, more testing or experimental sites are provided on the substrate as a result on the increased density in the spotting. It will also be appreciated that an electric field can also be used to assist in the spotting process. The electric field can be generated by using the arrangement illustrated in FIG. 3 or by some other type of suitable arrangement.

One will further appreciate that the manufacturing methods disclosed herein that are based on injection molding techniques can be used to make pipette tips for nano to picoliter dispensing. In other words, a mold can be fabricated and resin can be injected into the mold to form pipette tips that have an elongated body and terminate in a tip section that has a tip opening having an inside diameter of less than about 20 $\mu$m (with the tip section having an outside diameter of less than about 50 $\mu$m.

The following examples serve merely to illustrate several embodiments of the present microfluidic array devices and do not limit the scope of the present invention in any way.

EXAMPLE 1

A polymeric microfluidic nozzle array device is fabricated using the technology disclosed herein is by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tip (i.e., the diameter of the nozzle opening) being less than about 20 microns.

By polishing the conical surface of the mold that defines the nozzle, the outer surface of the nozzle is made much smoother and further the shape of the nozzles is more consistent from nozzle to nozzle and from mold run to mold run. By providing a smooth highly polished surface in the conical portion, the friction of the resin flow is reduced and this results in an increase in the accuracy and efficiency of the injection process. These techniques provide advantages when forming structures having very small dimensions, such as the nozzles of the present microfluidic device which have microscale features.

The microfluidic nozzle array device is then used as an electrospray device for spraying a liquid sample that is disposed within the microfluidic features formed in the microfluidic nozzle array device. As described in detail hereinbefore, the nozzle serves to spray the liquid sample into a fine mist through electric-field induced evaporation. In this example, a voltage of between 5–6 KV is applied to a conductive region formed around the nozzle tip in order to provide the necessary electric-field. The vaporized, ionized sample is then injected into an inlet of a mass spectrometer for analysis.

EXAMPLE 2

A polymeric microfluidic nozzle array device is fabricated using the technology disclosed herein by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tips (i.e., the diameter of the nozzle opening) being less than about 20 microns. The mold is constructed so that a microfluidic nozzle array strip is formed having two rows of twelve nozzles each.

Upon removing the molded microfluidic nozzle array strip, the above process is repeated to form one or more other microfluidic nozzle array strips. The microfluidic nozzle array strips are then placed side by side and adjacent strips are detachably secured to one another by applying an adhesive (e.g., glue) to an edge of the each of the strips. More specifically, the edges are heated so that the polymeric material softens and then the adjacent strips are joined together along these edges so that a fused bond results between the two edges that are brought into contact. Preferably, the fused bond between adjacent strips includes a weakened section (e.g., a score line or the like can be formed along the bond or the thickness of the bonded interface section between the two strips can be of reduced thickness) so that one strip can easily be detached from the other strip. Any remaining microfluidic strips are attached in the same manner to form a single, tiled microfluidic nozzle array device that contains a weakened section between the adjacent bonded microfluidic devices. The number of bonded microfluidic nozzle array strips will vary depending upon the desired overall size of the microfluidic nozzle array device and more particularly, the desired overall number of reservoirs and nozzles per each microfluidic device. In use, the single, tiled microfluidic nozzle array device is broken apart into two or more sections which can be used or can further be broken apart into additional smaller microfluidic devices.

EXAMPLE 3

A polymeric microfluidic nozzle array device is fabricated using the technology disclosed herein by first providing a mold designed for an injection mold process. The mold is formed of a metal and a conical surface of the mold that defines the nozzle portion of the microfluidic device is polished with a diamond paste to form a highly polished surface. More specifically, the conical surface is polished with 1 micron diamond particles to provide a close to mirror finish for the nozzle that is formed as part of the microfluidic device. The microfluidic device is fabricated by injecting polybutyl terephthalate (PBT) into the closed mold and then curing the formed structure and then ultimately removing the molded microfluidic nozzle array device from the mold. The microfluidic nozzle array device is formed to have nozzles that have an average outside diameter of about 60 microns and an average inside diameter of the tips (i.e., the diameter of the nozzle opening) being less than about 20 microns. The mold is constructed so that a microfluidic nozzle array strip is formed having two rows of twelve nozzles each.

Upon removing the molded microfluidic nozzle array strip, the above process is repeated to form one or more other microfluidic nozzle array strips. FIG. 17 generally illustrates the concept of tiling or otherwise combining a number of nozzle subunit structures into a microfluidic nozzle array device of greater dimension. A base plate 600 is provided and serves as the means for receiving a number of nozzle subunits structures, generally indicated at 610, in a manner in which the nozzle subunit structures 610 are releasably interlocked with the base plate 600. More specifically, the base plate 600 is a frame-like member having a predetermined number of retaining rails 620 that are affixed at their ends to a pair of end walls 630. The rails 620 are spaced apart from one another so that open slots 640 are formed between adjacent rails 620.

Figure 18:
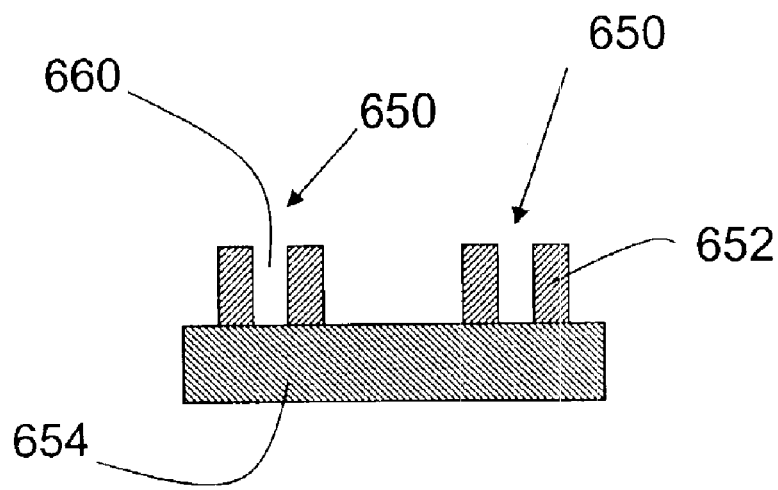
FIG. 18 is a cross-sectional view taken along the line 18—18 of FIG. 17.

As illustrated in FIGS. 17 and 18, each rail 620 has a number of clamping features 650 formed as a part thereof and spaced along the length of the rail 620. The clamping feature 650 includes side walls 652 that are spaced apart from one another to define a retaining slot 660 therebetween. The side walls 652 are disposed parallel to one another and extend upwardly from a floor 654 of the clamping feature 650. The distance between inner surfaces of the side walls 652 is selected so as to provide a frictional fit between a side wall of the nozzle subunit structure 610 so as to secure the structure 610 to the base 600 while at the same time permitting the structure 610 to be disengaged and easily removed from the base 600. Accordingly, the distance between the inner surfaces of the side walls 652 is equal to or slightly greater than a width of the side wall of the structure 610 that is received within the retaining slot 660 between the side walls 652.

Alternatively, the entire length of the rail 620 can have a "U-shaped" cross-section with a retaining slot 660 being formed between two side walls 652 that are spaced apart from one another. In this embodiment, the entire rail 620 serves as locking member instead of discrete clamping features 650 that are spaced along its length.

In the illustrated embodiment, each nozzle subunit structure 610 includes four nozzles 612 and four reservoirs (not shown) on the opposite side of the structure 610. For purpose of illustration only, the nozzles 612 are illustrated as facing away from the clamping features 650 (such that the nozzles 612 are in a plane above the clamping features 650); however, the structure 610 can be releasably interlocked with the base 600 such that the nozzles 612 face in the opposite direction. In other words, the reservoirs at the opposite end of the microfluidic channel face away from the clamping features 650 and are located in a plane above the clamping features 650.

The nozzle subunit structures 610 are releasably interlocked with the base 600 by inserting the two opposing side walls 611 of one nozzle subunit structure 610 into retaining slots 660 of two adjacent rails 620 that face another with an open slot 640 therebetween. One side wall 611 can be inserted first and then the other side wall 611 can be inserted into the other retaining slot 660 or both side walls 611 can be aligned with the slots 660 and then the nozzle subunit structure can be pressed downward to effectively dispose the side walls 611 within the retaining slots 660. Because both the nozzle subunit structure 610 and the base 600 are preferably formed of plastic materials and the dimensions of the structures are carefully selected, a frictional fit results when the side walls 611 are received within the retaining slots 660. When the side walls 611 are received within the retaining slots 660, the nozzles 612 and the reservoirs are received within the open slot 640 such that these elements are not obstructed by the base 600. In other words, the reservoir openings are clear so that samples can be injected or otherwise disposed within the reservoirs and also the nozzle openings are clear so that the sample can be discharged.

In one embodiment, the base 600 is formed of a polymeric material and is manufactured using an injection molding process such that the base 600 is formed as a unitary structure. While a frictional fit is one manner of releasably interlocking the nozzle subunit structures 610 to the base 600, a small amount of adhesive may be used at the interface between the side walls 611 and the clamping features 650 to ensure that the nozzle subunit structures 610 remain in place during various applications (when the base 600 may need to be turned upside down, etc.). Further, some applications require that a force be applied to the backside of the nozzle subunit structure 610 (e.g., due to actuation of a plunger in the reservoir, etc.) and therefore it is desirable for the nozzle subunit structures 610 to remain in place and not become dislodged from the base 600 when this force is applied. Any number of suitable adhesives can be used and it will be appreciated that one type of adhesive is a releasable adhesive that permits the nozzle subunit structure 610 to be removed from the base 600.

Figure 19:
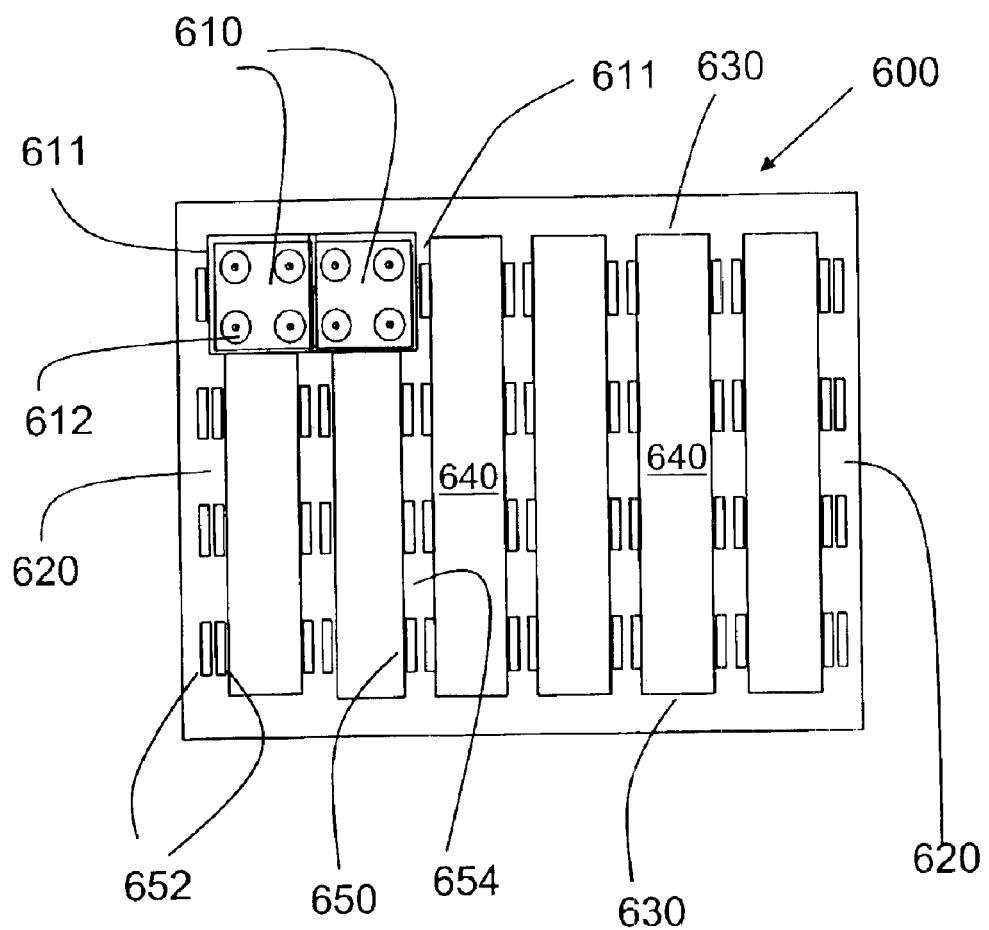
FIG. 19 is a top plan view of a retaining base according to another embodiment for releasably holding a number of microfluidic nozzle subunit structures.

FIG. 19 illustrates another embodiment of base 600 that is very similar to the configuration illustrates in FIGS. 17–18. In this embodiment, the clamping features 650 are configured to receive two side walls 611 of adjacent nozzle subunit structures 610. Thus, the distance between the inner surfaces of the side walls 652 is selected so that the width of two side walls 611 placed in intimate adjacent contact with one another is about equal to or slightly less than the distance between the inner surfaces of the side walls 652. In other words, the slot 660 is configured to receive and retain two side walls 611 of adjacent nozzle subunit structures 610. To removeably couple the nozzle subunit structures 610 to the base 600 according to this embodiment, one side wall 611 is disposed within the slot 660 and then another side wall 611 of an adjacent nozzle subunit structure 610 is disposed in the slot 660 next to the other side wall 611, thereby providing a frictional fit that results in both adjacent nozzle subunit structures 610 being held securely in place. Unlike the embodiment of FIGS. 17–18, this embodiment requires that the two side walls 611 be disposed within one slot 660 to effectively couple each nozzle subunit structure to the base 600.

It will be appreciated that other clamping members can be used besides the above described ones. For example, each clamping member can consist of a spring biased clip that receives side wall 611 in a frictional manner so as to retain and hold the side wall 611 in a releasable manner. The clip can consist of two opposing plates that are hingedly connected at one end so as to bias the plates toward one another. The side wall 611 is received at the opposite ends of the plates inserting the side wall 611 between the plates and then directing the side wall 611 between the plates toward the hinged end. The biasing action between the plates ensures that the side wall 611 is securely gripped between the plates, while at the same time can be removed by simply overcoming the biasing force and lifting the side wall 611 upward until it is free of the plates.

Figure 20:
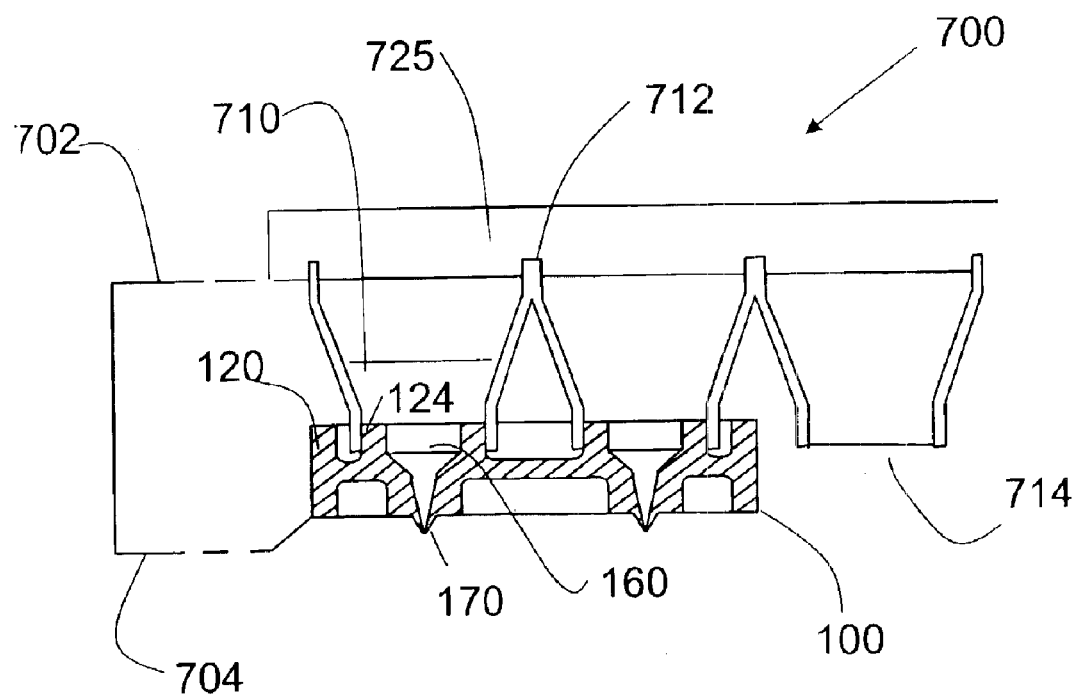
FIG. 20 is a cross-sectional view of an interface plate that can be used to assemble at least one microfluidic device having an array of nozzles.

FIG. 20 illustrates yet another base 700 for tiling or otherwise combining a number of nozzle subunit structures into a microfluidic nozzle array device of greater dimension as well as providing a means for increasing the volume of the reservoir that forms a part of the microfluidic nozzle array device. The base plate 700 is formed of a plastic material and preferably is formed of a plastic material that can be injection molded. As previously mentioned, injection molding provides a low cost method of forming the base plate 700 without jeopardizing either the integrity of the base plate 700 or the micro-scale features that are formed as part of the base plate 700.

In this particular embodiment, the base plate 700 resembles a conventional microtiter plate of a specific format, e.g., a 96-well, on a surface that receives the robotic dispensing pipettes. The base plate 700 can be formed to have a number of different shapes; however, the base plate 700 generally includes an upper face 702 and an opposing lower face 704. The base plate 700 has a number of open-ended wells 710 formed therein and arranged according to a predetermined pattern. An upper end 712 of the well 710 defines, in part, the upper face 702 of the base plate 700, while a lower end 714 of the well 710 is spaced from the lower face 704. The well 710 has a tapered construction in that the upper end 712 has a width that is greater than the lower end 714 of the well 710. It will be appreciated that the well 710 can be formed to have any number of different cross-sectional shapes and in one exemplary embodiment, the well 710 has a generally annular shape (i.e., circular cross-section).

The base plate 700 is configured to hold at least one microfluidic nozzle array device, such as the device 100 illustrated in FIG. 5. For purpose of illustration, the base plate 700 will be discussed as being used for holding device 100; however, it will be appreciated that devices having different features and/or configurations can be used so long as the device has retaining features that permit the device to be coupled to and retained by the base plate 700. More specifically, the device 100 has a number of features formed therein for coupling with the lower ends 714 of the wells 710. For example, the first face 120 of the device 100 includes reservoir walls 124 that partially define the reservoir 160. In the exemplary embodiment, the reservoir wall 124 has an annular shape since the reservoir 160 itself has such a shape. The first face 120 is configured so that the reservoir wall 124 is raised relative to the surrounding sections of the first face 120 and therefore, a member can be fitted around the outer surface of the reservoir wall 124.

The base plate 700 is constructed so that one or more devices 100 can easily be coupled thereto, resulting in a number of smaller devices 100 being assembled as a larger grid of devices 100. Such coupling between the devices 100 and the base plate 700 is releasable in nature in that any one of the devices 100 can easily be removed and/or replaced. To couple one or more devices 100 to the base plate 700, each device 100 is positioned so that the reservoirs 160 are aligned with the wells 710 formed in the base plate 700. The inner diameter of the lower end 714 of the well 710 is slightly greater than or about equal to the outer diameter of the reservoir wall 124 to permit the lower end 714 of the well 710 to fit snugly over the reservoir wall 124, thereby coupling the device 100 to the base plate 700.

The wells 710 are arranged across the base plate 700 so that for each reservoir 160 there is corresponding well 710 and further there is at least one well 710 that is aligned with each reservoir 160 of the device 100 when the device 100 is securely coupled to the base plate 700. Because there is a corresponding well 710 for each reservoir 160 of the device 100, the base plate 700 serves to actually increase the volume of the reservoir 160 due to the well 710 acting as an extension of the reservoir 160. In other words, the reservoir 160 can be filled through the well 710 and any amount of sample that overflows the reservoir 160 is merely stored in the well 710. As the sample is discharged through the nozzle 170 in the manner described hereinbefore, sample from the well 710 is fed into the reservoir 160 to replace the amount that has been discharged. There is another advantage to the base plate 700 and its ability to increase the effective size of the reservoir in that the increased volume of the reservoir behind each nozzle 170 permits the device 100 to be compatible with and conform with robotic dispensing equipment. This is illustrated in FIG. 20 which shows that the sample (e.g., liquid) in each well 710 is held in much higher volume than when only the reservoir 160 of the nozzle array is used for holding the sample.

Alternatively, the lower end 714 can interface with the reservoir wall 124 in a different manner in that the lower end 714 can be received within (between) the reservoir wall 124. In other words, the outer diameter of the lower end 714 is selected to be slightly less than or about equal to an inner diameter of the reservoir wall 124. In this embodiment, the lower end 714 is snugly received within the reservoir wall 124 in such a manner that the device 100 is securely coupled to the base plate 700.

In both instances whether the lower end 714 is received within the reservoir wall 124 or the lower end 714 is disposed around the reservoir wall 124, the joint at the junction between the lower end 714 and the reservoir wall 124 forms a liquid-tight and air-tight junction for gas over pressure up to a few pounds per square inch (psi).

As illustrated in FIG. 20, when the device 100 is coupled to the base plate 700, the lower face 704 protrudes beyond (e.g., extends below) the nozzles 170 and has chamfered edges 705 so as to protect the tips of the nozzles 170 without obstructing the function of the nozzles 170. The lower face 704 should extend below the nozzle tips to prevent damage to the nozzle tips and to permit the base plate 700 to seat against a planar surface as might be the case when the base plate 700 is attached to equipment, such as an electrospray device or a spectrophotometer. The protruding corners of the base plate 700 also protect the tips of the nozzles 170 during handling, etc.

In the embodiment where the base plate 700 is to function as an interface plate for robotic dispensing equipment, the base plate 700 has a height that is complementary to the conventional robotic dispensing equipment. According to one exemplary embodiment, the base plate 700 includes 96 open-ended wells 710 arranged in the standard 8×12 grid format. The height of the entire base plate 700 and the nozzle array device 100 can be made to conform to that of the standard microtiter plate. In this manner, the reservoir volume can be varied and selected in view of the given application of the device 100. For example, the base plate 700 and more particularly, the well 710 thereof, can be made so that the combined volume of the well 710 and the reservoir 160 is about 370 μl as in one of the standard volumes for a 96 well plate or any other desired volume without the need to change the mode design of the nozzle array device 100. In other words, the effective volume of the reservoir 160 can be varied by varying the dimensions of the well 710 as opposed to having to provide different devices 100 having reservoirs 160 of varying volumes.

Furthermore, a device 100 having a nozzle array with a 384 well spacing can be attached to a 96 well plate attachment if only one our of every four nozzles 170 is used to attach to each lower end 714 of the well 710. Thus, not all of the wells 710 and/or reservoirs 170 need to be used in any given application. The additional advantage of the tiling base plate 700 is that existing commercially available sealing mats and its robotic sealing mechanism can be directly applied to the base plate 700 without major modifications.

The upper end 712 of the well 710 is constructed to fit a puncturable sealing mat 725. The puncturable sealing mat 725 is disposed across the upper face of the base plate 700 so that at least the upper ends 712 of the wells 710 are covered by the puncturable sealing mat 725. Puncturable sealing mats 725 are known in the art and can be obtained from a number of commercial sources. The puncturable sealing mat 725 is used to prevent evaporation of sample liquid from the well 710 while the base plate 700 is being docked in preparation for transfer to a piece of equipment, such as a mass spectrometer, etc.

The base plate 700 thus incorporates open-ended wells 710 that resemble open-ended tubes and have a first diameter at one end (e.g., lower end 714) for interfacing with the reservoir wall 124 of the device 100 and a second diameter at the other end be selected so that this end has the same opening as a conventional well in a microtiter plate 700. The advantages provided by the base plate 700 include increased sample storage volume, improved sealing of the reservoir 160 with commercially available sealing mats, and improved handling of the nozzle array devices 100. In addition, the cost of the base plate 700 is also relatively inexpensive since the base plate 700 is preferably manufactured by an injection molding process.

Figure 21:
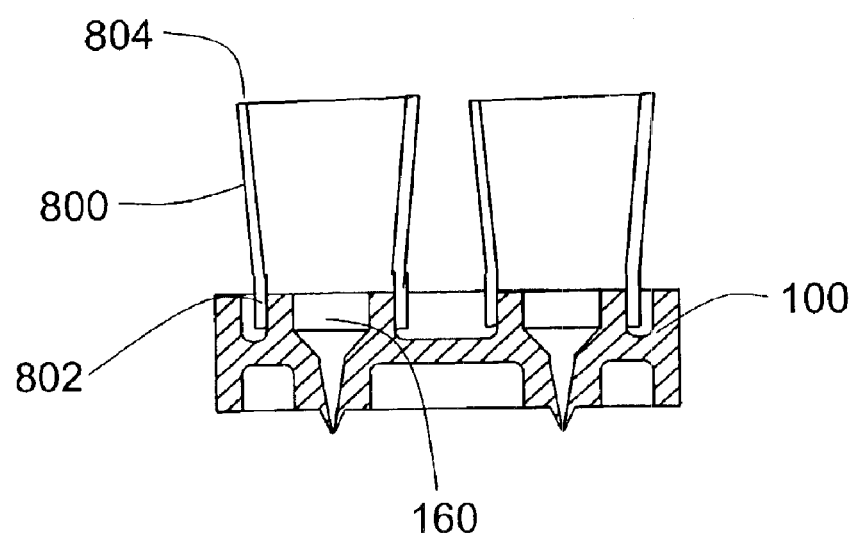
FIG. 21 is a cross-sectional view of a microfluidic device having an array of nozzles with open ended tubings attached to the reservoirs thereof.

FIG. 21 illustrates another embodiment for effectively increasing the volume of the reservoir 160 of the device 100. More specifically, an open-ended conduit member 800 is mated with the reservoir wall 124 so as to effectively increase the volume of the reservoir 160. The conduit member 800 in one exemplary embodiment is a piece of tubing that has an open first end 802 and an open second end 804. The tubing 800 can be constructed so that it has the same dimensions along its length or the tubing 800 can be constructed so that one end thereof has greater dimensions than the other end. In the latter embodiment, the tubing 800 has a tapered construction. FIG. 21 shows the tubing 800 with slightly tapered construction with the first end 802 that attaches to the reservoir wall 124 having smaller dimensions than the second end 804 that is spaced above the first face 120 of the device 100.

In one embodiment, the first end 802 has an inner diameter that is slightly greater than or about equal to an outer diameter of the reservoir wall 124 so that the first end 802 can be disposed around the reservoir wall 124 in a snug-fit manner (e.g., to provide a liquid-tight and air-tight junction between the device 100 and the tubing 800). Alternatively, the first end 802 has an outer diameter that it slightly less than or about equal to an inner diameter of the reservoir wall 124 to permit the first end 802 to be received within the reservoir 160, thereby securely coupling the device 100 and the tubing 800.

The tubing 800 can be formed of any number of materials that are typically used for forming tubing, e.g., plastic materials and rubber materials. As with the embodiment illustrated in FIG. 20, the tubing 800 effectively increases the volume of the reservoir 160 since the tubing 800 acts as an extension of the reservoir 160. This provides the advantages that are discussed above in reference to the base plate 700.

Figure 22:
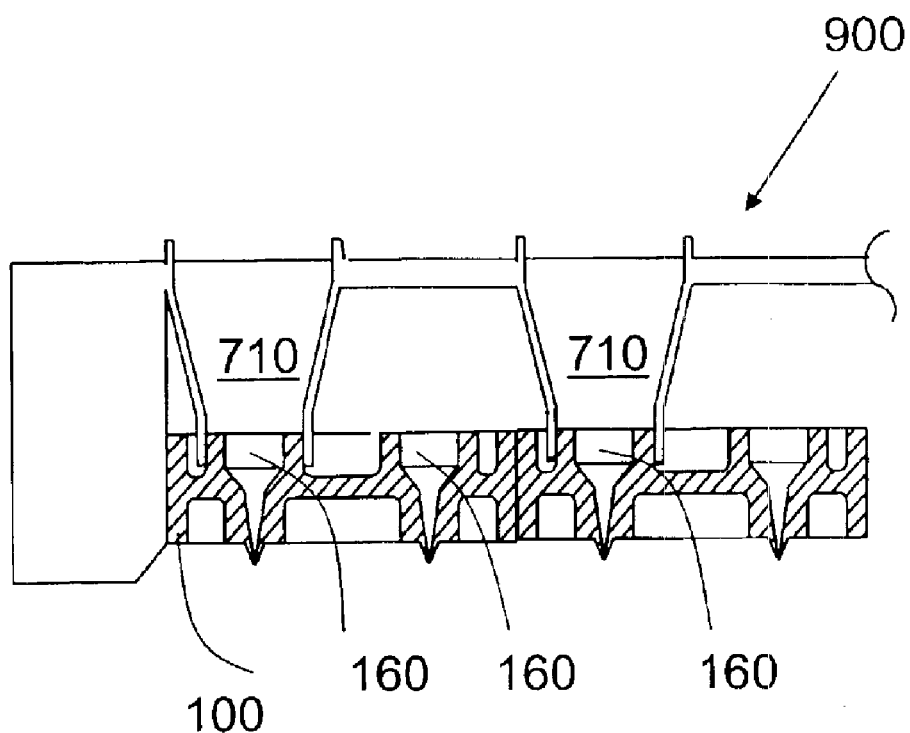
FIG. 22 is a cross-sectional view of an interface plate according to another embodiment that can be used to assemble at least one microfluidic device having an array of nozzles.

FIG. 22 illustrates yet another embodiment of a base plate 900 that is similar to or identical to the base plate 700 in terms of its construction. The difference between the arrangement illustrated in FIG. 22 and the arrangement illustrated in FIG. 20 is that the base plate 900 configuration is different from the nozzle array configuration of the device 100 as opposed to the base plate 700 and the device 100 configuration which were intended to match one another. For example, the base plate 900 can be of the 8×12 96 well grid format, while the nozzle array devices can have a spacing associated with a 384 well plate spacing. In other words, there are more reservoirs 160 than there are wells 710 and therefore, each reservoir 160 does not align and match up with a corresponding well 710; however, each well 710 preferably is aligned with one reservoir 160. Such a base plate construction is thus configured to utilize only selected reservoirs 160 as opposed to utilizing all of the reservoirs 160 without requiring either the base plate and/or the nozzle array device to be custom constructed for a specific application.

The above-described embodiments of FIGS. 20–22 provide a nozzle array that is compatible with microtiter plate formats but has smaller nozzle array components and can be used to assemble a number of nozzle array devices in a tiled manner. Advantageously, each embodiment provides a means for increasing the effective volume of the reservoir of the nozzle array device since the well formed in the plate is effectively and securely coupled to one end of the reservoir, thereby permitting a sample to be injected into the well resulting in sample being directed into the reservoir and ultimately into the nozzle tip. By increasing the effective volume of the reservoir, the nozzle array device is made more conformant with robotic dispensing equipment.

Figure 23:
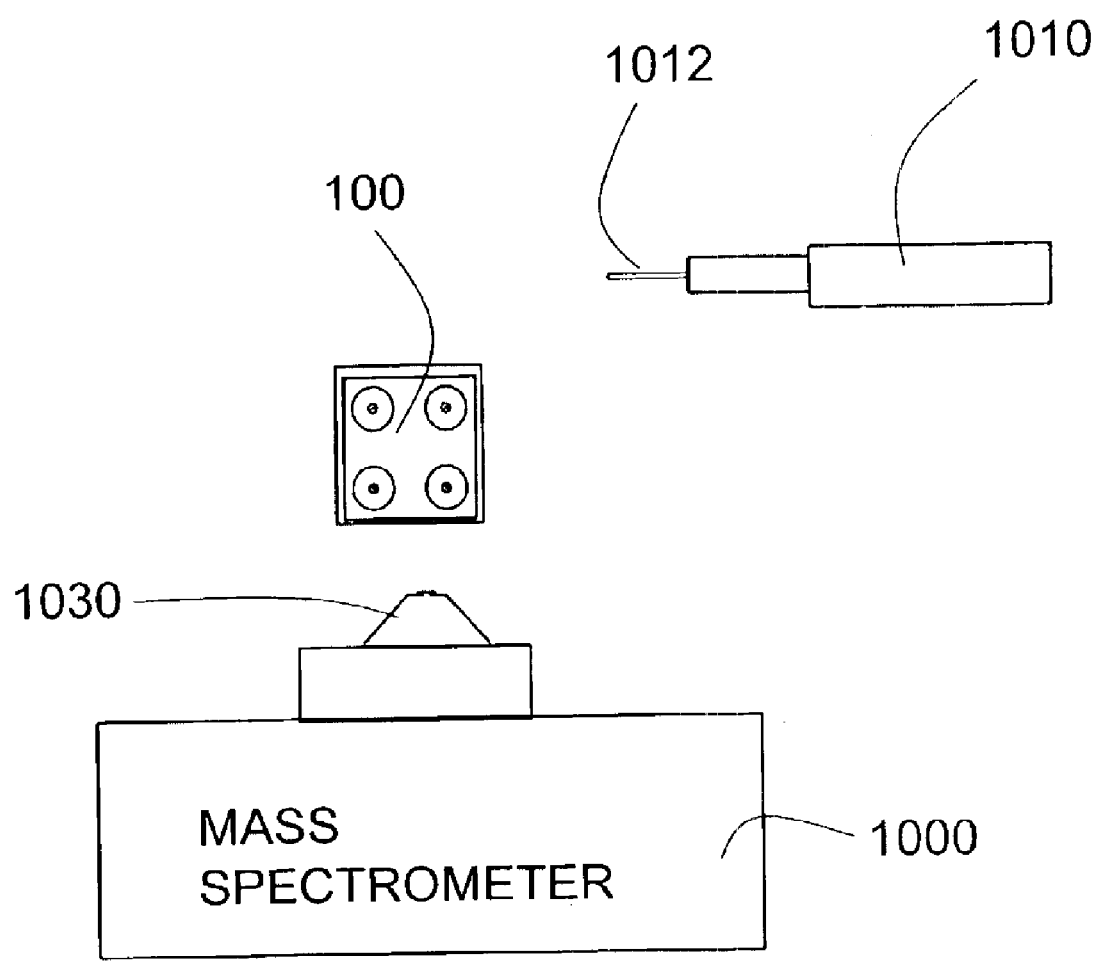
FIG. 23 is a top plan view of a mass spectrometer unit and an apparatus for deploying a microfluidic device having an array of nozzles in the mass spectrometer unit independent of its make.

Now referring to FIGS. 23–30 in which yet another aspect of the present invention is illustrated. In FIG. 23, a general mass spectrometer set up is generally illustrated and includes a mass spectrometer unit 1000 and a conventional electrospray needle assembly 1010 that is used to convert a liquid sample into a vapor plume by a technique that is typically referred to as electrospray ionization (ESI). The electrospray needle assembly 1010 sprays samples at flow rates that are about 5 microliters/minute and higher depending upon the precise application and the operating parameters. The electrospray needle assembly 1010 is fixedly attached to the mass spectrometer unit 1000 to permit the liquid sample to be ionized to form the vapor plume which is received in part into an inlet port of the mass spectrometer 1000. For example, the mass spectrometer 1000 has an inlet cone 1030 that is configured to receive a portion of the vapor plume that is formed by the electrospray needle assembly 1010. The inlet cone 1030 has an inlet opening extending therethrough which receives the vapor plume.

In electrospray ionization, an analyte solution, is passed, at atmospheric pressure, through a capillary into a smaller diameter tip 1012 held at a high potential (e.g., a few KV). The effect of the electric field as the solution emerges from the tip 1012 is to generate a spray of highly charged droplets that pass down a potential (and pressure) gradient towards an analyzer, which in this case is the mass spectrometer unit 1000. The tip 1012 is typically spaced from the inlet cone 1030 and is arranged so that the opening formed through the tip 1012 is not axially aligned with the opening formed through the inlet cone 1030. Instead, the tip 1012 is arranged that its longitudinal axis is normal to an axis through the opening of the inlet cone 1030. Further, the opening formed through the tip 1012 and the inlet opening formed through the inlet cone 1030 typically lie in the same plane when the electrospray needle assembly 1010 is fixed in place relative to the mass spectrometer unit 1000.

Electrospray ionization is highly inefficient since it is characterized by relatively high flow rates of the analyte solution in order to provide enough sample to be received within the inlet cone 1030 to permit the mass spectrometer unit 1000 to function properly. For example, it is commonplace for only about 4% of the sprayed analyte solution to be captured within the inlet cone 1030 and because of the high sample flow rates of the analyte solution in electrospray ionization applications, this results in a significant quantity of sample being wasted.

Because of the aforementioned and other deficiencies, nanospray has and is increasingly becoming an attractive alternative to electrospray ionization. Nanospray is the technique used in mass spectrometry to convert a liquid sample into a vapor plume using substantially less sample as compared to conventional electrospray ionization. As previously-mentioned, flow rates of the sample through the nanospray nozzle is typically well under 1 microliter/minute. However, there are a number of disadvantages that must be overcome in order to realize the benefits of nanospray. For example, one of the difficulties that is encountered when a user wishes to use the mass spectrometer unit 1000 for both nanospray and electrospray applications is that existing apparatuses for use with nanospray devices require the user to remove the conventional ESI fixture and insert the selected nanospray apparatus in its place. In other words, the conventional electrospray needle assembly 1010 must be detached from the mass spectrometer unit 1000 to permit the nanospray apparatus to be fixed to the same framework that supports the electrospray needle assembly 1010. This is a very time consuming task since each assembly is typically bolted to a frame that supports the mass spectrometer unit 1000 and therefore, the removal of one assembly requires the user to unbolt the assembly and bolt the other in place. The amount of time required for set-up and performing the analysis must factor in the time required to make sure that the correct equipment is in place and this can require the above unbolting/rebolting steps. Moreover, such an arrangement precludes the use of a "universal" nanospray apparatus that can be used in a mass spectrometer unit of different makes since the nanospray apparatus has to be bolted onto the frame work of the mass spectrometer unit.

As best shown in FIGS. 24, 25, 29 and 30, in order to overcome the above disadvantages and permit the changing from ESI to a nanospray application to be a much easier task and far less time consuming, a universal holder device 1100 is provided. The holder device 1100 is intended to be used with a nozzle array device of a given size, such as the nozzle array device 100 and includes a frame 1110 that receives the device 100. As described in great detail hereinbefore, the device 100 is in the form of a small plastic chip that includes an array of nozzles formed therein. The frame 1110 is preferably formed of a plastic material and has an opening 1112 formed therein that is complementary in shape and size to the outer periphery of the device 100 so that the device 100 is disposed within opening 1112 in such a manner that there are no spaces or very little space formed between the device 100 and the frame 1110. Preferably, the dimensions of the device 100 and the opening 1112 are such that a close frictional fit results between the device 100 and the frame 1110. In addition, a coupling assisting agent, such as an adhesive (glue), etc., can be used to ensure that the device 100 remains securely held in place within the opening 1112 of the frame 1110. In one exemplary embodiment, each of the device 100 and the frame 1110 is either square shaped or rectangular shape.

It will also be appreciated that the device 100 and the frame 1110 can be made as a single integral part as by a common injection molding process. This would eliminate the steps of disposing the device 100 within the frame 1110 and making sure that the two are securely coupled to one another.

Figure 24:
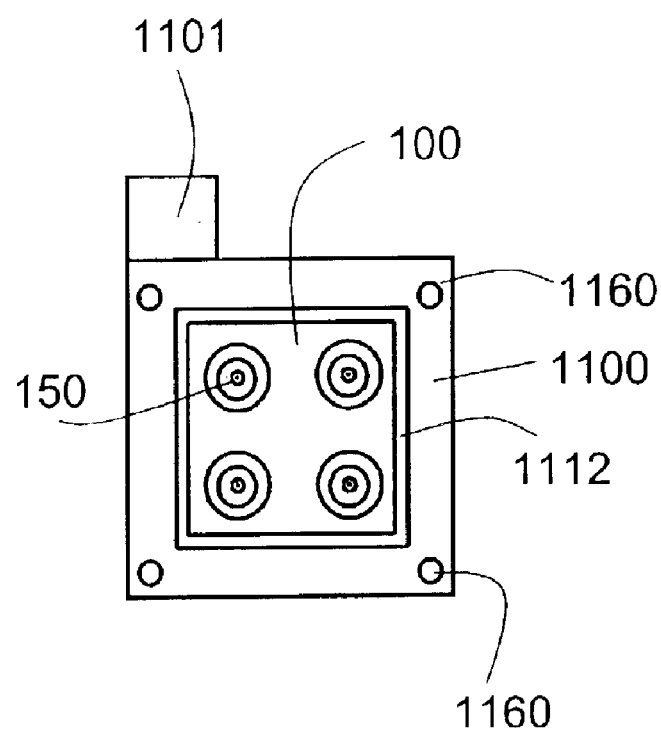
FIG. 24 is a front elevational view of the microfluidic device of FIG. 23.
Figure 30:
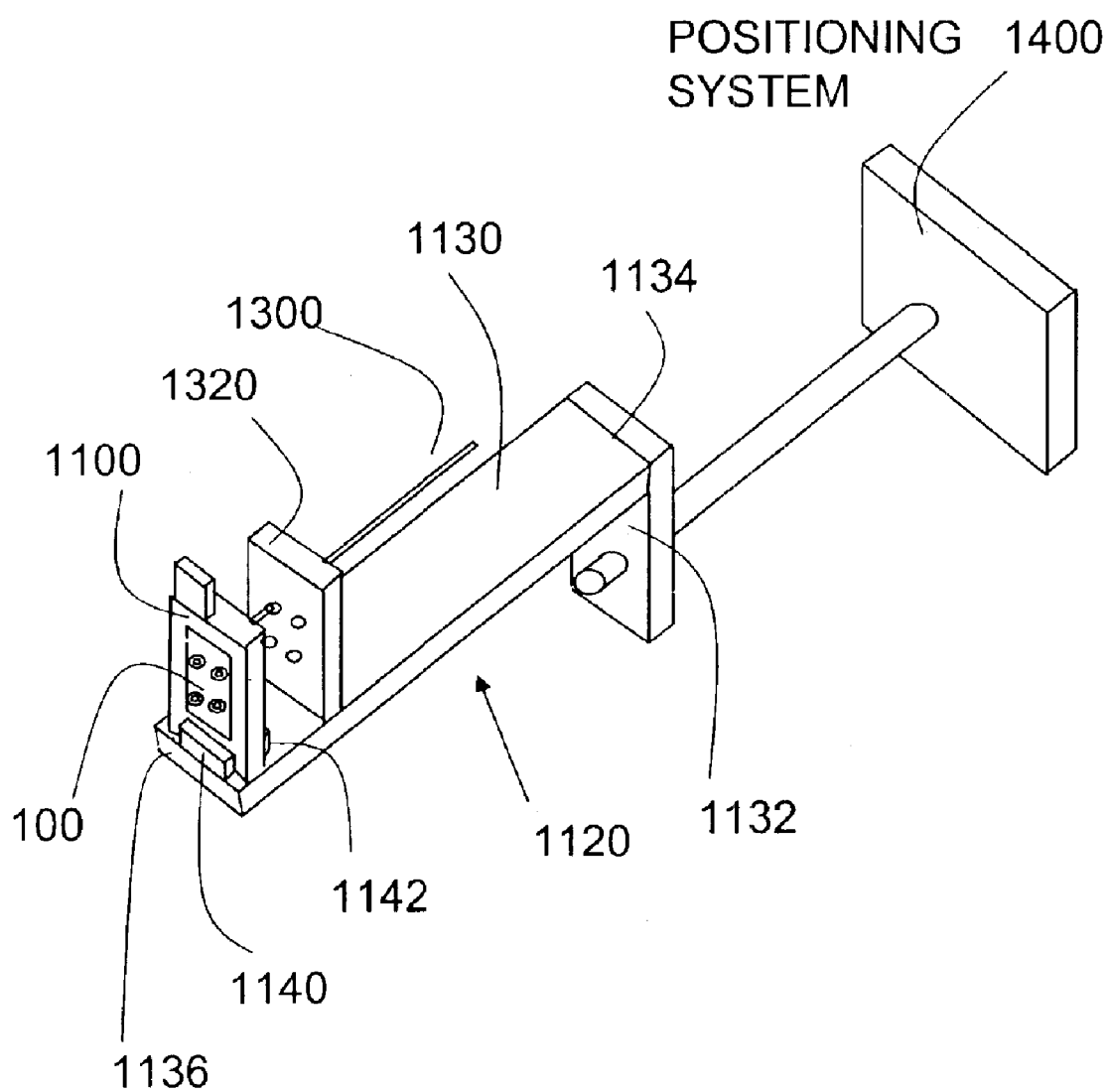
FIG. 30 is a perspective view of a holder for securely holding a microfluidic device and being coupled to an apparatus that has a degree of movement to permit positioning of the microfluidic device with respect to a mass spectrometer unit.

As illustrated in FIGS. 23, 24, and 30, the holder device 1100 also has a holder 1120 for holding the frame 1110 securely in place so that the device 100 can be properly aligned with the mass spectrometer unit 1000 and more specifically, the inlet cone 1030. The holder 1120 can have any number of different shapes so long as the holder 1120 includes a planar platform 1130. According to one exemplary embodiment, the holder 1120 is generally L-shaped in that it includes a support section 1132 that intersects and is integral to one end of the planar platform 1130. The support section 1132 and the planar platform 1130 are thus arranged at a right angle with respect to one another to give the holder 1120 a generally L-shaped construction. In one exemplary embodiment, the holder 1120 is formed of a single piece of plastic, such as a plexiglass material or the like.

The planar platform 1130 is connected to the support section 1132 at a first end 1134 thereof, with a second end 1136 being where the device/frame combination is secured and held in place. More specifically, at or near the second end 1136, first and second retaining members 1140, 1142 are spaced apart from one another to form a space 1144 therebetween for receiving the frame 1100. The first and second retaining members 1140, 1142 can comprise any number of different types of members that are constructed for engaging and holding a member therebetween. For example and according to one exemplary embodiment, the first and second retaining members 1140, 1142 are merely elongated rails that are formed as part of or secured to an upper surface of the planar platform 1130. The rails 1140, 1142 are disposed parallel to one another so that a parallel slot or space 1144 is formed therebetween. The dimensions of the space 1144 are complementary to the dimensions of the frame 1100 so that the frame 1100 can be received and held within the space 1144. For example, the width of the space 1144 can be about equal to or even very slightly less than the width of the frame 1100 so that a secure frictional fit is formed between these components when the frame 1100 is disposed in the space 1144. It is intended for the holder 1120 to be reused with other frames 1100 and therefore, the frame 1100 should be able to be removed from the holder 1120 to permit the user to insert and secure another frame 1100 between the rails 1140, 1142.

When the device 100 is securely held in place between the rails 1140, 1142, the device 100 is in a vertical orientation relative to the planar platform 1130. In other words, the device 100 is upwardly standing between the rails 1140, 1142. The rails 1140, 1142 have a height that does not interfere with spraying of sample through the nozzles that are formed as part of the device 100. Thus, the rails 1140, 1142 typically do not extend beyond a lowermost edge of the frame 1100 and therefore they do not obscure the lowermost nozzles. The length of the illustrated rails 1140, 1142 is such that they do not extend beyond the ends of the frame; however, this is not critical and the opposite configuration is equally applicable.

Figure 25:
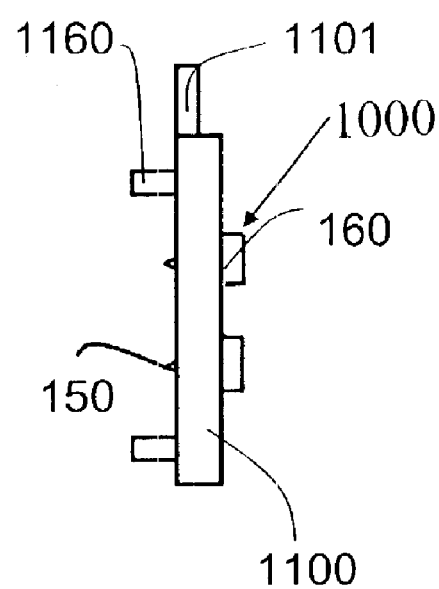
FIG. 25 is a side elevational view of the microfluidic device of FIG. 23.

As best shown in FIGS. 24, 25 and 30, the frame 1100 also preferably has a locating and retaining feature that is formed as part of one or more faces of the frame 1100. In one exemplary embodiment, one face of the frame 1100 includes four posts 1160 that are spaced in each of the corners of the frame 1100. The illustrated frame 1100 is generally square shaped and therefore the distance between any two posts 1160 is approximately the same. Two of the posts 1160 act as locating and retaining features by engaging one of the rails 1140, 1142. More specifically, the two bottommost posts 1160 are formed on the frame 1100 and spaced apart from one another such that one of the rails 1140, 1142 is received between the bottommost posts 1160 in a frictional manner so as to locate and further secure the frame 1100 to the holder 1120 by locking the frame 1100 in place. Each of the posts 1160 has a sufficient height so that the post 1160 can engage one of the rails 1140, 1142 in a manner that limits the lateral movement of the frame 1100. In other words, if the user tries or accidentally applies a lateral force to the frame 1100, the posts 1160 prevent the frame 1100 from moving in the lateral direction. Thus, in order to place the frame 1100 within the holder 1120 or remove it therefrom, the user must press the frame 1100 downward or lift it while the respective rail 1140, 1142 is positioned between the posts 1160. The posts 1160 also serve to protect the nozzles 150 in case the device 100 falls upside down such that the face having the nozzles 150 extending outwardly therefrom is the ground contacting surface. Without the posts 1160, the tips of the nozzles 150 represent the bottommost points of the device 100 and therefore, these tips will strike the surface and likely become damaged and/or destroyed. With the posts 1160, the posts 1160 represent the bottommost points of the device 100 and will therefore strike the ground first instead of the nozzle tips striking the ground. In this manner, the posts 1160 serve to protect the nozzles 150. Thus, the lengths of the posts 1160 must be greater than the height of the nozzles 150.

The frame 1100 also includes a tab 1101 for handling thereof as shown in FIGS. 24 and 25. For example, the tab 1101 extends outwardly from one edge of the frame 1100 and permits a member for the user to easily grasp when the user is either inserting or removing the frame 1100 into or out of the holder 1120. The tab 1101 is thus positioned on the top edge of the frame 1100 when the frame 1100 is inserted into the holder 1120 to permit the tab 1101 to be easily accessible to the user. Thus, the user will grip the frame 1100 by the tab 1101 when the user lowers the frame 1100 into the holder 1120 and conversely, the user grips the tab 1101 to remove the frame 1100 from the holder 1120. While the illustrated tab 1101 has a square shape, the tab 1101 can have any other number of shapes, such as oval, triangular, irregular shape, etc.

The remaining part of the planar platform 1130 can be used as a support surface to hold other components that can be used in various nanospray applications. For example and as will be described in greater detail hereinafter, the planar platform 1130 can support a capillary device 1300 (shown in the embodiment illustrated in FIG. 30) that is used to ionize and inject the sample into the reservoirs 160 of the various nozzles 150 of the device 100.

Figure 29:
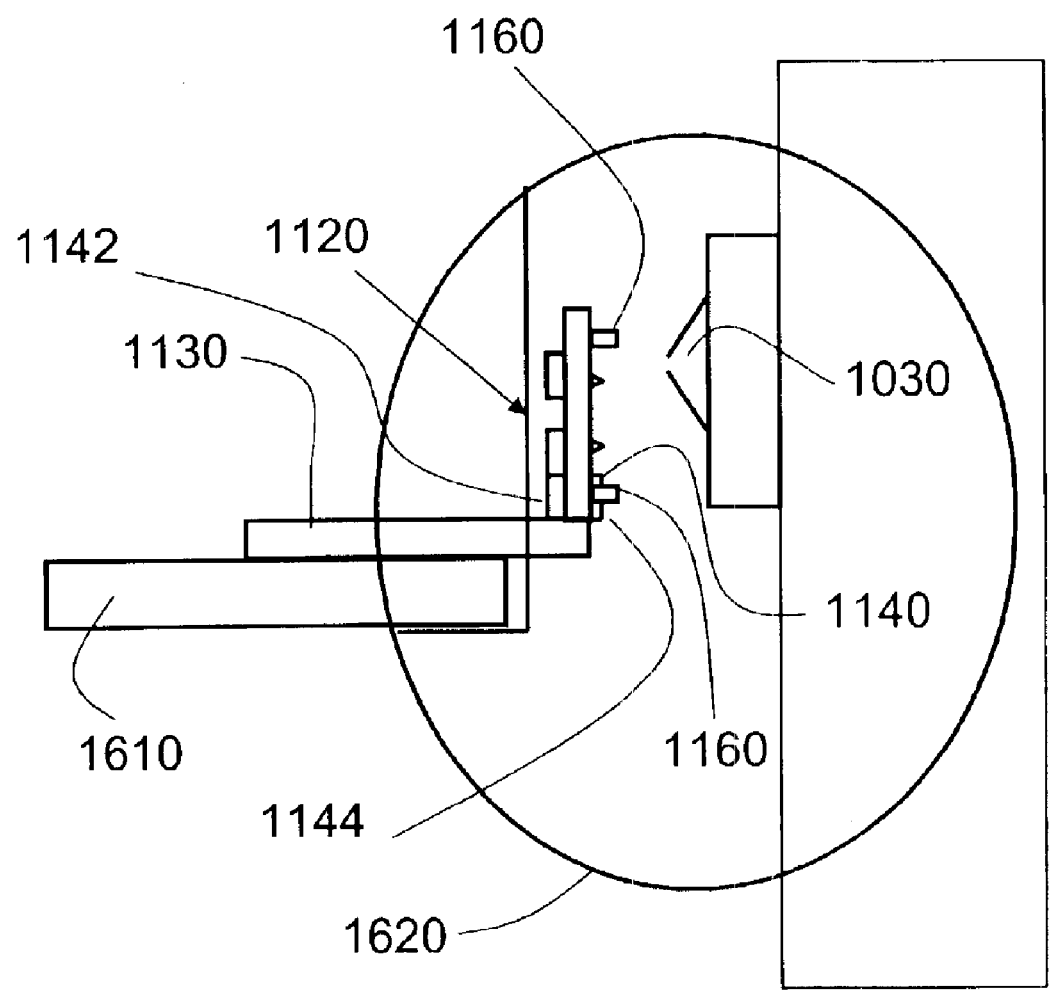
FIG. 29 is a side elevational view of a nanospray device interface in a mass spectrometer unit.

In the event that the holder 1120 is to be rigidly connected to the frame work that supports the other components of the mass spectrometer unit 1000, the holder 1120 is constructed and positioned so that when the frame 1100 is securely held between the rails 1140, 1142, at least one nozzle 150 of the nozzle array is designated as the target nozzle that is positioned in proximity to the inlet cone 1030 of the mass spectrometer unit 1000 for injecting sample therein. The precise location of the device 100 is variable so long as a sufficient amount of sample that is injected into the nozzle 150 is transferred into the inlet cone 1030. For example, in the embodiment shown in FIG. 23, the axis through the tip opening formed in the nozzle 150 is normal to the axis through the inlet cone 1030 similar to the way the conventional electrospray apparatus is arranged; however, it is not necessary for the nozzle tip opening to the be in the same plane as the opening formed in the inlet cone 1030. In contrast, the device 100 can be locked into holder 1120 so that the nozzles 150 are positioned slightly above the inlet cone 1030 (with the axis of the nozzle tip opening being normal to the axis of the inlet cone 1030). In other words, FIG. 23 is an example of an arrangement of the nanospray apparatus in the source region of the mass spectrometer unit. The nanospray apparatus is positioned such that the nozzles 150 point toward the inlet cone 1030. The substantially smaller amount of sample sprayed by the nanospray nozzle 150 than that of ESI makes it possible for the spray to point at the inlet cone 1030 without overwhelming the mass spectrometer unit 1000 with vapors. FIG. 29 shows an alternative arrangement where the axis through the nozzle opening is parallel to and in some cases axially aligned with the axis through the opening of the inlet cone 1030.

The present nanospray apparatus, including the holder 1120, accesses the source region of the mass spectrometer unit 1000 through a cut-out in the clear cover that surrounds the source region. For different makes of mass spectrometer units 1000, different covers with appropriate cut-outs will have to be fabricated to replace the original covers. However, one will appreciate that it is possible to operate mass spectrometers without surrounding the source region with a cover, but it is generally preferred to have the cover because of the presence of high voltage and relatively high temperatures in the source region.

As shown in FIG. 30, it is also preferred for the nanospray apparatus to be coupled to an automated positioning system 1400 that permits the nanospray apparatus to be easily brought into the proper position with respect to the mass spectrometer unit 1000. More specifically, the system 1400 is preferably an automated robotic system that is movable in the x, y, and z directions so as to at least permit the selected nozzle 150 of the nozzle array to be adjusted with respect to the position of the inlet cone 1030.

There are a number of robotic systems 1400 that are commercially available and are suitable for use in the present invention. Typically, the robotic system 1400 has at least an x, y, z coordinate drive system so that the device 100 is adjusted until optimum x, y, z coordinates are determined and then stored within the programmable system. Because the device 100 has a number of nozzles 150 that can be used for a given experiment or application, the system 1400 maps the x, y, z coordinates of the nozzles 150. This can be based on user inputted information, such as the nozzle array size. For example, if a device 100 having 96 nozzles 150 arranged in an 8×12 grid is selected, then the user inputs the grid array size (8×12) into the user interface (e.g., a personal computer, etc.) of the robotic system 1400 and a coordinate map is generated indicating the relative coordinate positions of all of the nozzles 150. The robotic system 1400 can receive other information concerning other parameters or characteristics of the overall system, including the type of mass spectrometer unit 1000, etc., and optimum x, y, z coordinates for the spraying nozzle 150 (one of the nozzles in the array) are determined and the robotic device 1400 moves the device 100 so that the spraying nozzle 150 is set at the optimum coordinates.

As soon as the spraying nozzle 150 has performed the spraying operation, the robotic system 1400 moves the device 100 so that another one of the nozzles 150 is disposed at the optimum x, y, z coordinates. Thus, each nozzle 150 is set at the optimum x, y, z coordinates when the spraying operation is performed and this results in a sufficient amount of sample being injected into the inlet cone 1030 for each spraying operation. In one exemplary embodiment, the robotic system 1400 has a base that is movable at least in two directions by being, for example, guided along guide rails, etc., and a robotic arm or the like is connected to the base and is likewise movable in one or more directions. Preferably, the robotic arm is movable in a number of directions and one end of the support section 1132 is connected to the robotic arm so that the holder 1120 is supported by the robotic arm and therefore movement of the robotic arm is directly translated into movement of the holder 1120.

Determining the optimum x, y, z coordinates depends upon a number of different parameters so that the goal of having a full plume spray can be achieved. Several of these parameters including, the properties of the electrospray and the diameter of the nozzle tip opening, and the user preferably observes the mass spectrometer unit 1000 as the user injects the liquid sample. By varying the applied voltage, the plume profile of the sample liquid can be varied and therefore, by varying any of the above parameters as well as others, the plume of the liquid sample can be varied to ensure that a sufficient quantity of liquid sample is injected into the inlet cone 1030. While the device 100 can be arranged above the inlet cone 1030 with the individual nozzles 150 facing downward towards the inlet cone 1030 (see FIG. 23), the device 100 can be arranged such that the axis through the nozzle opening is axially aligned with the axis through the inlet cone 1030 (see FIG. 29). In this embodiment, the nozzle tip is spaced away from the opening in the inlet cone 1030 to permit a sufficient quantity of the ionized sample to be injected into the opening extending through the inlet cone 1030.

As best illustrated in FIGS. 26–28 and 31–32, according to one aspect of the present invention, the frame 1100 is metallized in selected regions and an inner surface of at least one of the rails 1140, 1142 is metallized so that an appropriate voltage potential (e.g., ground potential in one example) is applied to the frame 1100 of the device 100 when the frame 1100 is disposed within the space 1144 between the rails 1140, 1142. The high voltage needed for spraying may be likewise applied to the liquid in the nozzle 150 through a metallized path from the reservoir 160 behind the nozzle 150 to the inside surface on the other side of the space 1144 or the high voltage can be applied through a discrete electrode placed inside the reservoir 160 behind the nozzle 150.

For example, FIGS. 26–28 and 31–32 illustrate an embodiment where an inner surface of one rails 1140, 1142 is metallized and a conductive, metallized pathway is formed on frame 1100 and the device 100 to serve either as a means for grounding the device 100 or as a means for applying high voltage to the device 100 so as to permit a nanospray application to be performed. A first conductive pathway (electrical pathway) 1143 is formed on the planar platform 1130 and includes a first end 1145 and a second end 1147 that terminates at the rail 1140 and is in electrical contact with the conductive material on the inner surface. A second conductive pathway (electrical pathway) 1151 is also formed on the planar platform 1130 and includes a first end 1153 and a second end 1155 that terminates at the rail 1142 and is in conductive contact with the conductive material on the inner surface. Preferably, the first conductive pathway 1143 is formed along one side edge of the planar platform 1130 and the second conductive pathway 1151 is formed on the opposite side edge of the planar platform 1130. Each of the first ends 1145, 1153 can terminate in a contact pad or an enlarged region that is adapted to connect to either a high voltage source or ground. The first and second conductive pathways 1143, 1151 can be formed using any number of conventional techniques, including using a printing process to lay down a conductive material according to the defined pathway. Because one of the pathways 1143, 1151 serves as a high voltage pathway and the other pathway 1143, 1151 serves as a ground pathway and therefore the two pathways cannot intersect.

In one embodiment, the conductive, metallized path extends from an edge of the frame 1100 and across the device 100 to the reservoir behind the nozzle 150 for applying high voltage to the liquid behind the nozzle 150 to ionize the sample as it passes through the nozzle 150. Each nozzle reservoir 160 can have its own associated metallized path that leads to the edge of the frame 1100 such that when the frame 1100 is disposed within the space 1144, the metallized paths formed at the edge of the frame 1100 is placed in electrical contact with an inner metallized surface of one of the rails 1140, 1142. Alternatively, some branching of the metallized paths is provided so that one metallized line at the edge of the frame 1100 can branch into two or more metallized lines that lead to two or more reservoir 160. This type of arrangement is advantageous when there is a need to energize a group of nozzles in a specific pattern simultaneously, or when there are a significant number of nozzles 150 such that if each reservoir 160 associated with each reservoir had its own associated metallized line that extended to the edge of the frame 1100, there would be significant crowding of metallized lines at the edge of the frame 1100. The metallized surface of the respective rail 1140, 1142 is then operatively connected to a high voltage source and the other of the rails 1140, 1142 is grounded by any number of conventional techniques, including forming a metallized surface on this other rail 1140, 1142 and connecting this metallized surface to ground. It will also be appreciated that the other rail 1140, 1142 does not have to include a metallized inner surface to provide a ground since there are number of other ways to provide a ground. For example, the proximity between the device 100 and the inlet cone 1030 permits the inlet cone 1030 to serve as a ground without the inlet cone 1030 being in contact with the frame 1100.

Figure 26:
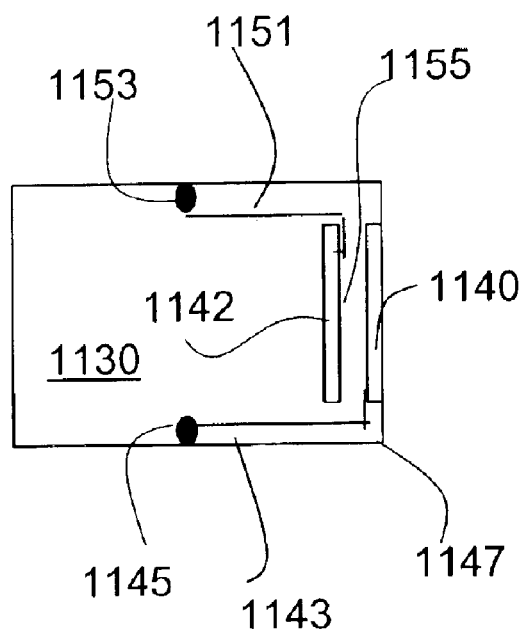
FIG. 26 is a top view of a holder for securely retaining the microfluidic device of FIG. 24.
Figure 27:
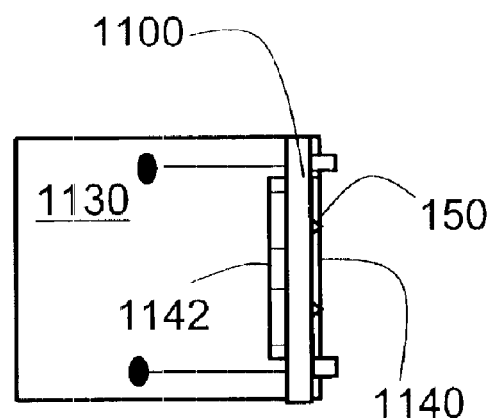
FIG. 27 is a side elevational view of the holder of FIG. 26.
Figure 28:
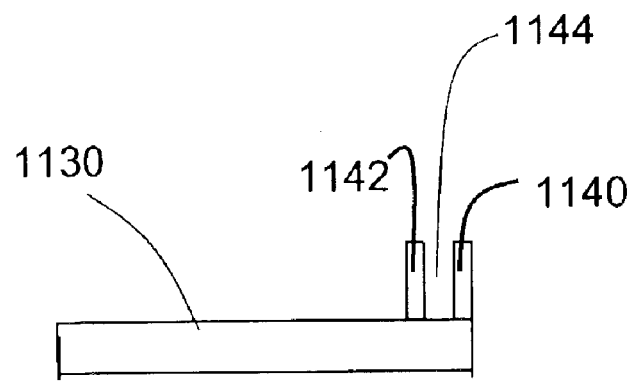
FIG. 28 is a top view of the holder of FIG. 26 with the microfluidic device being securely held therein.

The amount of conductive material disposed on the one or more inner surfaces of the rails 1140, 1142 and the precise pattern thereof can vary from application to application. For example, the precise pattern of the conductive material on each rail 1140, 1142 will depend upon the pattern of the conductive pathways formed on the frame 1100. In other words, the two conductive surfaces must mate with one another to provide an electrical pathway therebetween. FIGS. 26–27 illustrate the holder 1120 without the device 100 being disposed therein, while FIG. 28 illustrates the holder 1120 having the device 100 securely held between the rails 1140, 1142. FIG. 28 also illustrates how the posts 1160 positioned on either side of the front rail 1140 prevent lateral movement of the device 100.

Alternatively, neither the frame 1000 nor the inner surfaces of the rails 1140, 1142 has a conductive, metallized coating but rather a wire or the like can be directly inserted into the liquid sample that is disposed within the reservoir 160. The other end of the wire is connected to a high voltage source and when actuated, the liquid sample is subjected to high voltage conditions through the wire and this serves to ionize the liquid sample as it passes through the nozzle 150 from the reservoir 160 to the tip opening. The frame 1100 can be grounded using any number of techniques, including the inlet cone 1030 acting as the ground for the device 100 due to its proximity thereto.

FIG. 29 illustrates a nanospray device interface 1600 in combination with the mass spectrometer unit 1000. A mounting mechanism 1610 with x, y, and z translational movement, such as the positioning system 1400, is provided and the holder 1120 is securely attached thereto. In this embodiment, the holder 1120 has electrical contacts, such as the conductive pathways 1143, 1151, formed thereon. The holder 1120 is supported at least in part by the mounting mechanism 1610 and therefore, the translational movement of the mounting mechanism 1610 is translated to movement of the holder 1120.

A cover 1620 of the mass spectrometer unit 1000 is disposed around the inlet cone 1030 and the frame 1100 to function in the manner described hereinbefore. In this embodiment, the device 100 is vertically orientated and is disposed across from the inlet cone 1030 with the target nozzle 150 being positioned so that a sufficient quantity of the ionized spray is directed into the opening formed through the inlet cone 1030.

Furthermore, in another embodiment illustrated in FIGS. 24, 25 and 30, a metallized capillary 1300 is used and a metallized tip portion thereof is disposed within or in close proximity to the reservoir 160. The capillary 1300 serves to inject the liquid sample into the reservoir 160 and high voltage is applied to the conducting sections through a metallic or other conductive coating on the capillary 1300 and this results in the injected sample being charged. When the liquid sample flows out of the capillary into the microfluidic channel into the nozzle 150 it becomes charged when it comes into contact with the conducting coating held at high voltage at the opening of the capillary. When a metallized or conducting capillary 1300 is used, the capillary 1300 can be supported by a capillary holder 1310 (parallel to the microfluidic device 100) that is connected to the planar platform 1130 of the holder 1120 and liquid sample is injected into the capillary 1300 in a traditional manner and the metallized sections of the capillary 1300 are operatively connected to a high voltage source. When a metallized capillary 1300 is used, the device 100 does not have to have any metallized paths formed therein since the high voltage source is connected to the capillary 1300 and not the device 100.

Figure 31:
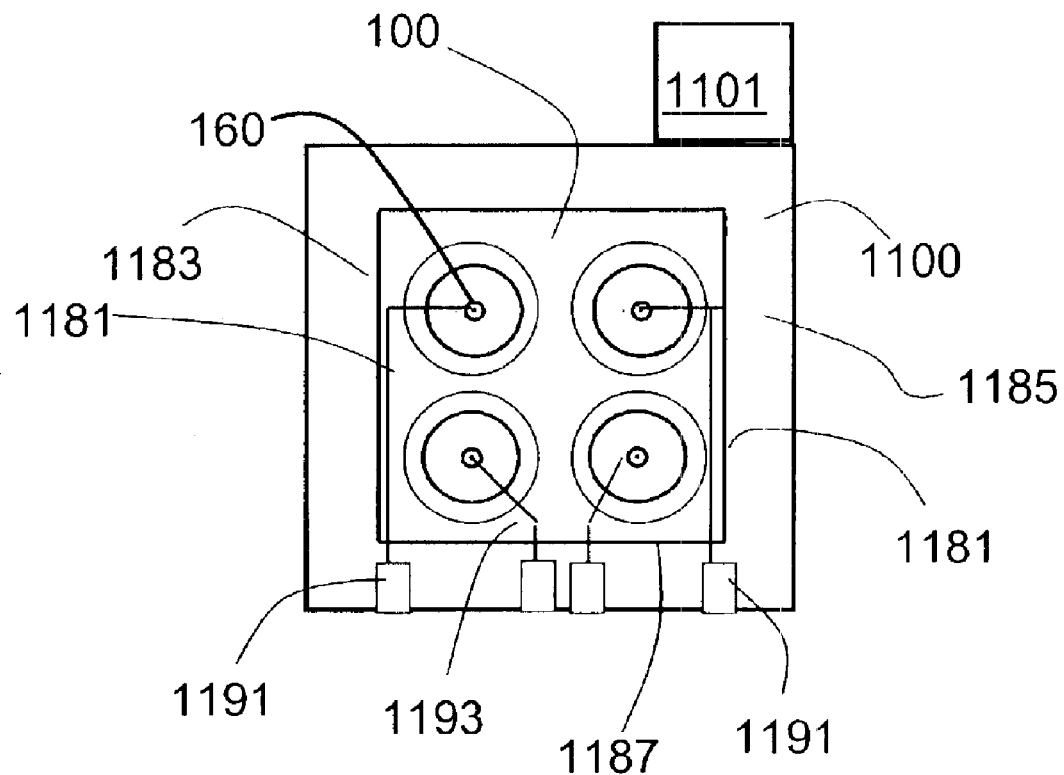
FIG. 31 is a front elevational view of a microfluidic device having an array of nozzles and a plurality of electrodes formed thereon.
Figure 32:
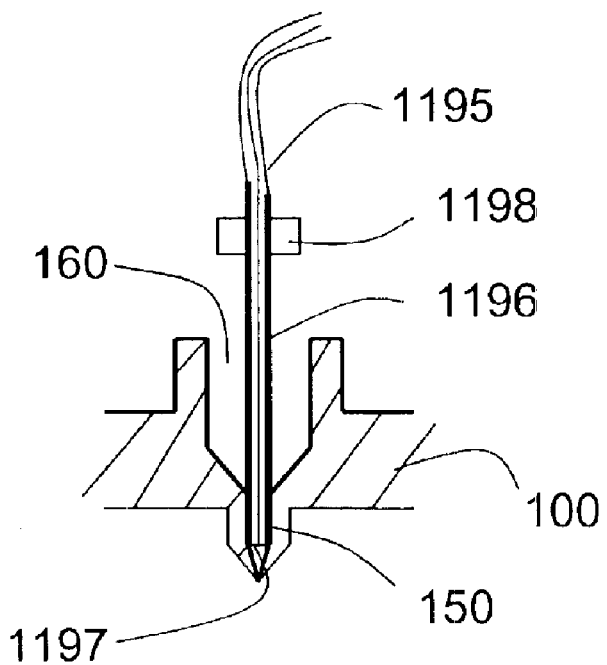
FIG. 32 is a sectional view through one nozzle and its associated reservoir of a microfluidic device according to another embodiment and a conductive capillary is provided.

FIGS. 31–32 illustrate an embodiment where the nozzle device 100 and frame 1100 have electrical pathways (electrode placements) formed thereon. FIG. 31 is a top view of the reservoir side of one exemplary embodiment where the device 100 is disposed within the frame 1100 that includes the tab 1101 for easy handling of the frame 1100. In the exemplary embodiment, the device 100 includes four nozzles 150 with their corresponding reservoirs. A pair of outer conducting pathways 1181 is formed across the device 100 and the frame 1100 and more specifically, the outer conducting pathways 1181 extends along two edges 1183, 1185 of the device 100. One end of the outer conducting pathway 1181 terminates at or near the entrance to the microfluidic channel connecting the reservoir 160 to the nozzle 150 and the other end of each pathway 1181 extends from edge 1187 and across the frame 1100 to a conducting tab 1191 formed at an edge of the frame 1100. The conducting tab 1191 preferably has greater dimensions in comparison to the pathway 1181 so that the conducting tab 1191 is in the form of an increased area of conductive material for making electrical contact with one or more electrodes formed as part of the device holder 1120. The conducting pathways 1181 and the conducting tab 1191 can be formed of any number of suitable conductive materials, such as a noble metal film or other material that can be printed on the surfaces of the device 100 and the frame 1100 according to desired patterns.

A pair of inner conducting pathways 1193 is formed across the device 100 and the frame 1100 similar to the outer conducting pathways 1181 but in different locations thereof. More specifically, the outer conducting pathways 1181 extend from the other two reservoirs 160 to the edge 1187 and are formed between the two outer pathways 1181. Similar to the outer conducting pathways 1181, each of the inner conducting pathways 1193 terminates at or near the entrance to the microfluidic channel formed through one reservoir 160 and the other end of each pathway 1193 extends from edge 1187 and across the frame 1100 to a conducting tab 1191 formed at an edge of the frame 1100. Because the reservoirs 160 that are associated with the inner conducting pathways 1193 are closer to the edge 1187, the lengths of the inner conducting pathways 1193 are less than the lengths of the outer conducting pathways 1181. Also, each outer conducting pathway 1181 has a relatively long linear section formed along one of the edges and in a manner such that it does not interfere with the other reservoirs 160. In this embodiment, there are four conducting tabs 1191 formed along the edge of the frame 1100, one for each conducting pathway that is associated with one reservoir 160. The tabs 1191 are spaced apart from one another; however, the precise spacing and arrangement of the tabs 1191 are not critical and are more a matter of design choice.

FIG. 32 is a sectional view through one nozzle 150 of the device 100 according to another embodiment. As shown, the device 100 includes the nozzle 150 and the reservoir 160. According to one embodiment, a capillary 1195 is provided for pumping liquid sample into the nozzle 150. The capillary 1195 is connected to a source of the liquid sample at one end thereof, while the other end is disposed through the microfluidic channel 30 formed through the nozzle 150. The capillary 1195 has a conductive coating 1196 disposed on a section thereof and preferably, the conductive coating 1196 is formed along an outer surface of the capillary 1195 from a point inward from a distal end 1197 to the distal end 1197 itself where the capillary 1195 enters the microfluidic channel behind the nozzle 150. In other words, the conductive coating 1196 is formed along a distal section of the capillary 1195. The capillary 1195 also includes an electrical contact 1198 that is electrically connected to a high voltage source. The electrical contact 1198 connects to the capillary 1195 at a point along the conductive coating 1196 so that an electrical connection can be established between the high voltage source and the capillary 1195 and the conductive coating 1196 provides a conducting pathway for the high voltage. Preferably, the diameter of the microfluidic channel 30 is about or equal to the outside diameter of the conductor-coated capillary 1195 to ensure a liquid tight seal when the capillary 1195 is disposed through the back of the reservoir 160 and into and through the nozzle 150 to the nozzle tip thereof. By flowing liquid sample through the capillary 1195 while simultaneously applying high voltage to the conductive coating 1196 through the electrical contact 1198, the liquid sample can be vaporized and ionized for a nanospray application.

Figure 33:
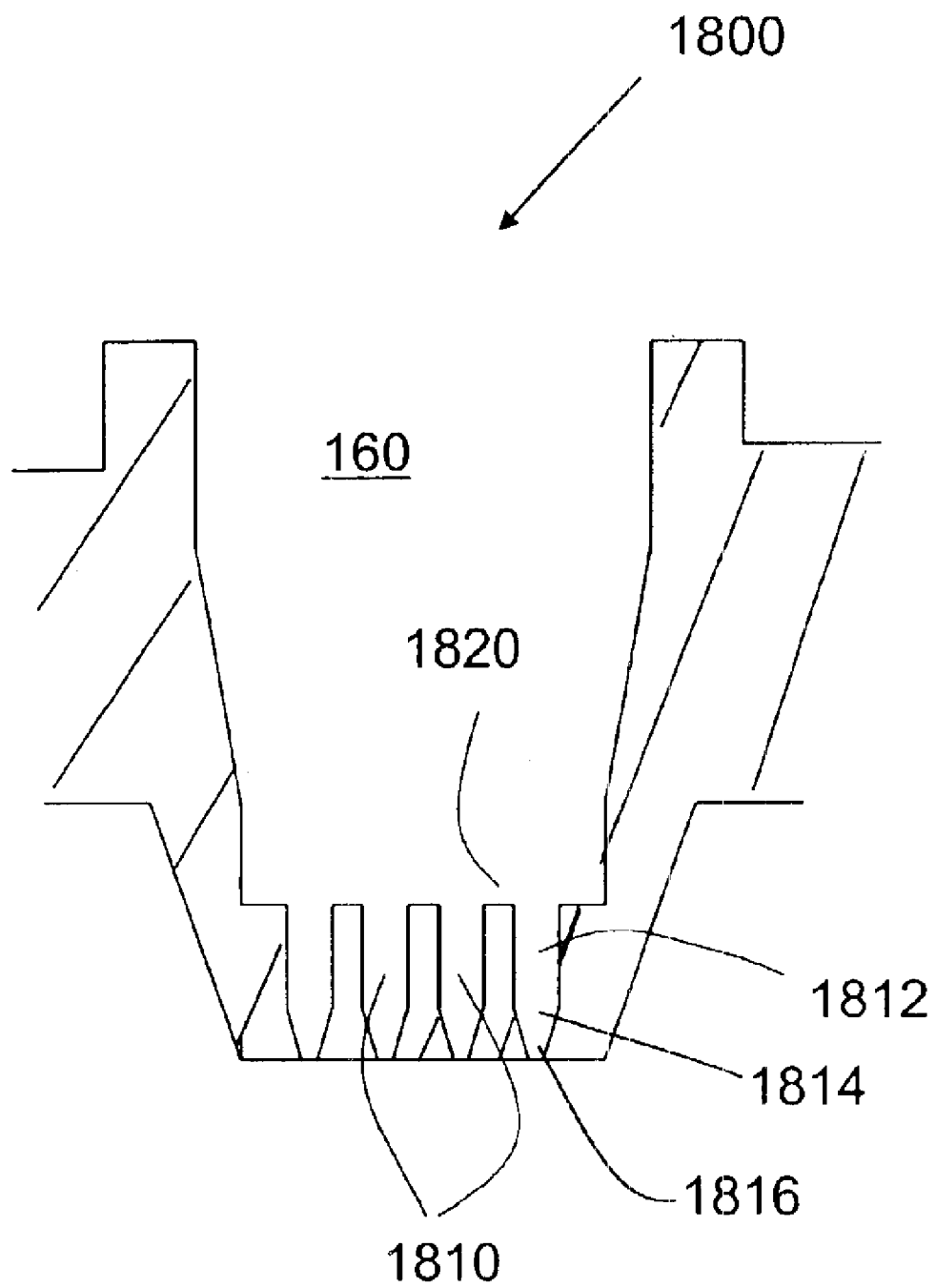
FIG. 33 is a cross-sectional view through a microfluidic device to illustrate a plurality of nozzle openings being fed from a single reservoir.

FIG. 33 illustrates a microfluidic device 1800 according to yet another aspect of the present invention. The microfluidic device 1800 is very similar to the device 100 and therefore, only the differences between the two devices are described as follows. The microfluidic device 1800 is therefore a microfluidic device formed of a plastic material that has been injected molded to form a structure having an array of nozzles formed as part thereof. In contrast to the device 100, the device 1800 is formed so that one reservoir 160 can feed two or more nozzles 1810. More specifically, each reservoir 160 has a base floor 1820 that is actually the interface between the reservoir 160 and the two or more nozzles 1810. The base floor 1820 is preferably a planar floor and it includes a number of openings formed therein which each represents an entrance into one of the nozzles 1810. Each nozzle 1810 is formed of a microfluidic channel section 1812 that tapers inwardly at a distal end to define a nozzle tip 1814 that terminates in a nozzle opening 1816. The nozzle openings 1816 thus are openings that are formed along one face of the device 1800 while the other face include much larger openings that represent the entrances to the reservoirs 160.

Preferably, each nozzle opening 1816 has a diameter between about 20 to about 50 microns and the nozzle openings 1816 can be arranged in a regular or irregular format with spacing between the nozzle openings 1816 being preferably greater than 50 microns to about several hundred microns or more. In the cross-sectional view of FIG. 32, there are a number of nozzles 1810 arranged in a linear manner, e.g., along rows, etc. It will be appreciated that the device 100 can be constructed to include only one reservoir 160 with a plurality of nozzles 1810 being in fluid communication with the one reservoir 160 so that the one reservoir feeds the plurality of nozzles 1810 with liquid sample.

In yet another aspect of the present invention, an improved process for spraying a liquid from droplets to a vapor plume using a polymeric nozzle array device, such as device 100, is provided. Spraying a liquid through a constricted opening with the aid of an electric field is widespread process for generating a vapor plume for a variety of applications. In the application for mass spectrometry, the vapor plume carrying the ions of the molecules of interest is directed into the mass spectrometer unit 1000 where the masses of the ions of the molecules are obtained. From the mass of the molecule, the chemical nature of each molecule is obtained. In the prior art, the electric field large enough to create the vapor plume is provide by the small radius of the constricted opening, or nozzle because the electric field at the nozzle is inversely proportional to the radius of the nozzle. Some examples of such nozzle devices are a glass capillary with one end tapered to less than 30 microns in diameter and an outer surface at the tapered end metallized to act as an electrode and microfabricated silicon nozzles that have an outside diameter of 35 microns. In the case of silicon nozzles that are fabricated on a planar substrate, the outside surface of the nozzle 150 is held at ground potential, and the liquid sample coming through the nozzle is charged at high voltage. Since the wall of the nozzle 150 can have a thickness of about 12.5 microns, the electric field generated by the distance between the charged liquid and the ground potential of the outside wall of the silicon nozzle (i.e., the distance of about 12.5 microns), generates an additional field that is comparable in strength as the electric field generated by the nozzle diameter. In both of these instances, the physical dimension of the nozzle radius is critical in determining whether the electric field strength generated by a given applied voltage is sufficient to cause the liquid to vaporize into a plume.

The disadvantages of the above processes are that (1) the outside diameter of the nozzle 150 must be made very small, i.e., under 35 microns, which requires expensive manufacturing process such as microfabrication technology involving photolithography and reaction ion etching or laser pulling that can crease one nozzle 150 with each pull; (2) when the outside diameter of the nozzle 150 is restricted to below 35 microns, the inside diameter of the nozzle 150 is necessarily also small, less than 10 microns; and these inside diameter are conducive to clogging of the nozzles by liquid samples that have many large molecules suspended in them; and (3) the small outside diameter of the nozzle also makes the nozzle fragile and easily damaged through routine handling.

The present process is suitable for using the polymeric nozzle device 100 for spraying a liquid through the nozzle 150 in the form of droplets, a vapor plume or multiple vapor plumes with a voltage applied to the liquid. The liquid placed behind the nozzle 150 is pumped through the nozzle 150 by liquid or gas pressure means, while a sufficiently high voltage typically in the range of about ±1 to 3.5 KV is applied to the liquid placed behind the nozzle 150 through an electrode which may be inserted into the space (e.g., reservoir 160) behind the nozzle 150, or may be a built-in electrode made by depositing a film of noble metals, such as gold, into the area behind the nozzle 150 where the liquid sample will come into contact with the electrode before emerging from the nozzle opening. As the liquid emerges from the nozzle opening, the very tip of the liquid, under the influence of the electric field created at the tip of the liquid, will spray outward from the nozzle opening. As the applied voltage is increased, the form of spray changes from large liquid drops several hundred microns in diameter to a mist of fine droplets or vapors. For mass spectrometry analysis, the spray with the fine droplets or vapor is preferred. The ions bound in each droplet are released from the fine liquid droplets when the liquid in the droplets has evaporated with or without the assistance of a desolvation gas, typically nitrogen gas flowing into the plume droplets from the opposite direction as the droplets. The ions then enter the mass selector of the spectrometer to be analyzed.

There is an alternative process to operate the nozzle device to obtain ions from a liquid sample for mass analysis. In the aforementioned process, the liquid sample is continuous pumped through the nozzle opening while a high voltage is applied to the liquid sample to obtain a spray of fine droplets. In the alternative process, the liquid sample placed inside the microfluidic channel behind the nozzle is not pumped through the nozzle, i.e., the flow-rate of the liquid through the nozzle is zero. A high voltage is applied to the said liquid sample through the conducting end of the capillary as depicted in FIG. 32. The electric field acting on the droplet of liquid in the microfluidic channel causes the vaporization and ionization of the liquid sample. The ions formed during this process do so without being bound to a large number of sprayed liquid droplets. These ions thus formed leave the microfluidic channel through the nozzle opening 150 and move toward the low potential on the reference electrode at the inlet of the mass spectrometer to be analyzed. In this manner, less than 200 nl of sample initially stored inside the microfluidic channel may generate enough ions continuously for mass spectrometry analysis for over twenty minutes. This mode of operation is especially valuable when only nanoscale amount of sample that needs high degree of accuracy of analysis through prolonged measurements is available for measurements.

In the prior art, there is an analogous mode of nanospray that is achieved without any external pumping means for the liquid sample in a capillary tube which is tapered at the spraying end to an extremely small opening, typically several microns in diameter, t The use of such small tapered ended capillary tubes creates a number of difficulties since these tapered ends are very delicate and susceptible to breaking and damage. Loading the liquid sample into such a tube is very cumbersome accordingly. In addition, the small tapered opening in the tip thereof is prone to clogging. In the present disclosed process, the liquid sample stored inside the microfluidic channel may be placed there with the aid of robust methods such as a robotic liquid dispenser or by dipping the end portion of a standard capillary tube into the liquid sample container to pick up a droplet. If a standard capillary tube is used, the capillary tube does not have a tapered construction at one end but preferably has substantially the same width along its entire length. For example, a tubular shaped capillary member is suitable for use. It will be appreciated that structure other than a capillary tube can be used so long as it contains an electrically charged end that is shaped and sized to permit the formation of a liquid sample droplet thereat.

A droplet of liquid sample, preferably less than 200 nl, is initially held at the flat, open end of the said capillary tube within the microfluidic channel of the nozzle device and extends beyond this end. The relative surface tensions and other characteristics of the liquid sample and the hydrophobic nature of the polymeric microfluidic channel ae, favor the formation of a small droplet (liquid tip) at the end of the capillary tube. The outer surface of the capillary tube has a conductive layer formed thereon at least at the end section where the droplet is formed. After inserting the capillary tube through the reservoir section, into the channel and then into the nozzle such that the droplet is contained within the nozzle, an electric field is generated at this end by coupling the conductive layer of the capillary tube to a high voltage source and then activating the voltage source to form the electric field. When high voltage is applied to the capillary tube, the droplet (liquid sample) lengthens to form a conical shape, the tip of which evaporates to form ions of the sample molecules and extremely fine nanoscale or picoscale droplets carrying charges. As opposed to the vapor plume that is created in traditional nanospray applications, the present invention does not have a liquid spray component that is nearly as defined as in the traditional nanospray applications. Instead, the discharge is comprised of ions and extremely small droplets (e.g., of nanoscale or smaller dimensions) carrying charges. Advantageously, this eliminates or substantially reduces the need for a drying mechanism to dry the liquid droplets to release the ions. In the case of traditional nanospray applications, a desolvation gas is very often needed to dry the droplets by flowing a dry nitrogen gas into the vapor plume. Thus, the present method provides a less complex system that reduces the time and cost associated with pumping sample through the capillary and also drying the liquid droplets, and consumes an extremely small quantity of the sample material.

One other difference between the present techniques using the polymeric nozzle device, whether pumped or not pumped, and the conventional nanospray technique is that the electric field for vaporizing and ionizing the liquid sample is formed by the liquid tip (the liquid sample droplet) due to its shape and location instead of the actual tapered structure of the capillary tube. The liquid tip formation is helped by the material property of the microfluidic channel containing the droplet which is preferably a material not wetted by the liquid aqueous sample. Polymeric materials or a material covered by a polymeric layer are suitable materials. Materials with good thermal conductivity are also suitable, as well as polymeric materials with impregnated electrical and thermally conducting additives such as carbon and metallic particles. In the present processes disclosed hereinbefore, the diameter of the polymer nozzle opening affects the voltage needed to create a spray of a given liquid. For a nozzle opening of 20–30 microns in diameter, the applied voltage can be between ±2 to 2.5 KV to create a fine spray of 40% methanol/60% water. When spraying with an approximately 50 micron diameter, the applied voltage can be higher to about ±3 to 3.5 KV. Once the spray has initiated, it is possible to lower the voltage to approximately 1.3 KV to maintain the spray. The outside diameter of the nozzle can vary between 50 to 150 microns. The outside diameter of the polymer nozzle can be larger than 150 microns.

The reference electrode, or counter electrode, can be placed from 0.5 mm to several mm from the nozzle opening.

The closer the counter electrode is to the nozzle opening, the lower the applied voltage has to be for the liquid to start spraying. The difference in the required voltage can be in the range of a few hundred volts for when the counter electrode is approximately 0.5 mm away and over 1 mm away from the nozzle opening.

The advantages of the present process are the following: (1) nozzles of a variety of inside diameters can be fabricated to adapt to a range of flow rate requirements and contents of the liquid samples without affecting the applied voltage greatly; (2) micro-injection molding technology for polymers produces sufficiently fine structures in nozzles fabricated from a variety of polymer materials and further injection molding is a low-cost manufacturing technology; and (3) nozzles with a relatively large outside diameter can be used to create fine plumes comparable in properties as those created by the smaller nozzles, wherein the larger outside diameter minimizes the possibility of physical damage to the nozzles.

The inside diameter of the nozzles can be made large enough to spray droplets of viscous liquid, such as polymer solutions, for application in array spotting and nano particle fabrication of polymers. Organic dyes used in organic LED display, regular dyes used in conventional ink-jet printing and other materials that require fine droplets or nanoscale droplets may be sprayed with these array devices to achieve high resolution of the droplets as well as high speed. The present design constructions thus overcome the above noted disadvantages that were associated with the prior art.

Figure 34:
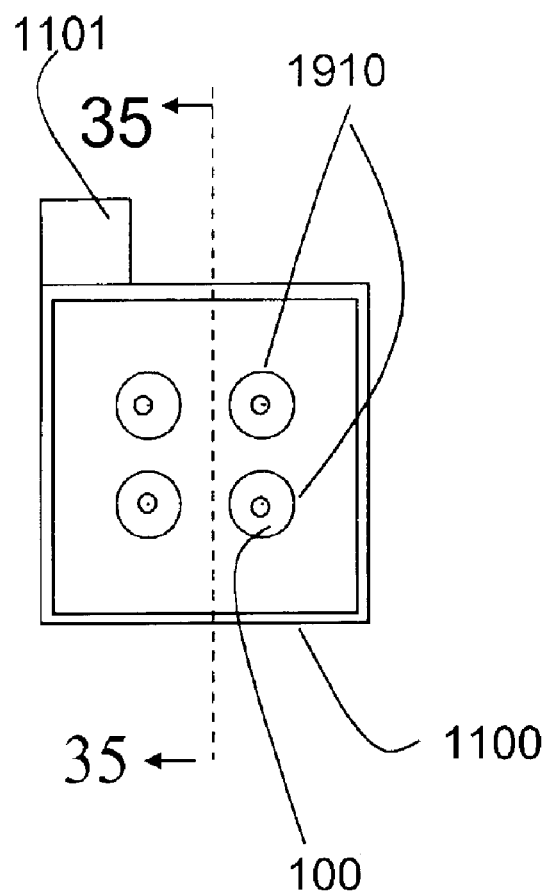
FIG. 34 is a front elevational view of a microfluidic device with frame according to another exemplary embodiment.
Figure 35:
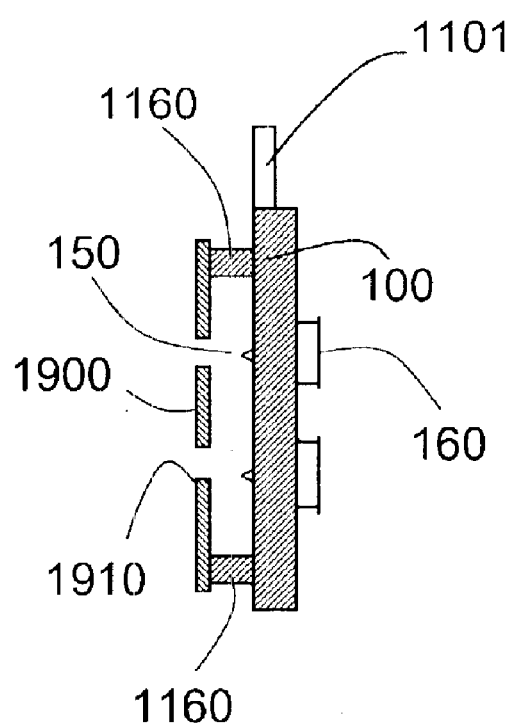
FIG. 35 is a side elevational view of the microfluidic device and frame of FIG. 34.

Turning now to FIGS. 34-35, as previously mentioned, spraying a liquid through a constricted opening with the aid of an electric field is a widespread process for generating a vapor plume for a variety of applications. In the application for mass spectrometry, the vapor plume carrying the ions of the molecules of interest is directed into the mass spectrometer where the masses of the ions of the molecules are obtained. From the mass of the molecule, the chemical nature of each molecule is identified.

The polymeric nozzle array devices described hereinbefore (e.g., device 100) each has a relatively high surface area in close proximity to the spray containing numerous ionic species. These charged species can strike the polymer surface of the nozzle array device and create static electric fields that change in an unpredictable manner as more and more charged species hit the polymer surface during the spray. If the charges are not drained away from the insulating polymer surface by some means, the stray field accumulate on the insulating surface and this will prevent the ions in the spray from getting into the inlet cone 1030 of the mass spectrometer 1000. When the stray field build-up is large enough, it subtracts the electric field felt by the droplet at the nozzle tip and stops the spraying altogether.

There are a number of different techniques or means that can be used to prevent or control the build-up of the electric field on the polymeric nozzle array device. The following are several exemplary means for preventing or controlling the build-up of the electric field on the polymeric nozzle array surface. It will be understood that one or more of the following methods for discharging the stray electric field build-up can be incorporated into the nozzle array device. First, the surface of the polymeric nozzle array device can be coated with a layer of conducting material of high resistivity, for example, about 1 gigaohm. The material can be a thin layer of noble metal coating, or a layer of salt coating. Salts that are suitable for use can be chosen from sodium iodide, rubidium iodide, silver halides, barium sulfate and the like.

Second, a capacitor of an appropriate value can be electrically connected between the polymeric nozzle array device surface and electrical ground. The capacitor is charged up by the electrical charges from the stray ions and electrons and discharges the electrical charges to electrical ground at controlled intervals. Third, a salt solution containing sodium iodide and rubidium iodide or other salts can be added to the sample liquid for spraying so that a layer of salt coats the device surface during the spray to drain the stray charges away. Fourth, an antistatic additive can be added to the polymer resin during the injection molding process so that the resultant polymeric nozzle device can have an anti-static property. The additive can be a highly conjugated polymer, such as polyaniline or the like. Likewise a premixed commercially available anti-static polymer resin as one supplied by HiTech (Hebron, Ky.) may be used for injection-molding polymeric nozzle array devices with an appropriate anti-static property. A preferred anti-static polypropylene is especially suitable.

Fifth and as illustrated in FIGS. 34-35, a conducting shield 1900 made of a sheet of metal or an insulator with a metallic coating can be placed between the nozzle tip and the mass spectrometer inlet (e.g., inlet cone 1030 of FIG. 23) to act as a physical barrier for catching the sprayed droplets that can otherwise be falling on the surface of the nozzle array device 100. The shield 1900 should have an aperture 1910 and be placed about 1 mm from the nozzle tip and the aperture 1910 should be large enough for the beginning part of the spray to come through. FIGS. 34-35 show one exemplary placement of the shield 1900. In this configuration, the shield 1900 is held at a distance defined by the height of the posts 1160 on the frame 1100 of the device 100. While the distance between the shield 1900 and the nozzle tip will vary depending on the length of the posts 1160, it is preferred that this distance be less than 1 mm. In other words, the shield 1900 can be attached to the posts 1160 and extend across the device 100 with each nozzle 150 having an associated aperture 1910 formed in the shield 1900. While, the dimensions of the shield 1900 can vary, in one exemplary construction, the shield 1900 has a thickness from about 0.005 inch to 0.010 inch.

There are a number of different ways to attach the shield 1900 to the posts 1160. For example, an adhesive or bonding material can be applied to the posts 1160 and/or select locations of the shield 1900. In addition, the shield 1900 can include a number of hubs that equal the number of posts 1160 and each posts 1160 mates with the hub so as to removably couple the shield 1900 to the posts 1160 and thereby couple the shield 1900 to the frame 1100 and the microfluidic nozzle array device 100. In one exemplary embodiment, each hub is in the form of a hollow protrusion (e.g., tube-like structure) that extends outwardly from an inner surface of the shield 1900 that faces the frame 1100. The shield 1900 is removably coupled to the frame 1100 by inserting the posts 1160 into the hollow interior of the hubs so that the two parts are securely coupled to one another. If it is desired to remove the shield 1900, the shield 1900 can simply be pulled away from the posts 1160. By having a shield that is removable from the microfluidic device 100 and the holder 1120, interchangeability of the individual components is permitted. For example, the construction of the shield 1900 depends on the construction of the device 100 and more specifically, it depends on the number and arrangement of the nozzles 150 since there needs to be one aperture 1910 for one nozzle 150. Thus, if the device 100 has a first array arrangement, a first shield 1900 is required and if the device 100 has a second array arrangement that is different from the first arrangement, a second shield 1900 is likely required. Further, because the shield 1900 is not rigidly connected to or made integral with the holder 1120, the holder 1120 can be used with a number of different types of shields 1900 and microfluidic devices 100.

In an alternative embodiment, the shield 1900 is removably coupled to the holder 1120 using mechanical fasteners. For example, the shield 1900 can have securing tabs extending outwardly therefrom the receive fasteners that are securely attached to the holder 1120 itself, thereby resulting in the shield 1900 being securely yet removably attached to the holder 1120. In other words, fasteners, such as screws or the like, are used to removably attach the shield to the holder 1120. In this embodiment, the shield 1900 is preferably positioned so that the inner surface of the shield 1900 seats against the posts 1160 after the shield 1900 is securely fastened to the holder 1120. This is desirable because the posts 1160 can then be used to space the shield 1900 the proper distance from the nozzle tips. Thus, regardless of the actual construction of the shield 1900, it will be uniformly placed a prescribed distance from the nozzle tips by making sure that the shield 1900 seats against the posts 1160 when it is fastened to the holder 1120. In this embodiment, the shield 1900 can either be placed above the rail 1140 or on the planar platform 1130. The shield 1900 can also be made as an integral part of posts 1160 in that a molding process can be used to form the frame 1100, posts 1160 and the shield 1900 integrally attached thereto.

In yet another embodiment, the rail 1140 can be constructed so that it includes a longitudinal groove extending therein. The longitudinal groove is sized so that the shield 1900 is received therein in a snug manner so as to securely couple the shield 1900 to the holder 1120. In other words, the frictional fit between the shield 1900 and the rail 1140 securely holds the shield 1900 in a vertical position parallel to the microfluidic device 100. Once again, the shield 1900 preferably seats against the posts 1160 for the above reasons when the shield 1900 is securely held in the groove of the rail 1140. In this embodiment, the shield 1900 is removable since it can easily be pulled out of the groove formed in the rail 1140.

Figure 36:
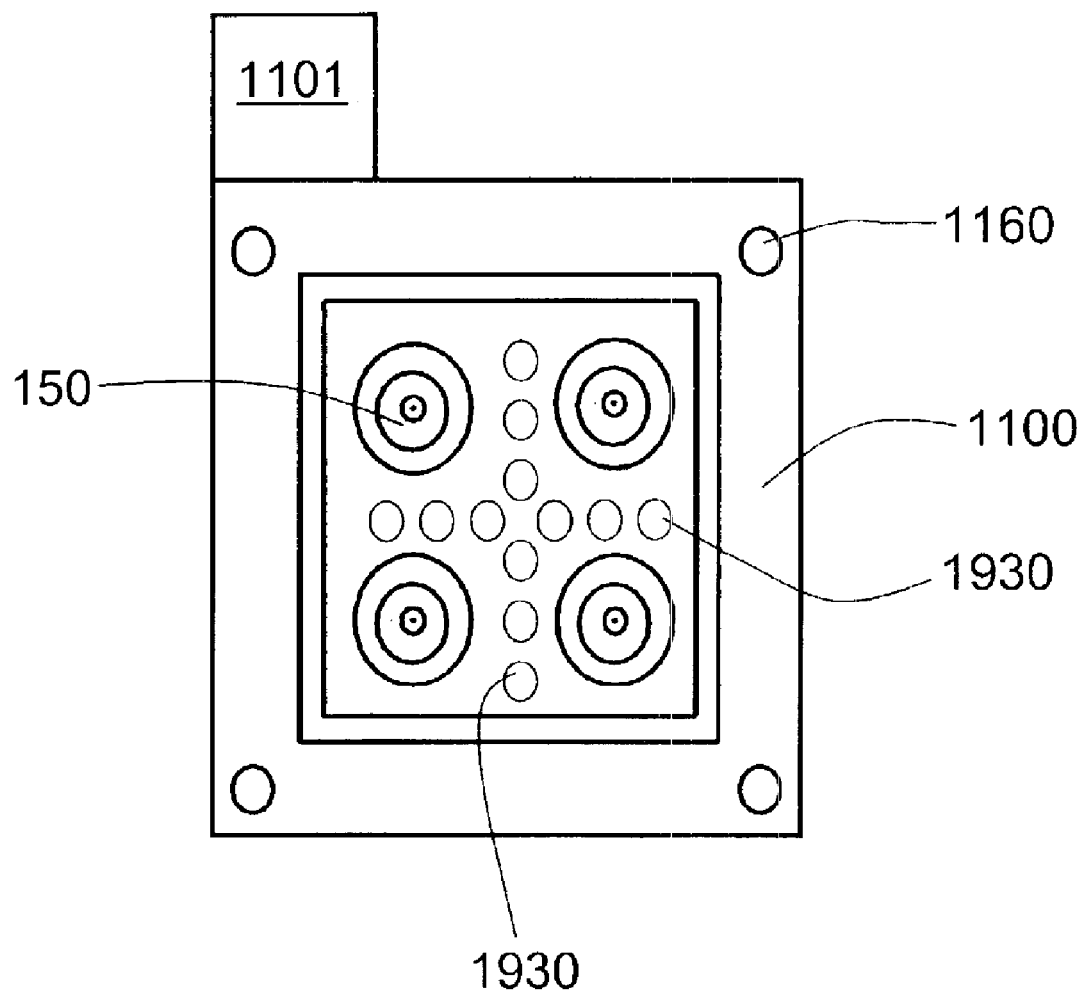
FIG. 36 is a front elevational view of a microfluidic device with frame according to yet another embodiment.

Sixth and as illustrated in FIG. 36, the nozzle array device 100 can have the amount of plastic perpendicular to the spray direction reduced by placing through holes 1930 in the surface of the array device 100. In this embodiment, the body of the nozzle cone (nozzle 150) can also be made longer so that the distance between the nozzle tip and the flat surface of the nozzle array device 100 perpendicular to the spray direction is maximized.

It will be appreciated that the aforementioned means to prevent or control the build-up of the electric field on the polymeric nozzle array surface can be used in combination with any of the microfluidic nozzle array devices disclosed herein.

While the invention has been particularly shown and described shown and described with reference to preferred embodiments thereof, it will be understood by those skilled in the art that various changes in form and details may be made therein without departing from the spirit and scope of the invention.

What is claimed is:

1. A microfluidic device comprising: a body having a first surface and an opposing second surface, the body having at least one channel formed therein and extending through the body from the first surface to the second surface, wherein the channel has a reservoir section that is open at the first surface; at least one nozzle disposed along the second surface, the nozzle being in fluid communication with the channel such that one end of the channel terminates in a nozzle opening that is formed as part of the nozzle; and a coating of conducting material of high resistivity disposed on the second surface of the body.

2. The microfluidic device of claim 1, wherein the resistivity of the conducting material is about 1 gigaohm and greater.

3. The microfluidic device of claim 1, wherein the conducting material is one of a thin layer of a noble metal and a thin layer of a salt coating with the salt being selected from the group consisting of sodium iodide, rubidium iodide, and barium sulfate.

4. The microfluidic device of claim 1, further including a member for holding the microfluidic device and providing an interface between the microfluidic device and a second device, the member comprising: a body having an upper face and a lower face and a plurality of open well members formed therein, each well member being defined by a well wall and includes a first end and an opposing second end, wherein the second end is configured and dimensioned for frictionally engaging the microfluidic device such that at least one of the open well members and the reservoir of the microfluidic device align with one another.

5. The microfluidic device of claim 4, wherein the body comprises an injection molded piece of plastic material.

6. The microfluidic device of claim 4, wherein the well wall has a construction that tapers inwardly from the first end to the second end.

7. The microfluidic device of claim 4, wherein the well member has a frusto-conical shape.

8. The microfluidic device of claim 4, wherein the microfluidic device comprises an injection molded article and each reservoir formed therein is in fluid communication with an integral nozzle that has a tip opening have a diameter of equal to or less than about 100 $\mu$m and an outer diameter of the nozzle is equal to or less than about 150 $\mu$m.

9. The microfluidic device of claim 8, wherein the tip opening has a diameter of less than about 20 $\mu$m and the outer diameter of the nozzle is less than about 50 $\mu$m.

10. The microfluidic device of claim 4, wherein the second end of the well wall has an outer surface and an inner surface that is frictionally fit around an outer surface of a wall of the reservoir of the microfluidic device, thereby securely coupling the member and the microfluidic device to one another.

11. The microfluidic device of claim 4, wherein the second end of the well wall has an inner surface and an outer surface that is frictionally fit within an inner surface of a wall of the reservoir of the niicrofluidic device, thereby securely coupling the member and the microfluidic device to one another.

12. The member microfluidic device of claim 4, wherein the lower face extends beyond a lowermost section of the microfluidic device when the microfluidic device is coupled to the member so as to protect the lowermost section.

13. The microfluidic device of claim 12, wherein the lowermost section of the microfluidic device includes the at least one nozzle.

14. The microfluidic device of claim 4, further including: a puncturable sealing mat which extends across the first ends of the well walls to prevent evaporation of sample that is disposed within the well members.

15. The microfluidic device of claim 4, wherein at least some of the first ends of the well wall are joined together.

16. The microfluidic device of claim 4, wherein the second device comprises robotic dispensing equipment.

17. The microfluidic device of claim 4, wherein the microfluidic device includes an array of nozzles with active nozzles thereof each being in fluid communication with one reservoir and one well member such that a sample volume for feeding the nozzle is defined by a combined volume of the reservoir and the well member.

18. The microfluidic device of claim 4, wherein the number of well members and the number of reservoirs is equal.

19. The microfluidic device of claim 4, wherein the number of well members and the number of reservoirs is different.

20. The microfluidic device of claim 1, wherein a plate member for holding the microfluidic device and providing an interface between the microfluidic device and a second device, the plate member comprising: a body formed of an injection molded plastic material and having an upper face and a lower face and means for retainingly holding the microfluidic device while also increasing an effective volume of the reservoir of the microfluidic device.

21. The microfluidic device of claim 20, wherein the means comprises a plurality of open ended well members formed in the plate member, each well member being defined by a well wall that has a first end and an opposing second end, wherein the second end is configured and dimensioned for frictionally engaging the microfluidic device such that at least one of the well members and the reservoir of the microfluidic device align with one another.

22. The microfluidic device of claim 20, wherein one of the number and arrangement of the well members is different than one of the number and arrangement of the reservoirs of the microfluidic device.

23. The microfluidic device of claim 20, wherein the microfluidic device includes an array of nozzles formed along a surface thereof.

24. The microfluidic device of claim 1, further including an apparatus for interfacing with a mass spectrometer to perform a nanospray application, wherein the apparatus includes a frame disposed around a periphery of the microfluidic device much that the microfluidic device is securely held therein; and a holder having first and second retaining members spaced apart a sufficient distance for the frame to be disposed between and held in place by the first and second retaining members, wherein in a retained position, the at least one nozzle is positioned for spraying a sample into an inlet of the mass spectrometer.

25. The apparatus microfluidic device of claim 24, wherein the frame includes a plurality of locating and locking features that engage one of the first and second retaining members of the holder to restrict lateral movement of the frame.

26. The apparatus microfluidic device of claim 25, wherein each of the locating and locking features comprises a post extending outwardly from one face of the frame and each of the first and second retaining members of the frame comprises an elongated rail extending upwardly from a support surface of the holder, wherein in the retained position, one of the elongated rails is disposed between two posts such that a frictional fit results therebetween.

27. The microfluidic device of claim 26, wherein each post has a distal end that extends beyond the nozzle tip for protecting the nozzle.

28. The microfluidic device of claim 24, wherein the frame includes a tab extending outwardly from one edge thereof to permit a user to grasp and hold the frame.

29. The microfluidic device of claim 24, wherein the channel has a cylindrical shape along at least a substantial length thereof, the channel being defined by a seamless cylindrical surface.

30. The microfluidic device of claim 24, wherein the channel is inwardly tapered such that the dimensions of the channel are greatest in the reservoir section and are at a minimum at the nozzle opening.

31. The microfluidic device of claim 24, wherein the at least one nozzle extends beyond the second surface and is substantially conically shaped.

32. The microfluidic device of claim 24, wherein the nozzle has an outside diameter equal to or less than about 50 $\mu$m.

33. The microfluidic device of claim 24, wherein the nozzle opening has a diameter equal to or less than about 20 $\mu$m.

34. The microfluidic device of claim 24, wherein the at least one channel and the at least one nozzle are arranged in a geometrical array.

35. The microfluidic device of claim 24, wherein the body and the at least one nozzle comprise a injection molded structure that is formed of a polymeric material that cube injection molded.

36. The microfluidic device of claim 24, wherein the holder includes an upper planar surface that supports the first and second retaining members that are in the form of elongated rails that are arranged parallel to one another so that inner surfaces of the elongated rails face one another with at least one of the inner surfaces having a conductive material disposed along a section thereof.

37. The microfluidic device of claim 36, wherein the conductive material is a metal that is formed as a coating on the section of the inner surface.

38. The microfluidic device of claim 36, wherein the conductive material is electrically connected along a conductive pathway formed on the upper planar surface to one of a high voltage source and a ground.

39. The microfluidic device of claim 36, wherein each of the inner surfaces of the elongated rails has conductive material disposed thereon and the upper planar surface of the holder includes a first electrical pathway formed thereon and extending from a first location to the conductive material of one elongated rail where electrical contact is made therewith and a second electrical pathway is formed and extends from a second location to the conductive material of the other elongated rail where electrical contact is made therewith, the first and second locations being opposite one another along edges of the holder.

40. The microfluidic device of claim 36, wherein the microfluidic device includes an electrode formed thereon and positioned at or near the at least one nozzle, the electrode being electrically connected to the conductive material disposed on the section of the inner surface of the elongated rail.

41. The microfluidic device of claim 40, wherein the electrode includes an electrical pathway that extends across a surface of microfluidic device and the frame to a conducting tab formed at one edge of the frame for making electrical contact with the conductive material on the inner surface of the elongated rail, wherein at least at portion of the electrical pathway extends along an inner surface of the reservoir section and the channel.

42. The microfluidic device of claim 41, wherein the conductive material is electrically connected to a high voltage source so that high voltage is provided to the at least one nozzle for ionizing the sprayed sample.

43. The microfluidic device of claim 24, further including: a capillary having a first end in fluid communication with a source of the sample and a second end being disposed through the reservoir and into the at least one nozzle so that the capillary sealingly mates with the nozzle; a conductive layer formed on an outer surface of the capillary and along at least a section of the capillary that includes the second end; and a connector coupled to the capillary and in contact with the conductive layer so that high voltage can be provided through the connector to the conductive layer.

44. The microfluidic device of claim 43, wherein the outer diameter of the conductive-coated capillary is about equal to the inner diameter at least a section of the reservoir or the microfluidic channel connecting the reservoir to the nozzle tip to provide a liquid tight seal between the capillary and the nozzle.

45. The microfluidic device of claim 43, wherein the conductive layer is a metal layer disposed around the outer surface of the capillary.

46. The microfluidic device of claim 43, further including: a capillary holder securely connected to the holder for holding the capillary relative to the microfluidic device so that the capillary extends through the reservoir section and into the at least one nozzle, the capillary holder and the frame being parallel to one another.

47. The microfluidic device of claim 24, wherein one reservoir section is in fluid communication with a plurality of nozzles.

48. The microfluidic device of claim 47, wherein the microfluidic device comprises an injection molded member and each of the plurality of nozzles are arranged according to a pattern with each nozzle opening into the one reservoir section so that sample placed in the one reservoir section flows into the plurality of nozzles.

49. The microfluidic device of claim 48, wherein the nozzle opening for each nozzle has a diameter between about 20 microns and about 50 microns.

50. The microfluidic device of claim 49, wherein the nozzles are formed so that the nozzles are spaced at least about 50 microns from one another.

51. The microfluidic device of claim 24, further including: a positioning device operatively coupled to the holder for positioning the at least one nozzle relative to an inlet of the mass spectrometer, the positioning device permitting movement of the holder in x, y, and z directions.

52. The microfluidic devices of claim 24, wherein the microfluidic device is formed of a polymer resin that includes an anti-static additive added to the polymer resin during an injection molding process so that the resultant microfluidic device has an anti-static property.

53. The microfluidic device of claim 1, further including a frame disposed around a periphery of the microfluidic device such that the microfluidic device is securely held therein; a holder having retaining features for securely holding the frame relative to the holder, wherein in a retained position, the at least one nozzle is positioned for spraying a sample; and a shield coupled to at least one of the frame and the holder so that one face of the shield faces the second surface of the microfluidic device, the shield having at least one aperture formed therein which is in axially alignment with the tip of the at least one nozzle.

54. The microfluidic device of claim 53, wherein the shield comprises a conductive shield that is removably coupled to one of the frame and the holder.

55. The microfluidic device of claim 53, wherein the frame includes a plurality of posts extending outwardly from one face of the frame with each post having a distal end that extends beyond the nozzle tip for protecting the nozzle, the shield being removably coupled to the posts so that the shield is held substantially parallel to the frame.

56. The microfluidic device of claim 55, wherein the shield includes a plurality of hubs that frictionally yet removably receive the posts.

57. The microfluidic device of claim 53, wherein a distance between the one face of the shield and the second surface is defined as a length of the post and the distance from the one face of the shield to the tip of the nozzle is equal to or less than about 1 mil.

58. The microfluidic device of claim 53, wherein the shield in formed of an insulating material with a metallic coating formed thereon.

59. The microfluidic device of claim 55, wherein the shield is integrally molded with the posts.

* * * * *